(12) United States Patent
Togino et al.

(10) Patent No.: US 6,926,409 B2
(45) Date of Patent: Aug. 9, 2005

(54) PROJECTION VIEWING SYSTEM

(75) Inventors: Takayoshi Togino, Koganei (JP); Kazuo Morita, Hachioji (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 10/636,848

(22) Filed: Aug. 8, 2003

(65) Prior Publication Data

US 2004/0085517 A1 May 6, 2004

(30) Foreign Application Priority Data

Aug. 9, 2002 (JP) ........................................ 2002-232531
Oct. 1, 2002 (JP) ........................................ 2002-288404
Feb. 14, 2003 (JP) ........................................ 2003-036619

(51) Int. Cl.[7] .......................... G03B 21/00; G02B 27/22
(52) U.S. Cl. .............................. 353/7; 353/10; 359/462; 359/478
(58) Field of Search .................... 353/7, 10; 359/462, 359/478

(56) References Cited

U.S. PATENT DOCUMENTS

| | | | | |
|---|---|---|---|---|
| 5,609,939 A | * | 3/1997 | Petersen et al. | 428/141 |
| 5,790,284 A | * | 8/1998 | Taniguchi et al. | 359/15 |
| 2003/0137731 A1 | * | 7/2003 | Takahashi et al. | 359/462 |

FOREIGN PATENT DOCUMENTS

| | | | |
|---|---|---|---|
| JP | 06-230738 | 8/1994 | G09G/3/02 |
| JP | 9-127312 | 5/1997 | G02B/5/00 |
| JP | 9-258642 | 10/1997 | G03H/1/04 |
| JP | 10-115878 | 5/1998 | G03B/35/20 |
| JP | 11-084291 | 3/1999 | G02B/26/10 |
| JP | 2000-66105 | 3/2000 | G02B/17/08 |
| JP | 2000-171618 | 6/2000 | G02B/5/02 |
| JP | 2001-281583 | 10/2001 | G02B/26/10 |

* cited by examiner

Primary Examiner—Judy Nguyen
Assistant Examiner—Melissa J. Koval
(74) Attorney, Agent, or Firm—Pillsbury Winthrop Shaw Pittman LLP

(57) ABSTRACT

The invention relates to a projection viewing system of simplified construction and high illumination efficiency, which enables at least two of images varying with viewing directions to be simultaneously displayed in a viewable fashion. The system comprises display devices 1L and 1R for displaying images, projection optical systems 2L and 2R for magnifying and projecting images 3L and 3R displayed on the display devices 1L and 1R, a diffusing plate 5 located in the vicinity of images projected through the projection optical systems 2L and 2R and an eyepiece optical system 4 for projecting exit pupils of the projection optical systems 2L and 2R on the positions of the eyeballs of a viewer. The diffusing plate 5 has an angle of diffusion of up to 20° at full width half maximum.

28 Claims, 61 Drawing Sheets

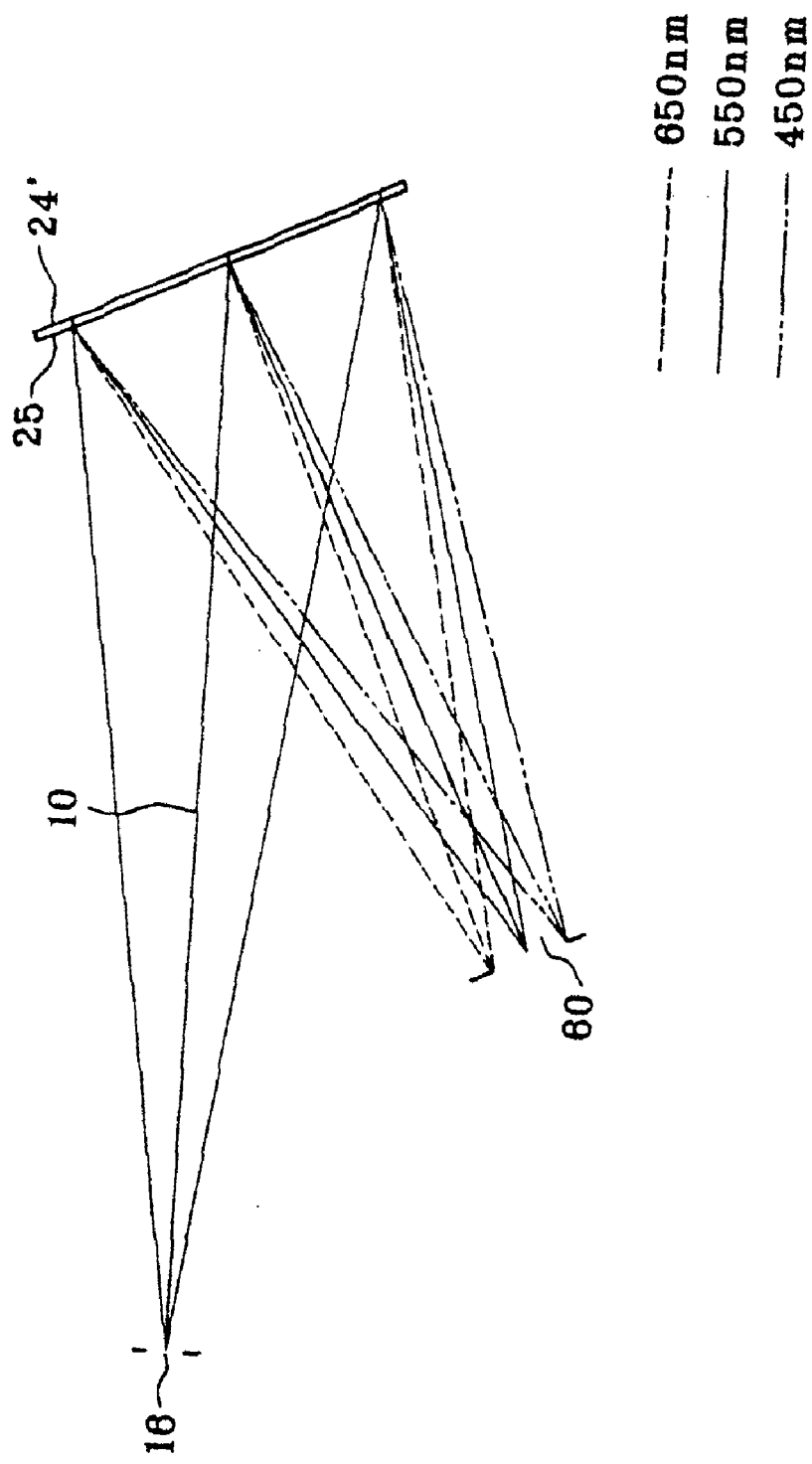

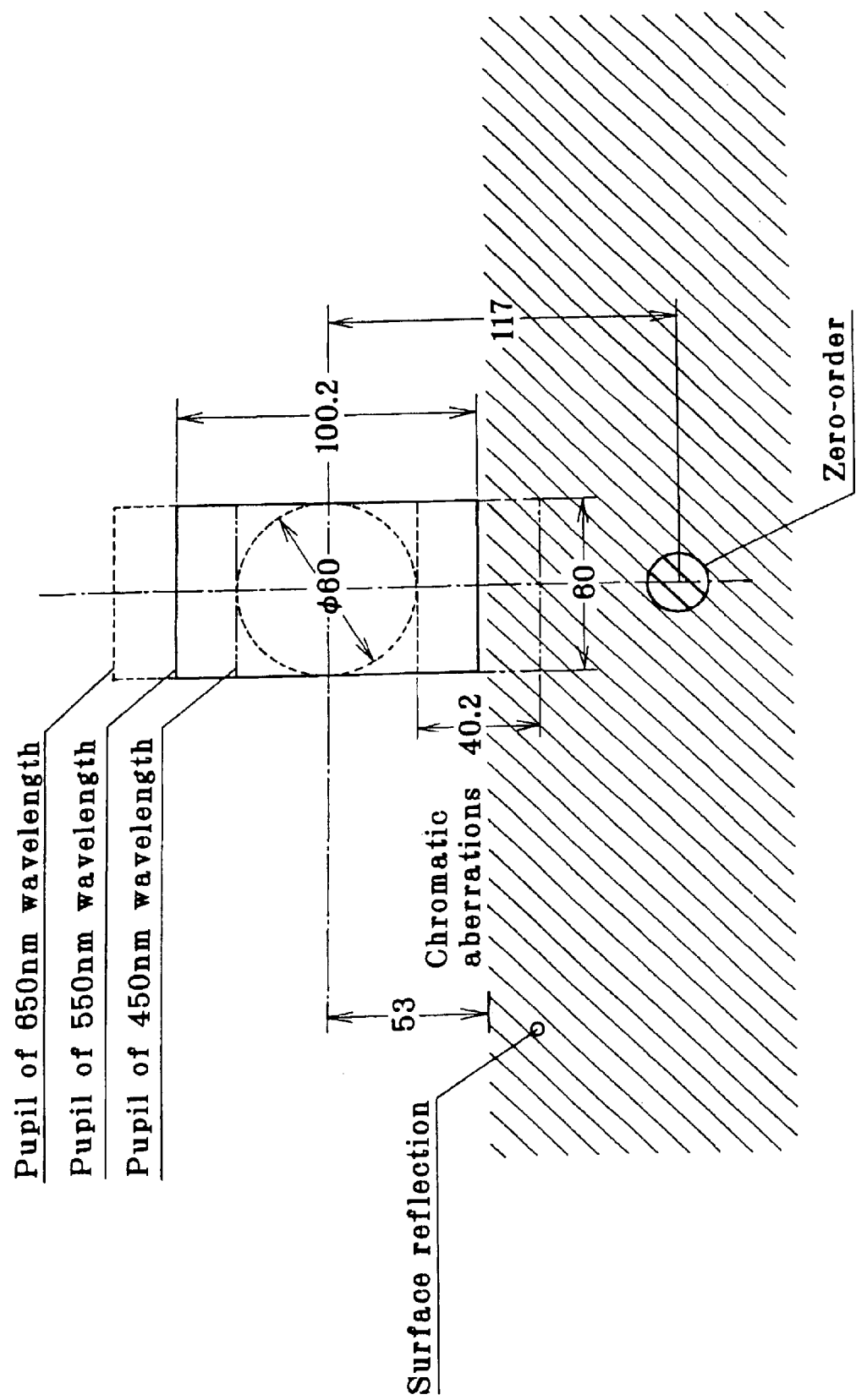

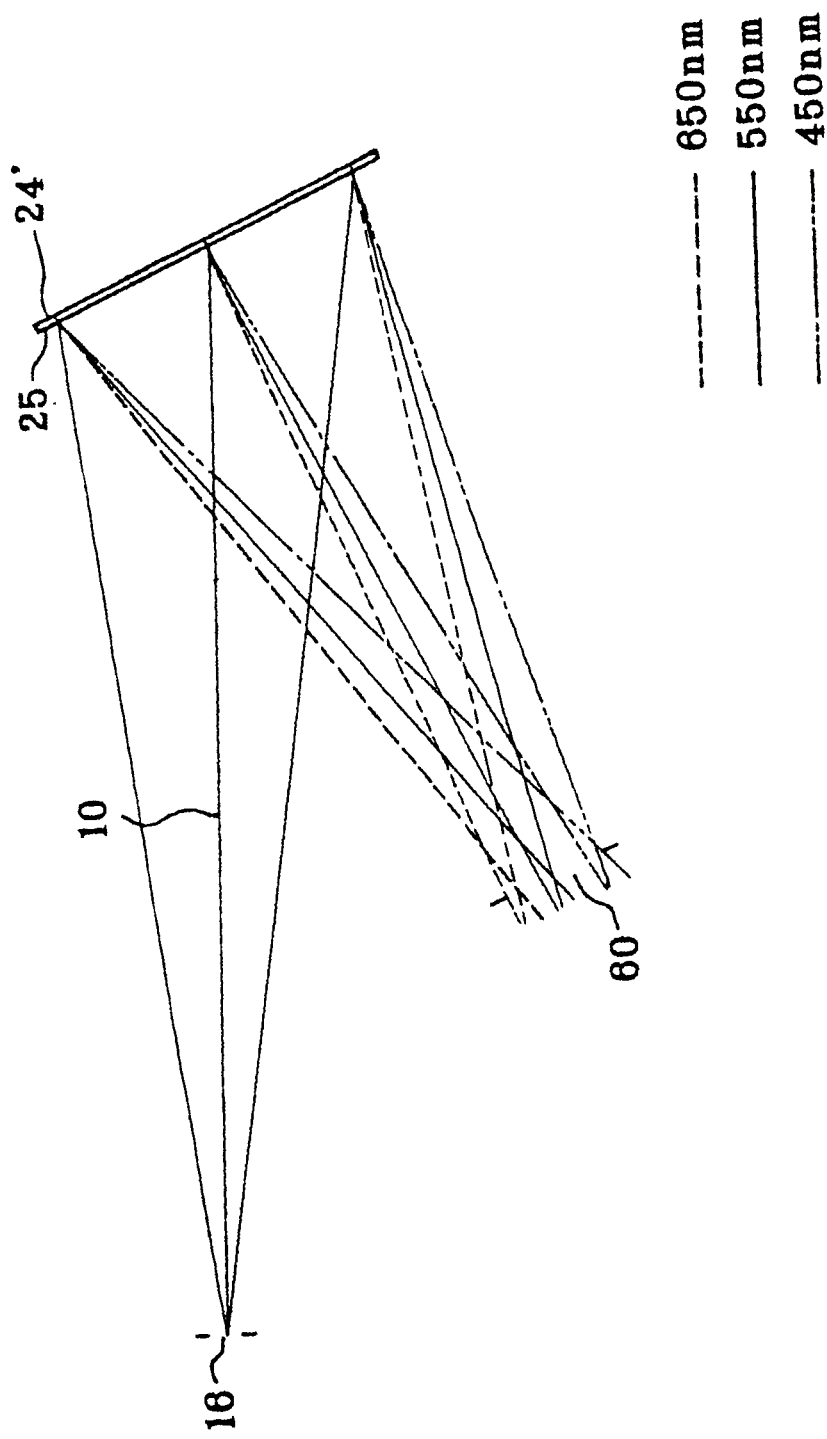

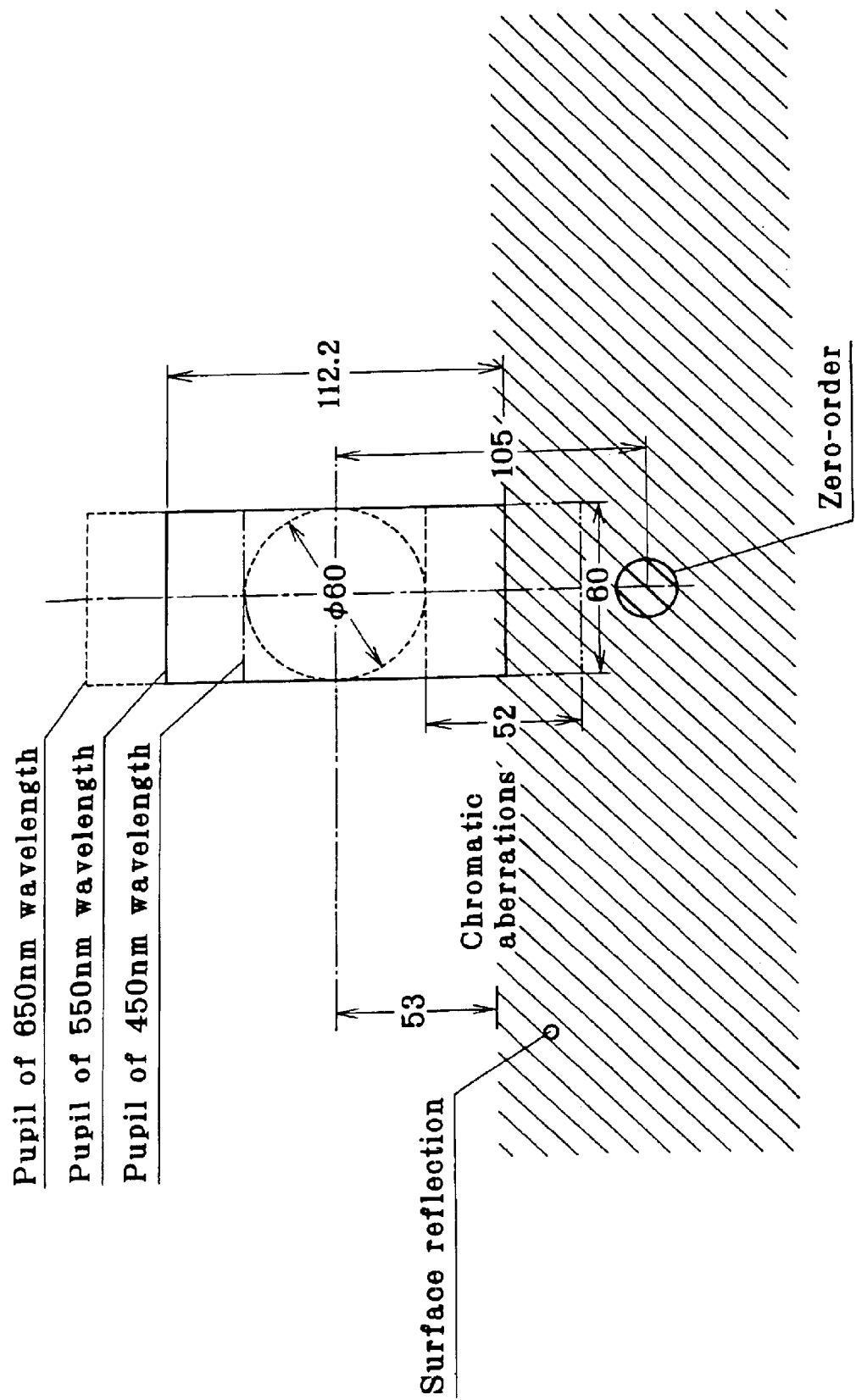

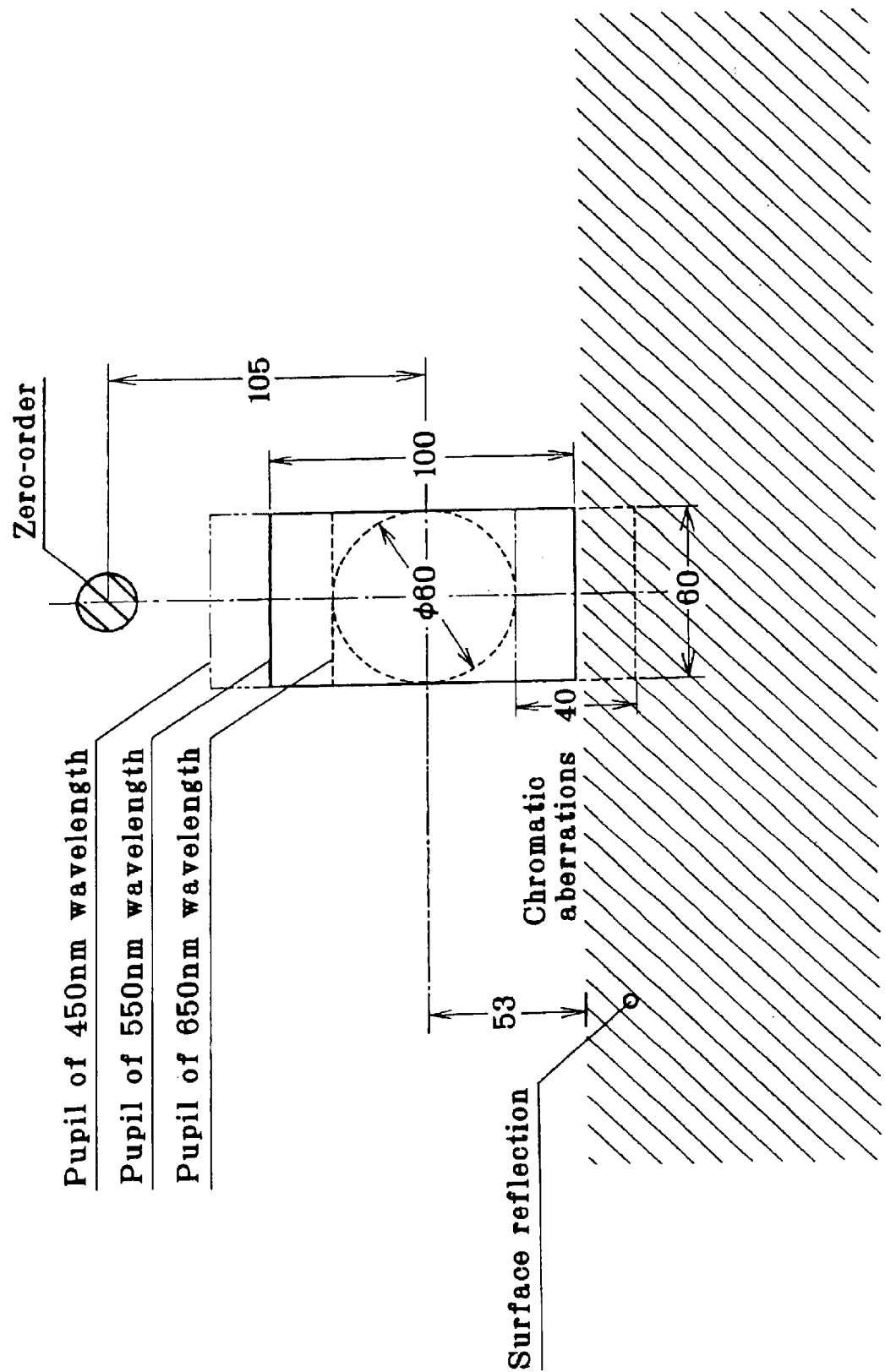

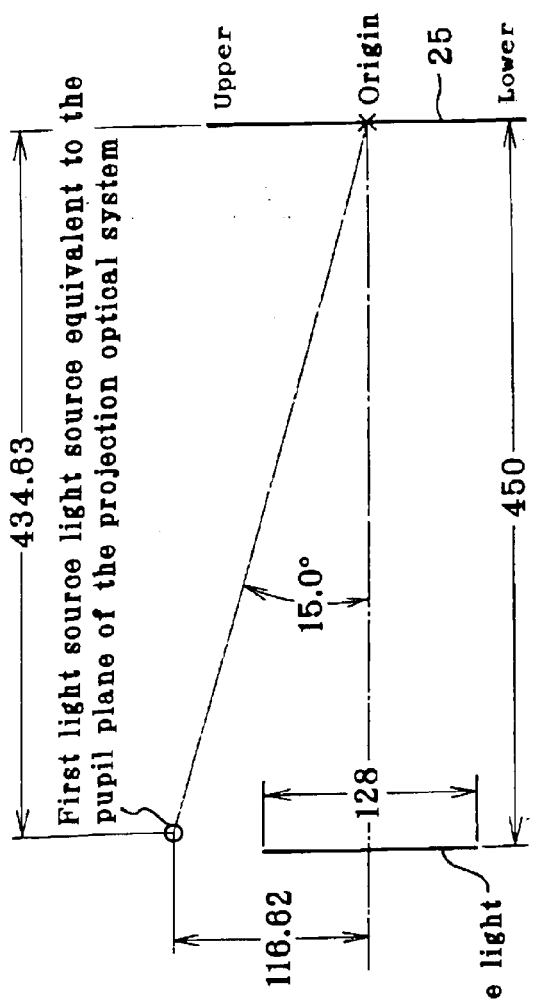
FIG. 45(a)
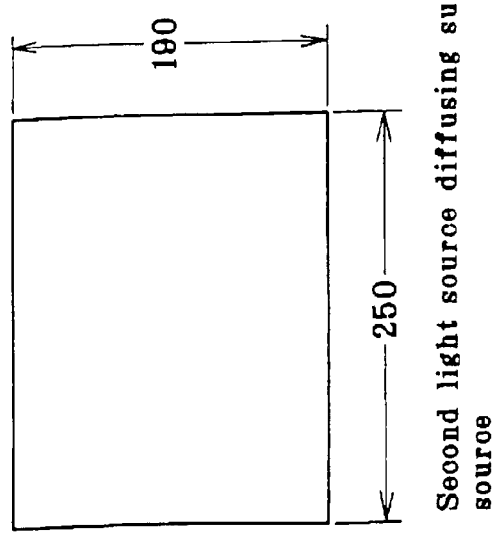
FIG. 45(b)
FIG. 45(c)

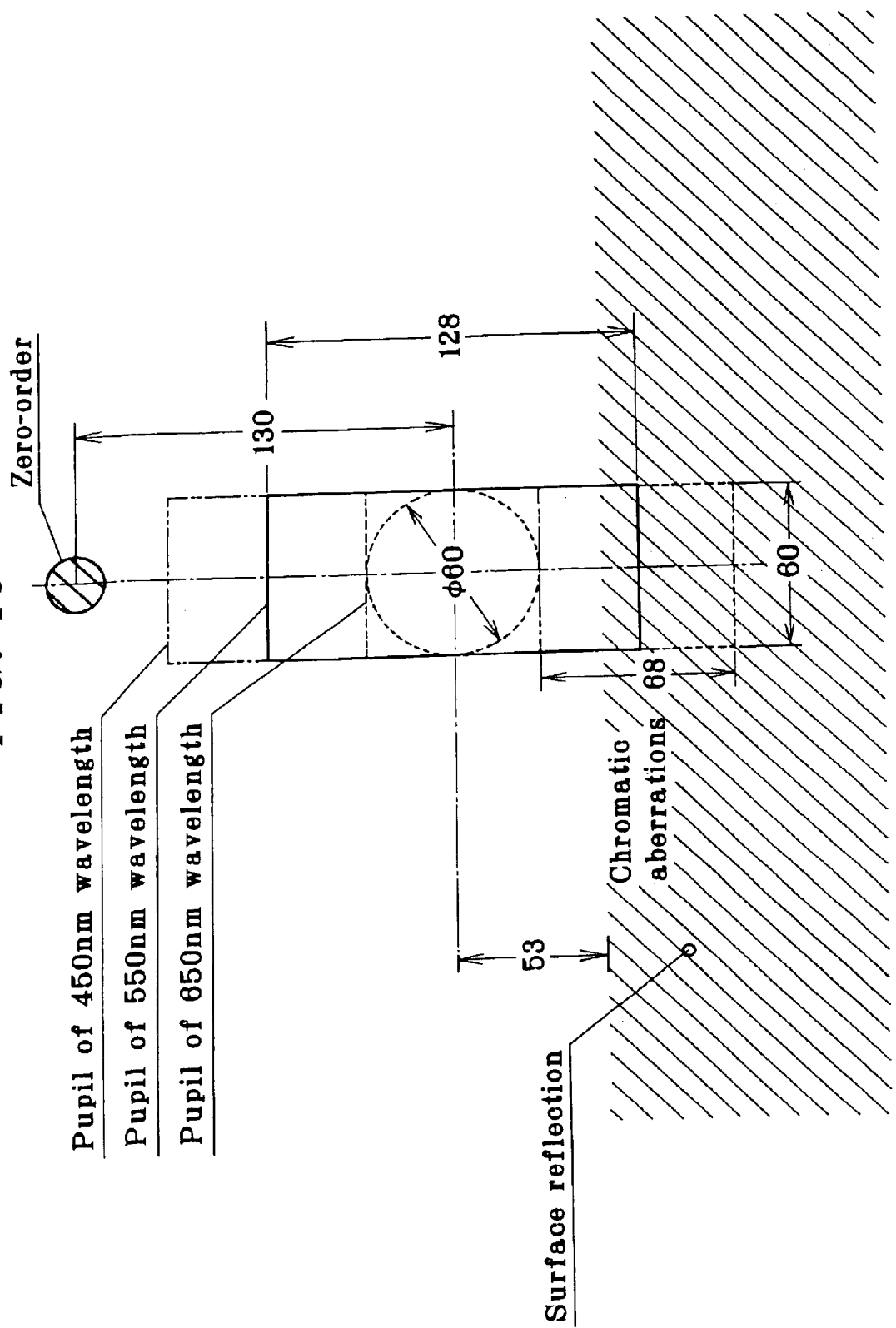

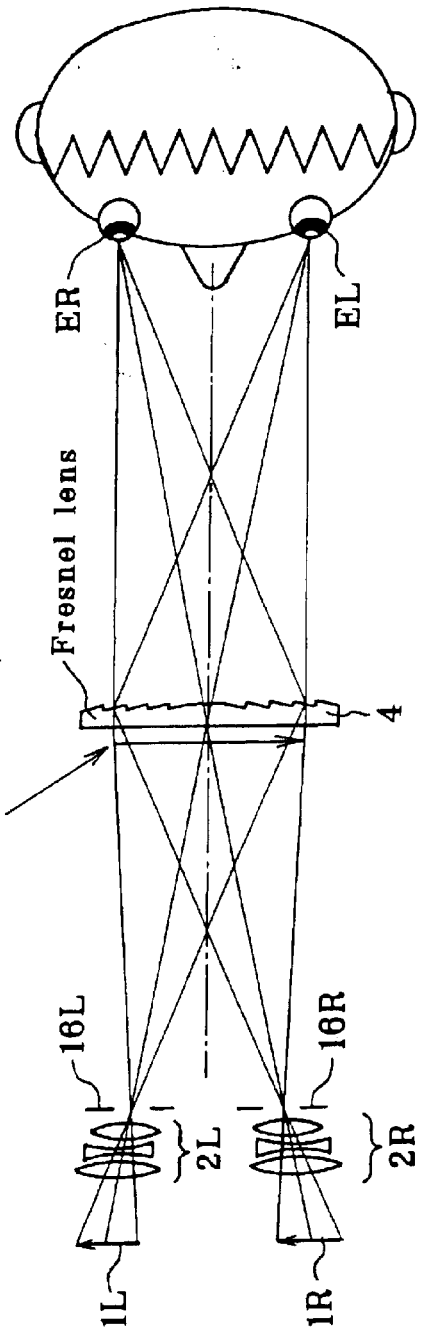
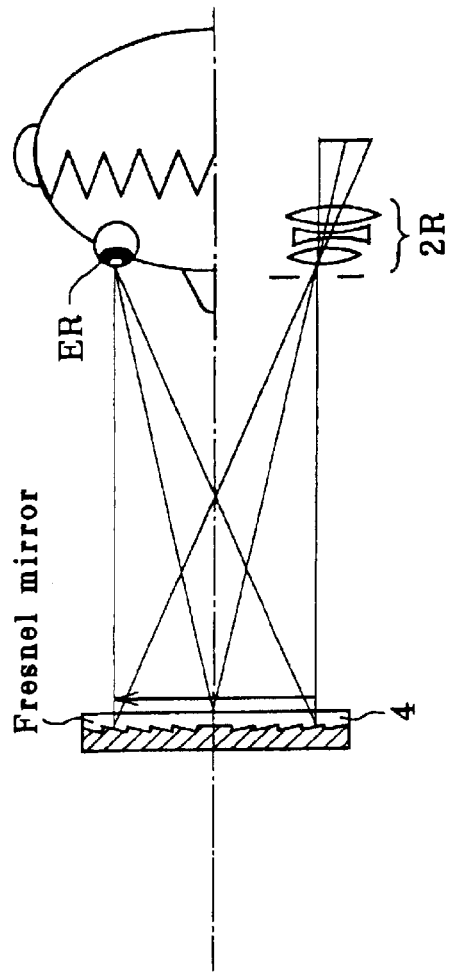
FIG. 47(a)
FIG. 47(b)

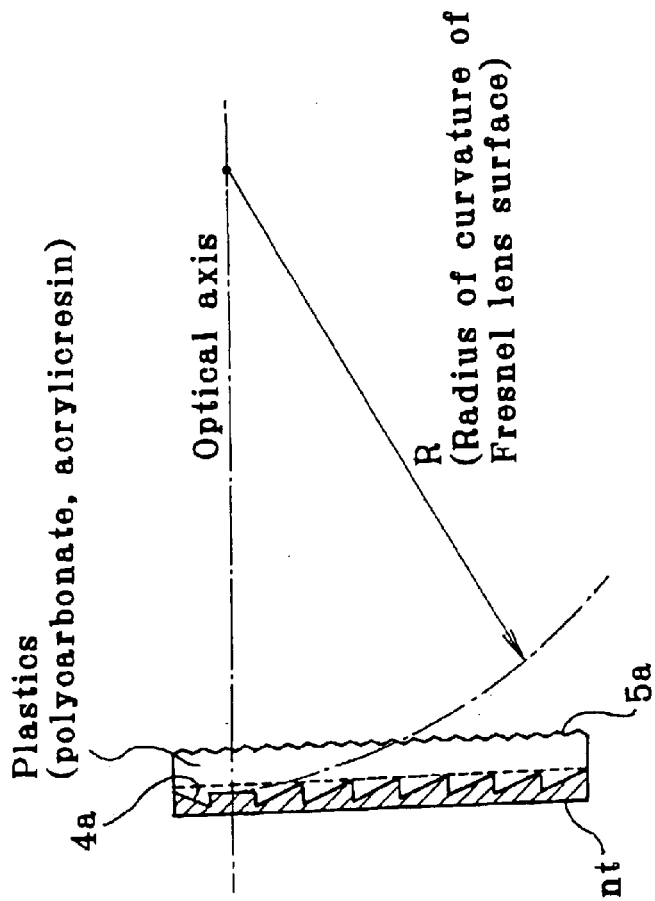
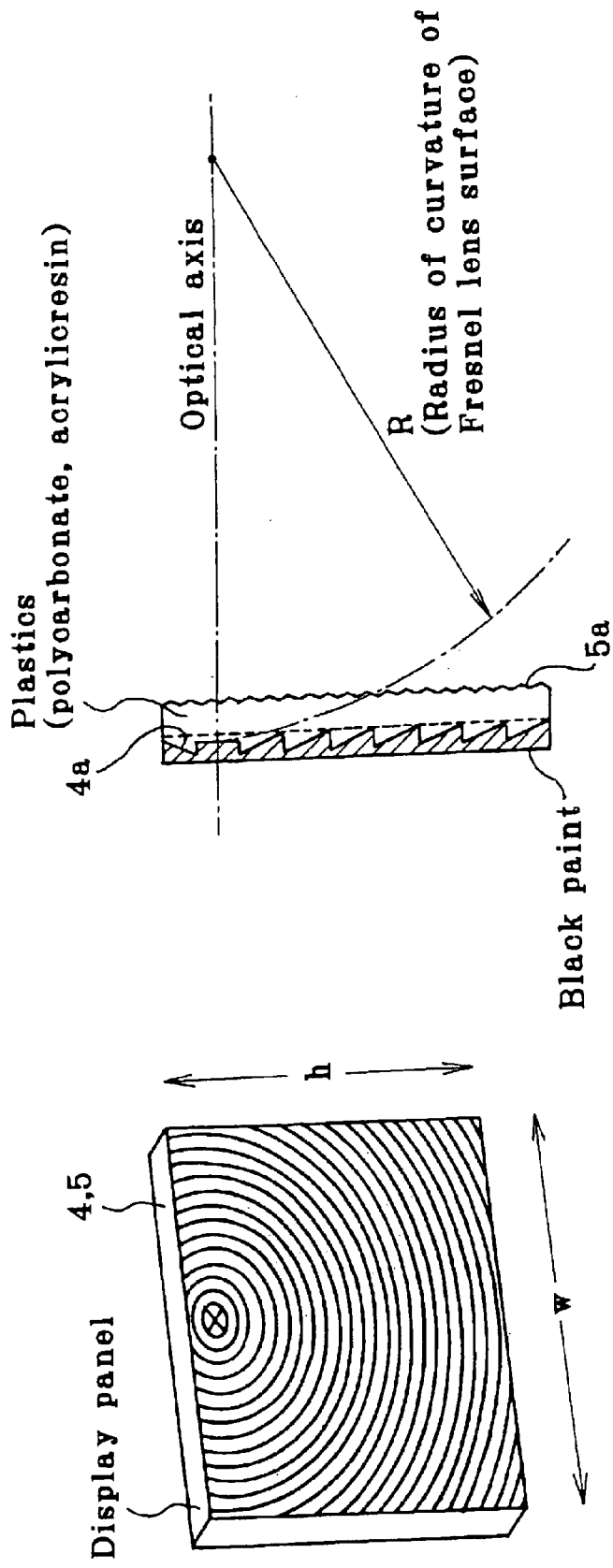
FIG. 53(b)
FIG. 53(a)

PROJECTION VIEWING SYSTEM

This Application claims benefit of Japanese Application No. 2002-232531, filed on Aug. 9, 2002; Japanese Application No. 2002-288404, filed on Oct. 1, 2002; and Japanese Application No. 2003-036619, filed on Feb. 14, 2003, the entire contents of which are incorporated herein by reference.

BACKGROUND OF THE INVENTION

The present invention relates generally to a projection viewing system, and more particularly a projection viewing system that enables an image projected (formed) at a given position to be simultaneously viewed from different directions.

Patent Publication 1 discloses how to display an image that differs depending on a viewing direction on the same screen, wherein a double-lenticular screen is used. Patent Publication 2 discloses a system for displaying stereoscopic images, wherein a reflexive screen and two projectors are used together. In Patent Publication 3, the applicant has proposed an image display system that enables an image to be viewed with both eyes. In that system, two polarizing mirrors are used in combination with a decentered prism. In Patent Publication 4, there is proposed an optical scanner of small size, wherein a single two-dimensional scanning mirror is combined with a decentered prism.

Patent Publication 1
JP-A 6-230738
Patent Publication 2
JP-A 10-115878
Patent Publication 3
JP-A 11-84291
Patent Publication 4
JP-A 2001-281583
Patent Publication 5
JP-A 9-127312
Patent Publication 6
JP-A 2000-171618
Patent Publication 7
U.S. Pat. No. 6,124,989
Patent Publication 8
JP-A 2000-66105
Patent Publication 9
JP-A 9-258642

SUMMARY OF THE INVENTION

The present invention provides a projection viewing system, comprising:
an image display device,
a projection optical system for magnifying and projecting an image displayed on the image display device,
a diffusing plate located in the vicinity of an image projected through the projection optical system, and
an eyepiece optical system for projecting an exit pupil of the projection optical system on a viewer side, wherein the diffusing plate has an angle of diffusion of up to 20° at full width half maximum.

Still other objects and advantages of the invention will in part be obvious and will in part be apparent from the specification.

The invention accordingly comprises the features of construction, combinations of elements, and arrangement of parts, which will be exemplified in the construction hereinafter set forth, and the scope of the invention will be indicated in the claims.

BRIEF DESCRIPTION OF THE DRAWINGS

FIG. 35 is an optical path diagram illustrative in Y-Z section of Example 10 of the invention.

FIG. 37 is illustrative of to what degree RGB exit pupil images overlap at the position of the exit pupil of Example 10 and the positions of incidence of zero-order light and surface reflected light.

FIG. 38 is an optical path diagram illustrative in Y-Z section of Example 11 of the invention.

FIG. 40 is illustrative of to what degree RGB exit pupil images overlap at the position of the exit pupil of Example 11 and the positions of incidence of zero-order light and surface reflected light.

FIG. 43 is illustrative of to what degree RGB exit pupil images overlap at the position of the exit pupil of Example 12 and the positions of incidence of zero-order light and surface reflected light.

FIG. 45 is illustrative of how to fabricate a transmission hologram used as the diffusing plate in Example 13 of the invention.

FIG. 46 is illustrative of to what degree RGB exit pupil images overlap at the position of the exit pupil of Example 13 and the positions of incidence of zero-order light and surface reflected light.

FIG. 47($a$) is illustrative in schematic of a transmission type stereoscopic viewing system, and FIG. 47($b$) is illustrative in schematic of a reflection type stereoscopic viewing system.

FIGS. 53($a$) and 53($b$) are illustrative of one embodiment of the reflection type display panel that is applicable to the reflection type stereoscopic viewing system of the invention.

DESCRIPTION OF THE PREFERRED EMBODIMENTS

Why the aforesaid arrangement is used in the invention, and how it works is now explained.

Figure 1:
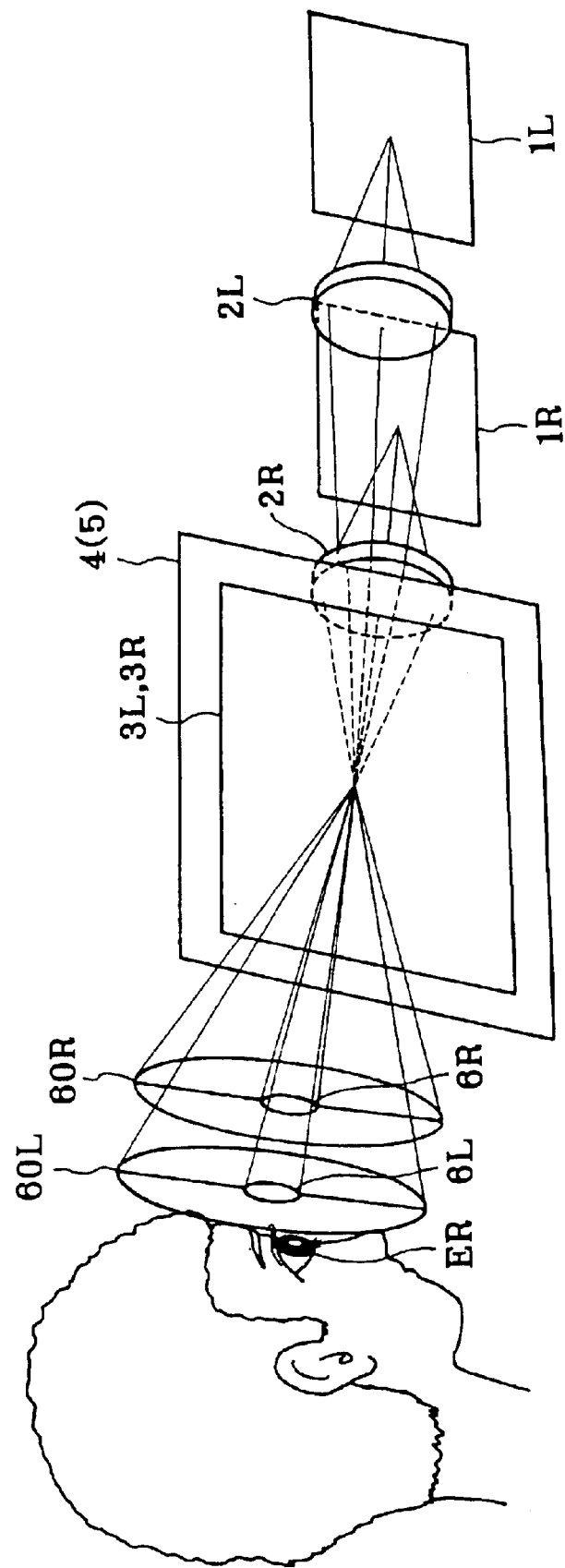
FIG. 1 is illustrative in conception of the optical system in the first projection viewing system according to the invention.

FIG. 1 is illustrative in conception of the optical system in the first projection viewing system of the invention. The projection viewing system of the invention comprises a display device 1, a projection optical system 2, a diffusing plate 5 and an eyepiece optical system 4. The display device 1 displays an image. The projection optical system 2 magnifies and projects the image displayed on the display device 1. The projected image 3 is projected on a given first position. The diffusing plate 5 is located in the vicinity of an image 3 projected through the projection optical system 2, i.e., in the vicinity of the given first position. The eyepiece optical system 4 projects the exit pupil of the projection optical system 2 onto a given second position. Upon viewing, the eyeball E of the viewer is in line with that given second position. It is here understood that the eyeball E of the viewer is not necessarily in strict line with the given second position; that is, some misalignment is acceptable.

With the projection viewing system shown in FIG. 1, images for the left eye EL and the right eye ER are simultaneously displayed on a single display (projection) plane. However, it is acceptable to display an image for either one eye alone.

Referring more specifically to FIG. 1, two display devices 1L and 1R are located to display images for both the left eye and the right eye. The same image or different images could be displayed on both display devices 1L and 1R. The same image could be an image with or without binocular parallax. In association with the two display devices 1L and 1R there are provided two projection optical systems 2L and 2R. Thus, an image displayed on the display device 1L is projected through the projection optical system 2L onto the given first position, and an image displayed on the display device 1R is projected through the projection optical system 2R onto the given first position.

The given first position defines a common display (projection) plane, at which a single eyepiece optical system 4 is located. Thus, the eyepiece optical system 4 provides a common optical system with respect to two display devices 1L and 1R, two projection optical systems 2L and 2R and projected images 3L and 3R.

The images 3L and 3R (hereinafter called the projected images 3L and 3R) projected through two projection optical systems 2L and 2R are projected onto the vicinity of the eyepiece optical system 4 while they are completely superposed on each other as shown in FIG. 1. With this arrangement, it is possible to display various images on a small display plane even when the eyepiece optical system 4 is of small size. The "various images" used herein could include a bilaterally different image, a bilaterally identical image, and a bilaterally identical image having binocular parallax.

It is here noted that the degree of superposition of the projected images 3L and 3R could be slightly short of 100%.

This eyepiece optical system 4 projects the exit pupils of the projection optical systems 2L and 2R on the viewer side. In FIG. 1, the projected exit pupils of the projection optical systems 2L and 2R (hereinafter referred to as the exit pupil images) are indicated at 6L and 6R. At the positions of the exit pupil images 6L and 6R the eyeballs EL and ER of the viewer are located. As a consequence, the eyepiece optical system 4 projects the exit pupils of the projection optical systems 2L and 2R onto the vicinity of the eyeballs EL and ER of the viewer. With such an eyepiece optical system 4, it is possible to focus projection rays leaving the projection optical systems 2L and 2R, with efficiency, on the eyeballs EL and ER of the viewer. It is thus possible to view a bright image under observation even when a light source of low output is used to illuminate the display devices 1L and 1R.

Further in the invention, a common single diffusing plate 5 is located in the vicinity of the projected images 3L and 3R. The diffusing plate 5 is then allowed to have given diffusibility, so that even when the exit pupil images 6L and 6R have a small diameter as shown in FIG. 1, it is possible to magnify them to exit pupil images 60L and 60R. If, at this time, the magnifying rate is properly determined, it is then possible to obtain exit pupil images 60L and 60R of easy-to-view size. Consequently, even when the eyes EL and ER of the viewer are slightly displaced from the exit pupil images 6L and 6R, it is possible to view the projected images 3L and 3R as images under observation. It is thus possible to provide a view-friendly projection viewing system.

It is here noted that both the eyepiece optical system 4 and the diffusing plate 5 are located in the vicinity of the images 3L and 3R projected through the projection optical systems 2L and 2R (at the given first position). Thus, the diffusing plate 5 could be designed by forming a diffusing surface having a diffusing action on at least one surface of the eyepiece optical system 4 as an integral piece. Alternatively, the diffusing plate 5 could be provided separately from the eyepiece optical system 4.

Preferably, the diffusing plate 5 should have an angle of diffusion of up to 20° at full width half maximum. As the angle of diffusion of the diffusing plate 5 at full width half maximum is greater than 20°, the angle of diffusion becomes too large. In this case, the image under observation becomes dark although the viewing field becomes large. This causes an increase in the bulkiness of an illumination unit for illuminating the object to be observed. When a bilaterally identical image is observed with both eyes as shown in FIG. 1, the angle of diffusion should preferably be up to 20° at full width half maximum as already mentioned. An angle of diffusion greater than that makes an image under observation dark.

More preferably, the diffusing plate 5 should have an angle of diffusion of at least 10° at full width half maximum. It is thus possible to obtain an easy-to-observe projection viewing system that enables images to be observed with both eyes EL and ER.

Figure 2:
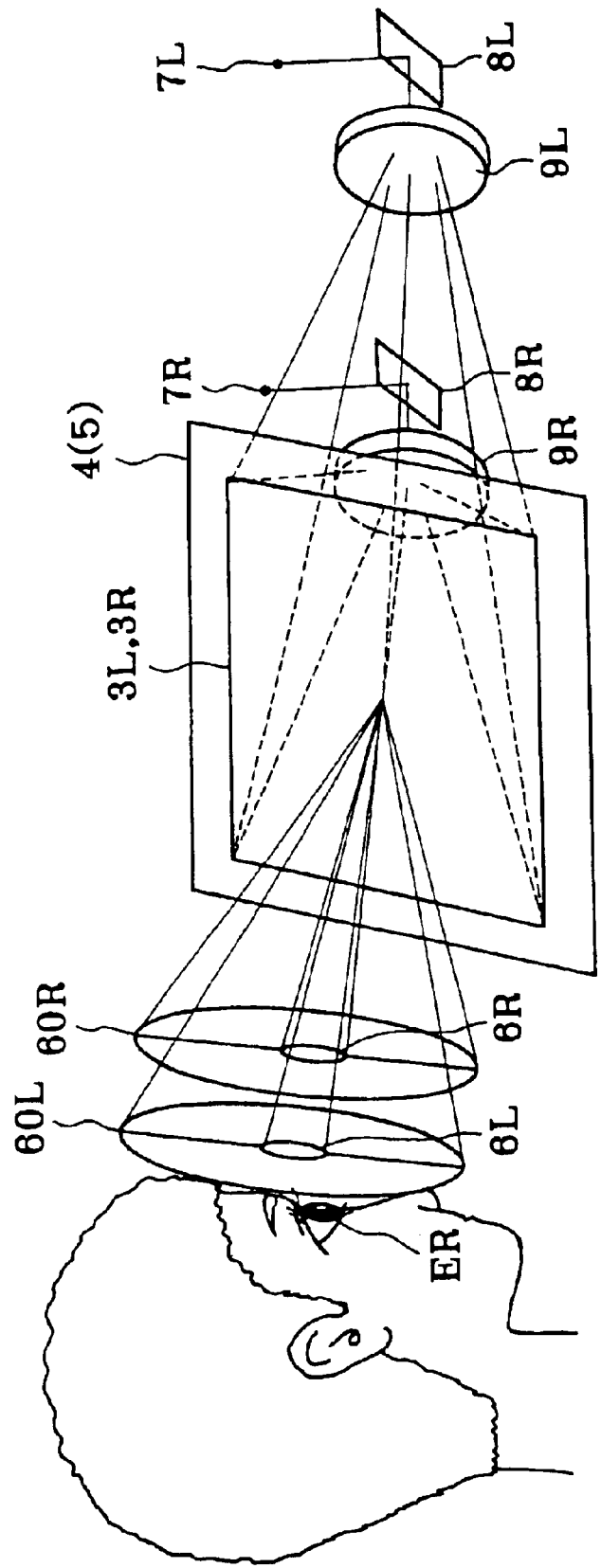
FIG. 2 is illustrative in conception of the optical system in the second projection viewing system according to the invention.

FIG. 2 is illustrative in conception of the second projection viewing system according to the invention. This projection viewing system, too, is designed to display projected images 3L and 3R for the left eye EL and the right eye ER simultaneously on a single display plane. The system could be designed to display an image for either one eye.

In the embodiment of FIG. 2, two light sources 7L and 7R are provided for both eyes. Light beams from the light sources 7L and 7R are deflected upon incidence on left and right scanning means 8L and 8R, respectively. Entering projection optical systems 9L and 9R, the deflected light beams are focused at a given first position at which the projected images 3L and 3R corresponding to the scanning patterns are formed. In this case, too, the projected images 3L and 3R could be each a bilaterally different image or a bilaterally identical image with or without binocular parallax. The projected images 3L and 3R should be formed while completely superposed on each other; however, some misalignment is acceptable. It is here noted that an eyepiece optical system 4 is located in the vicinity of the projected images 3L and 3R.

The scanning means 8L and 8R provide two-dimensional deflection of the light beams from the light sources. For the scanning means 8L and 8R, such arrangements as set forth in Patent Publications 4 and 3 could be used. For instance, there is a single two-dimensional scanning mirror as disclosed in Patent Publication 4, that is, a mirror of the gimbal structure. Alternatively, there is a combination of two deflecting mirrors that deflect light beams in mutually orthogonal directions, as disclosed in Patent Publication 3.

In the arrangement of FIG. 2, too, the eyepiece optical system 4 projects the exit pupils of projection optical systems 9L and 9R onto the viewer side. The projected exit pupils of the projection optical systems 9L and 9R (hereinafter referred to as the exit pupil images) are indicated at 6L and 6R. At the positions of the exit pupil images 6L and 6R the eyeballs EL and ER of the viewer are located. As a consequence, the eyepiece optical system 4 projects the exit pupils of the projection optical systems 9L and 9R onto the vicinity of the eyeballs EL and ER of the viewer. With such an eyepiece optical system 4, it is again possible to focus projection rays leaving the scanning means 8L and 8R, with efficiency, on the eyeballs EL and ER of the viewer. It is thus possible to view a bright image even when the light sources 7L and 7R of low output are used.

Further in the invention, a common single diffusing plate 5 is located in the vicinity of the projected images 3L and 3R. The diffusing plate 5 is then allowed to have given diffusibility, so that even when the exit pupil images 6L and 6R have a small diameter as shown in FIG. 2, it is possible to magnify them to exit pupil images 60L and 60R. If, at this time, the magnifying rate is properly determined, it is then possible to obtain exit pupil images 60L and 60R of easy-to-view size. Consequently, even when the eyes EL and ER of the viewer are slightly displaced from the exit pupil images 6L and 6R, it is possible to view the projected images 3L and 3R as images under observation. It is thus possible to provide a view-friendly projection viewing system.

It is here noted that both the eyepiece optical system 4 and the diffusing plate 5 are located in the vicinity of the projected images 3L and 3R formed through the scanning means 8L and 8R. Thus, the diffusing plate 5 could be designed by forming a diffusing surface having a diffusing action on at least one surface of the eyepiece optical system 4 as an integral piece. Alternatively, the diffusing plate 5 could be provided separately from the eyepiece optical system 4.

Preferably, the diffusing plate 5 should have an angle of diffusion of up to 20° at full width half maximum. As the angle of diffusion of the diffusing plate 5 at full width half maximum is greater than 20°, the angle of diffusion becomes too large. In this case, the image under observation becomes dark although the viewing field becomes large. This causes an increase in the bulkiness of an illumination unit for illuminating the object to be observed. When a bilaterally identical image is observed with both eyes as shown in FIG. 2, the angle of diffusion should preferably be up to 20° at full width half maximum as already mentioned. An angle of diffusion greater than that makes an image under observation dark.

More preferably, the diffusing plate 5 should have an angle of diffusion of at least 10° at full width half maximum. It is thus possible to obtain an easy-to-observe projection viewing system that enables images to be observed with both eyes EL and ER.

In the arrangements of FIGS. 1 and 2, suppose now that images with binocular parallaxes are observed as the left and right projected images 3L and 3R. In this case, a large angle of diffusion would cause cross talks because the images observed with both eyes differ. Then, those images could be seen as a double image rather than as a stereoscopic image. Therefore, the angle of diffusion of the diffusing plate 5 should preferably be at least 8° at full width half maximum.

At the full width where the intensity of light decreases to $\frac{1}{10}$, the diffusing plate 5 should preferably have an angle of diffusion of up to 12°. Satisfaction of the above condition leads to efficient utilization of illumination light because light rays diffusing at an angle of at least 12° are unlikely to reach the viewer. In this connection, the property of the diffusing plate should preferably be such that the intensity of diffused light drops sharply from full width half maximum.

The surface roughness of the diffusing plate 5 that ensures such an angle of diffusion as described above is now explained.

Figure 3:
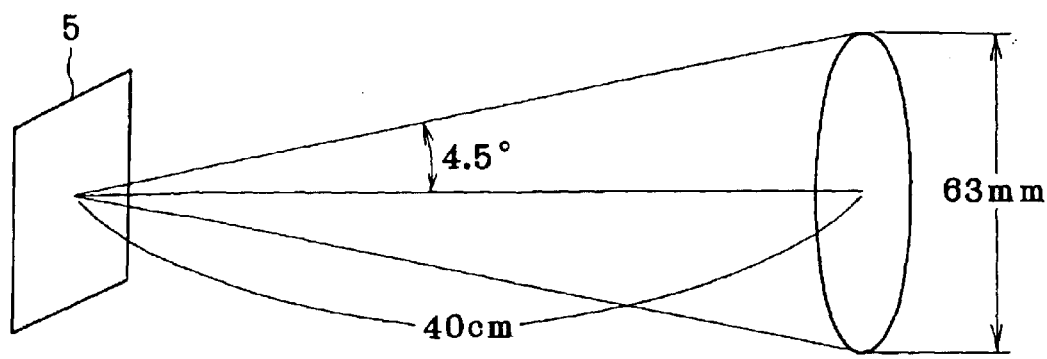
FIG. 3 is a schematic for finding the relation between the arithmetic mean roughness Ra and the mean pit-to-projection space Sm of the transmission type diffusing plate according to the invention.
Figure 4:
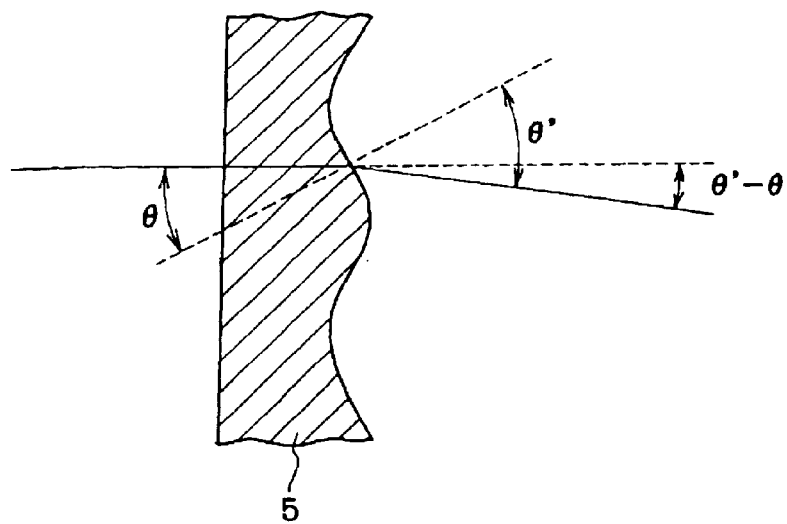
FIG. 4 is illustrative of the relation between the angle of incidence and the angle of refraction on the diffusing surface of the transmission type diffusing plate.

FIG. 3 is illustrative of the surface roughness of the diffusing plate 5 of the transmission type. Suppose now that a light ray is magnified to a $\phi 63$ mm size at a distance 40 cm away from the transmission type diffusing plate 5. Then, the angle of diffusion of the light ray must be 4.5 at half bandwidth. When light rays are refracted by fine pits and projections(convex-concave) on the surface of the diffusing plate 5, the pit-and-projection is assumed to be of sine wave shape and the diffusing surface to have a refractive index of 1.5. From $\theta'-\theta=4.5°$ where $\theta$ is the angle of incidence and $\theta'$ is the angle of refraction and Snell's formula, it is then found that the angle of incidence must have a gradient of about 8.86°, as shown in FIG. 4. It follows that the maximum value of the gradient of the surface roughness must be 8.86°.

Here the diffusing surface is assumed to be of smooth sine wave shape. Hence, the diffusing surface shape is expressed by $$y = a \times \sin(2\pi x/T)$$

where a is an amplitude and T is a period. Then, the gradient of the diffusing surface becomes (Gradient)=$dy/dx=a \times \cos(2\pi x/T) \times 2\pi/T$ At x=2πm (m is an integer) the gradient reaches a maximum. Hence, (Maximum value of gradient)=$a \times 2\pi/T$ It is thus possible to find a/T at which the maximum value of gradient is 8.86°.

(Maximum value of gradient)=$a/T \times 2\pi = 8.86/180 \times \pi = 0.154$

From this, one can obtain $a/T = 0.0246$

When the diffusing surface is of sine wave shape, the relation between the arithmetic mean roughness Ra according to JIS B0601 and a becomes $Ra/\sqrt{2} = a$ The relation between the pit-to-projection mean space Sm and the above period T becomes Sm=T From this, one can obtain the following result with respect to the surface roughness.

Sm=28.7Ra

In this case, the maximum gradient of the diffusing surface is 8.33°. At a refractive index of 1.5, a diffusing plate having a half angle of diffusion of 4.5° and a total angle of diffusion of 9° with respect to light rays is obtained.

Figure 5:
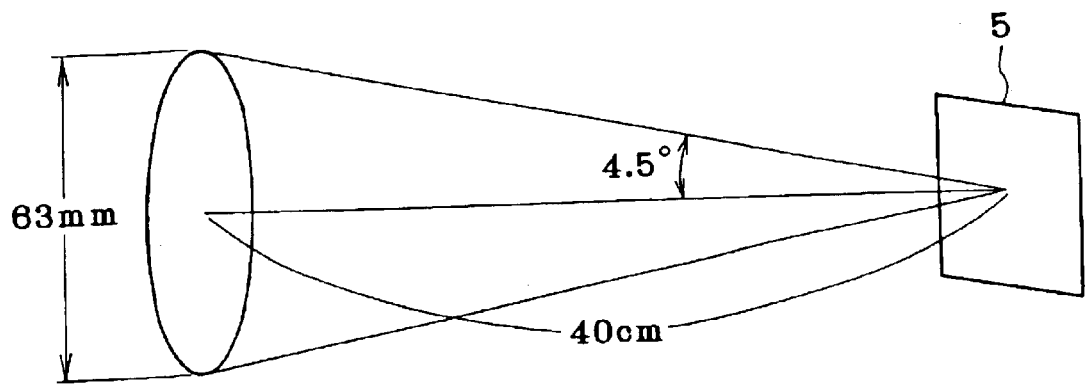
FIG. 5 is a schematic for finding the relation between the arithmetic mean roughness Ra and the mean pit-to-projection space Sm of the reflection type diffusing plate according to the invention.
Figure 6:
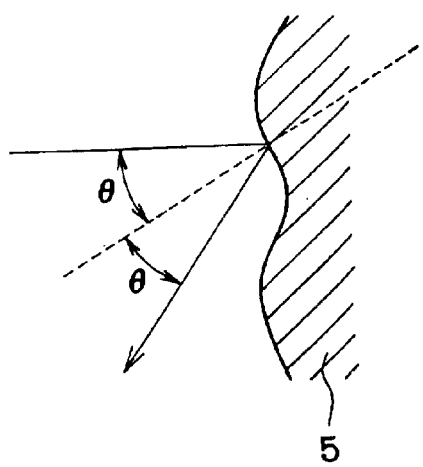
FIG. 6 is illustrative of the relation between the angle of incidence and the angle of refraction on the diffusing surface of the reflection type diffusing plate.

FIG. 5 is illustrative of the surface roughness of the diffusing plate 5 of the reflection type. Suppose now that a light ray is magnified to a ϕ63 mm size at a distance 40 cm away from the reflection type diffusing plate 5. Then, the angle of diffusion of the light ray must be 4.5° at half bandwidth. When light rays are reflected by fine pits and projections on the surface of the diffusing plate 5, the pit-and-projection is assumed to be of sine wave shape and the diffusing surface to have a refractive index of 1.5. In this case, the angles of incidence and reflection are given by θ, as shown in FIG. 6. From 2θ=4.5°, it is then found that the angle of incidence θ must have a gradient of about 2.25° that is about half of 4.5°, as shown in FIG. 6. It follows that the maximum value of the gradient of the surface roughness must be 2.25°. Here the diffusing surface is assumed to be of smooth sine wave shape. Hence, the diffusing surface shape is expressed by $y = a \times \sin(2\pi x/T)$ Then, the gradient of the diffusing surface becomes (Gradient)=$dy/dx = a \times \cos(2\pi x/T) \times 2\pi/T$ At x=2πm (m is an integer) the gradient reaches a maximum. Hence, (Maximum value of gradient)=$a \times 2\pi/T$ It is thus possible to find a/T at which the maximum value of gradient becomes 2.25°.

(Maximum value of gradient)=$a/T \times 2\pi = 2.25/180 \times \pi = 0.03927$

From this, one can obtain $a/T = 0.00625$

When the diffusing surface is of sine wave shape, the relation between the arithmetic mean roughness Ra according to JIS B0601 and a becomes $Ra/\sqrt{2} = a$ The relation between the pit-to-projection mean space Sm and the above period T becomes Sm=T From this, one can obtain the following result with respect to the surface roughness.

Sm=113.14Ra

In this case, the maximum gradient of the diffusing surface becomes 2.25°, giving a diffusing plate having a half angle of diffusion of 4.5° by reflection and a total angle of diffusion of 9°.

Figure 7:
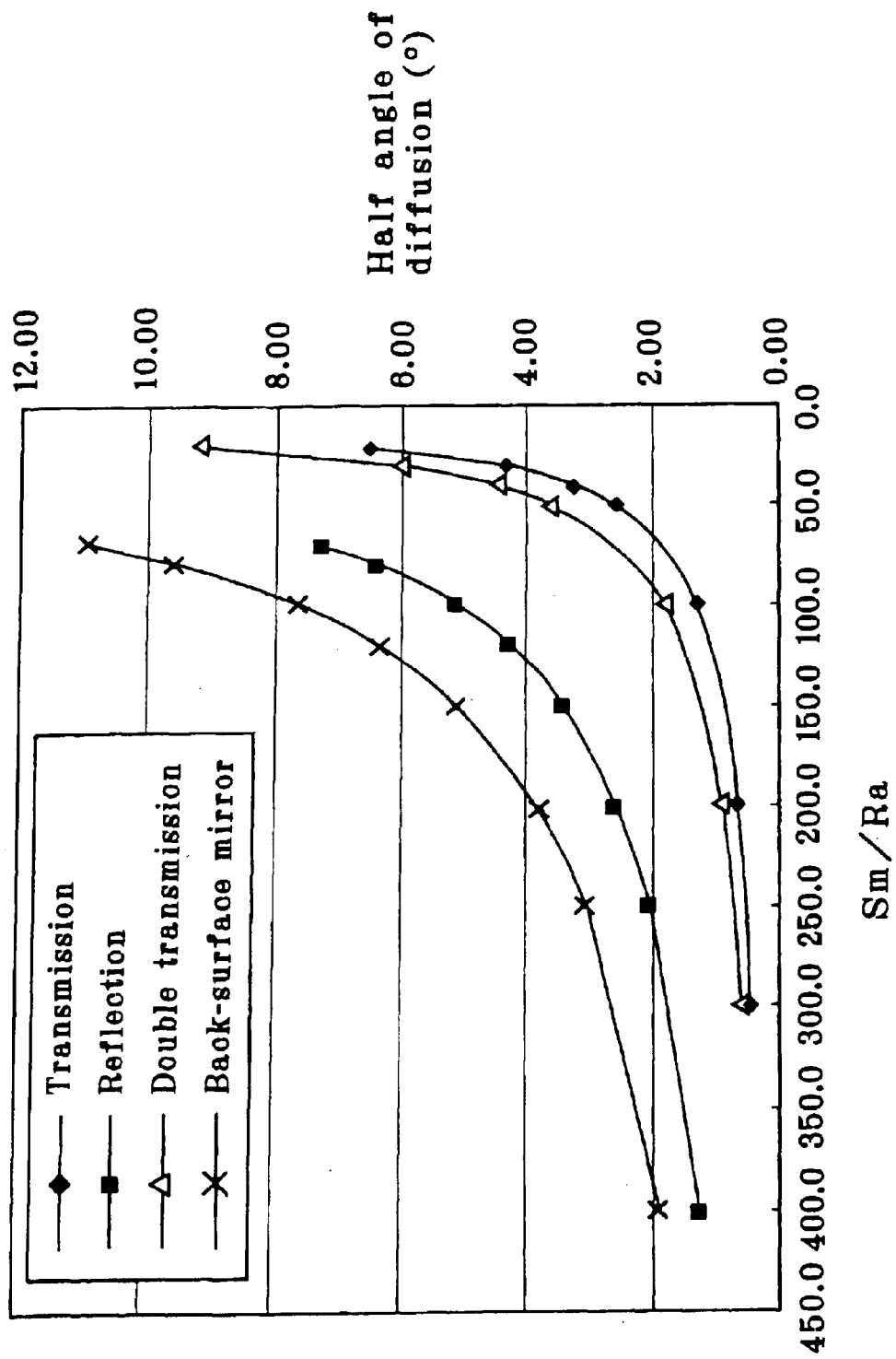
FIG. 7 is illustrative of the relation between Sm/Ra and the half angle of diffusion of the diffusing plate according to the invention.

This is extended to a double-transmission type diffusing plate and a back-surface mirror type diffusing plate. The relations between Sm/Ra and the half angle of diffusion are illustrated in FIG. 7. Here the pit-and-projection surface of the diffusing surface is assumed to be approximate to the sine wave shape.

From such findings as described above, the surface roughness of the diffusing plate 5 should preferably satisfy the following condition (1).

$$5 < (Sm/Ra) < 1,000 \qquad (1)$$

This condition is required to impart preferable diffusibility to the diffusing plate 5. Here the diffusibility is given to the diffusing plate 5 via the fine surface pit-and-projection shape. It is preferable to diffuse light rays by the fine surface pit-and-projection shape of the diffusing plate 5, because the diffusibility is little dependent on wavelength. Reflection of light rays occurs only through Fresnel reflection at the surface of the diffusing plate 5. This diffusion method is much improved in terms of transmittance drop than other diffusion methods. If an AR (antireflection) coat or the like is applied on the diffusing plate 5, it is then possible to obtain further transmittance improvements.

More preferably, $$10 < (Sm/Ra) < 500 \qquad (1\text{-}1)$$

The diffusing surface of the diffusing plate 5 according to the present invention should preferably have a random pit-and-projection shape in such a way as to satisfy the following conditions. This makes it possible to obtain scintillation-free, clear, bright images with a large exit pupil diameter.

Preferably for the single transmission type diffusing plate, $$5 < (Sm/Ra) \times (Ep/400) < 70 \qquad (2)$$

Preferably for the double-transmission type diffusing plate, $$10 < (Sm/Ra) \times (Ep/400) < 80 \qquad (3)$$

Preferably for the front-surface reflection type diffusing plate, $$50 < (Sm/Ra) \times (Ep/400) < 200 \qquad (4)$$

Preferably for the back-surface reflection type diffusing plate, $$80 < (Sm/Ra) \times (Ep/400) < 250 \quad (5)$$

Here Sm is a mean pit-to-projection space of the surface according to JIS B0601 (μm), Ra is a center-line mean roughness of the surface (μm), and EP is a distance from the diffusing surface to the position of a viewer's eye (an eye point (mm)).

As the lower limits to conditions (2) to (5) are not reached, the angle of diffusion becomes too small to obtain any large pupil diameter. As the upper limits are exceeded, the diffusion of light becomes too large and so an image under observation becomes dark.

It is noted that when a Fresnel lens is used for the eyepiece optical system 4, it is more preferable to make the pit-and-projection shape of the diffusing surface random. A pit-and-projection shape having periodicity causes moiré fringes between the pitch of the lens and the diffusing surface, which are then superposed on an image under observation. As a result, the image becomes difficult to see.

More preferably for the single transmission type diffusing plate, $$10 < (Sm/Ra) \times (Ep/400) < 40 \quad (2\text{-}1)$$

More preferably for the double-transmission type diffusing plate, $$15 < (Sm/Ra) \times (Ep/400) < 60 \quad (3\text{-}1)$$

More preferably for the front-surface reflection type diffusing plate, $$70 < (Sm/Ra) \times (Ep/400) < 150 \quad (4\text{-}1)$$

More preferably for the back-surface reflection type diffusing plate, $$100 < (Sm/Ra) \times (Ep/400) < 200 \quad (5\text{-}1)$$

Further, the present invention should preferably satisfy condition (6) with respect to the pit-to-projection mean space of the diffusing surface of the diffusing plate.

$$Sm < 200 \ \mu m \quad (6)$$

This condition (6) concerns the scintillation of a viewing screen. In the projection viewing system of the present invention in particular, a narrow light beam (having a small NA) is emitted from the projection optical system 2, 21, 22. Then, this narrow light beam is used to form a projection image in the vicinity of the diffusing plate 5. At this time, the magnitude of Sm has some significant influence on the scintillation of an image. For the diffusing surface, therefore, it is of importance to satisfy the present condition (6) while satisfying conditions (1) to (5).

Reference is then made to what happens when this condition (6) is not satisfied, i.e., Sm is not smaller than 200 μm. In severe cases, as the observer moves his eyes, the whole screen looks as if it blinked slightly. In other words, scintillation is visible. In less severe cases, the image lacks clearness. For instance, the image (the angle of view) looks like an image projected onto ground glass. As a result, it is impossible to view any vivid image.

More preferably, $$Sm < 100 \ \mu m \quad (6\text{-}1)$$

Even more preferably, $$Sm < 50 \ \mu m \quad (6\text{-}2)$$

For instance, the diffusing plate 5 of the present invention that satisfies such conditions as set forth above is disclosed in Japanese Patent Application No. 2001-370950 filed by the present applicant. This publication discloses how to fabricate diffusing plates. In the present invention, diffusing plates fabricated by such a method could be used. For instance:

(1) A diffusing plate fabricated by sandblasting. Spherical beads having limited diameters are blown onto a substrate, so that a group of concave facets or a group of facets similar to such facets or convex facets complementary to such facets can be formed on the surface of the substrate. In these groups, the facets are at random, defining a diffusing surface. In this way, the diffusing plate is fabricated.

(2) A diffusing plate fabricated by sandblasting plus copying. Spherical beads are blown onto a metal substrate to form a group of randomly arranged concave facets. This metal substrate is used as a master to copy the group of randomly arranged convex facets to a transparent substrate, so that a diffusing plate can be fabricated.

(3) A diffusing plate fabricated by sandblasting plus transfer. First, a metal substrate is provided with a layer. Then, spherical beads are blown onto the layer on the metal substrate to form a group of randomly arranged concave facets. Subsequently, the group of randomly arranged concave facets formed on the layer is similarly transferred onto the surface of the metal substrate. Finally, the metal substrate is used as a master to copy the group of randomly arranged concave facets to a transparent substrate, so that a diffusing plate can be fabricated.

(4) In the diffusing plate (1), (2) or (3), glass beads having a diameter of 0.01 mm to 2 mm are used as the spherical beads.

(5) In the diffusing plate (1), (2), (3) or (4), the spherical beads are blown at a pneumatic pressure of 0.5 to 3.0 kg/cm$^2$.

(6) In the diffusing plate according to any one of (1) to (5), the metal substrate is a brazen substrate.

(7) In the diffusing plate according to any one of (1) to (6), the metal substrate is formed of a metal whose hardness is higher than that of the spherical beads.

(8) In the diffusing plate according to any one of (2) to (7), injection molding or press molding is used to copy the group of concave facets formed on the surface of the metal substrate to the transparent substrate.

(9) A diffusing plate fabricated by a method wherein resin droplets are sprayed onto a substrate to form a group of randomly arranged convex facets, and the group of randomly arranged convex facets is similarly transferred onto the substrate side (the surface of the substrate) or a group of concave facets complementary to the group of convex facets is transferred onto the substrate side (the surface of the substrate).

In addition, the diffusing plate set forth in Patent Publication 5, too, could be used. This diffusing substrate is fabricated by roughening one or both sides of a transparent substrate. One or both sides of the transparent substrate, for instance, could be roughened by the following methods (1) to (4).

(1) Etching; that is, one or both sides of the transparent substrate is etched.

(2) Coating or printing; that is, a resin or filler is provided on one or both side of the transparent substrate in a single layer or multilayer form by means of coating or printing. If required, a painting material or ink dispersed in water or an organic solvent is used.

(3) Electrostatic or electrodepositing coating of powders; that is, a resin or filler or their mixture is provided on one or both sides of the transparent substrate by means of electrostatic or electrodepositing coating.

(4) Film formation by extrusion molding, injection molding or the like; that is, an organic or inorganic filler together with a resin is melted with the application of heat and pressure, and the melt is formed into a film by extrusion molding, injection molding or the like. The resulting diffusing plate should preferably have a HAZE value (JIS K7105) in the range of 10 to 40.

Furthermore, the diffusing plate fabricated according to Patent Publication 6, too, could be used. This method of fabricating a diffusing plate comprises the steps of laminating a binder layer directly or via an additional layer on a substrate, embedding a filler into the binder layer by means of a pressurizing medium, and removing extra filler deposited onto the laminate.

As already described, the eyepiece optical system 4 should preferably be constructed of a Fresnel surface represented by a Fresnel lens or mirror. The eyepiece optical system 4 could also be constructed of a decentered Fresnel reflecting surface. If the eyepiece optical system 4 is formed of the Fresnel surface, then it can be slimmed down. As a result, the projection viewing system can be made compact and easily foldable. As exemplified in the examples given later, the eyepiece optical system may be constructed of one concave mirror.

Further, the eyepiece optical system 4 could be constructed of a catoptric system that functions well to reduce aberrations produced at the exit pupils (exit pupil images) of the projection optical systems (2L, 2R or 9L, 9R) projected on the viewer side. This ensures a wide field of view without enhancing the diffusibility of the diffusing plate 5. In addition, the quantity of light diffusing in unnecessary directions is so reduced that an image under observation becomes bright without increasing the quantity of illumination light. Especially in an optical system wherein the optical axis of the eyepiece optical system 4 is decentered as contemplated herein, there are some considerable decentration aberrations. Moreover, when the eyepiece optical system 4 is of simple construction, it is difficult to provide another surface for correction of such decentration aberrations. In this regard, it is preferable to rely on a catoptric system with reduced decentration aberrations.

Constructed of the Fresnel surface, the eyepiece optical system 4 can be slimmed down, because of being defined by a substantial plane. In a reflection type Fresnel surface, the surface of optical action is defined by a zonal reflecting surface. The angle of the zonal reflecting surface subtending a surface vertical to the optical axis is smaller than that of a refraction type Fresnel surface (a Fresnel lens). With the reflection type Fresnel surface, therefore, there is a reduction of ghost light produced at a Fresnel end face (an inactive surface), which is a problem with the Fresnel lens, and the transmittance efficiency for light rays can be increased as well. The use of the reflection type Fresnel surface is particularly desired when the angles of two optical axes determined by the scanning means $8_1$ and $8_2$ are large, as described later.

Figure 8:
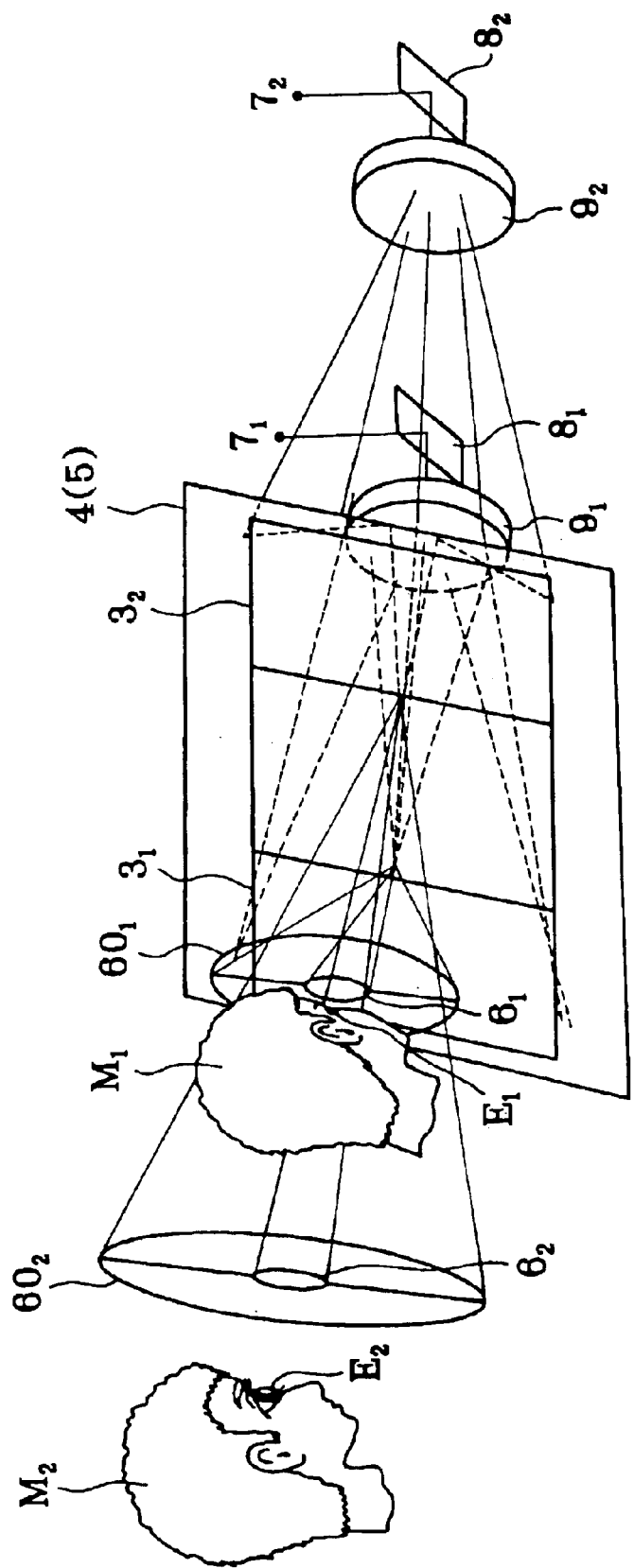
FIG. 8 is illustrative in conception of the third projection viewing system according to the invention.

FIG. 8 is illustrative in conception of an optical system in the third projection viewing system according to the present invention. The third projection viewing system of the present invention is designed such that a plurality of viewers can simultaneously view an image from varying directions. As in FIG. 2, the projection viewing system shown in FIG. 8 comprises two light sources $7_1$ and $7_2$, two scanning means $8_1$ and $8_2$, and two projection optical systems $9_1$ and $9_2$, so that projected images $3_1$ and $3_2$ are formed in the vicinity of an eyepiece optical system 4 and a diffusing plate 5. The projection viewing system is also designed such that two images are projected onto the eyes $E_1$ and $E_2$ of different viewers $M_1$ and $M_2$. In FIG. 8, the exit pupils of the projection optical systems $9_1$ and $9_2$ projected via the eyepiece optical system 4, viz., exit pupil images are indicated at $6_1$ and $6_2$, and the exit pupil images magnified by the diffusing plate 5 are indicated at $60_1$, and $60_2$. It is noted that such a projection viewing system as depicted in FIG. 1, i.e., a projection viewing system comprising two display devices and two projection optical systems, too, could be constructed in much the same manner.

The projected images $3_1$ and $3_2$ formed in the vicinity of the eyepiece optical system 4 are such that, as shown in FIG. 8, they at least overlap each other. This makes it possible to display different images even on a limited extent display plane. It is noted that this display plane is constructed of the eyepiece optical system 4 and the diffusing plate 5.

In the arrangement of FIG. 8, the optical axes from the scanning means $8_1$ and $8_2$ to the eyepiece optical system 4 via the projection optical systems $9_1$ and $9_2$ cross the eyepiece optical system 4. It is then preferable that at a point where either one of the optical axes intersects the eyepiece optical system 4, the angle of a perpendicular to the eyepiece optical system 4 that subtends that optical axis is at least 10°. This is now explained with reference to FIG. 9.

Figure 9:
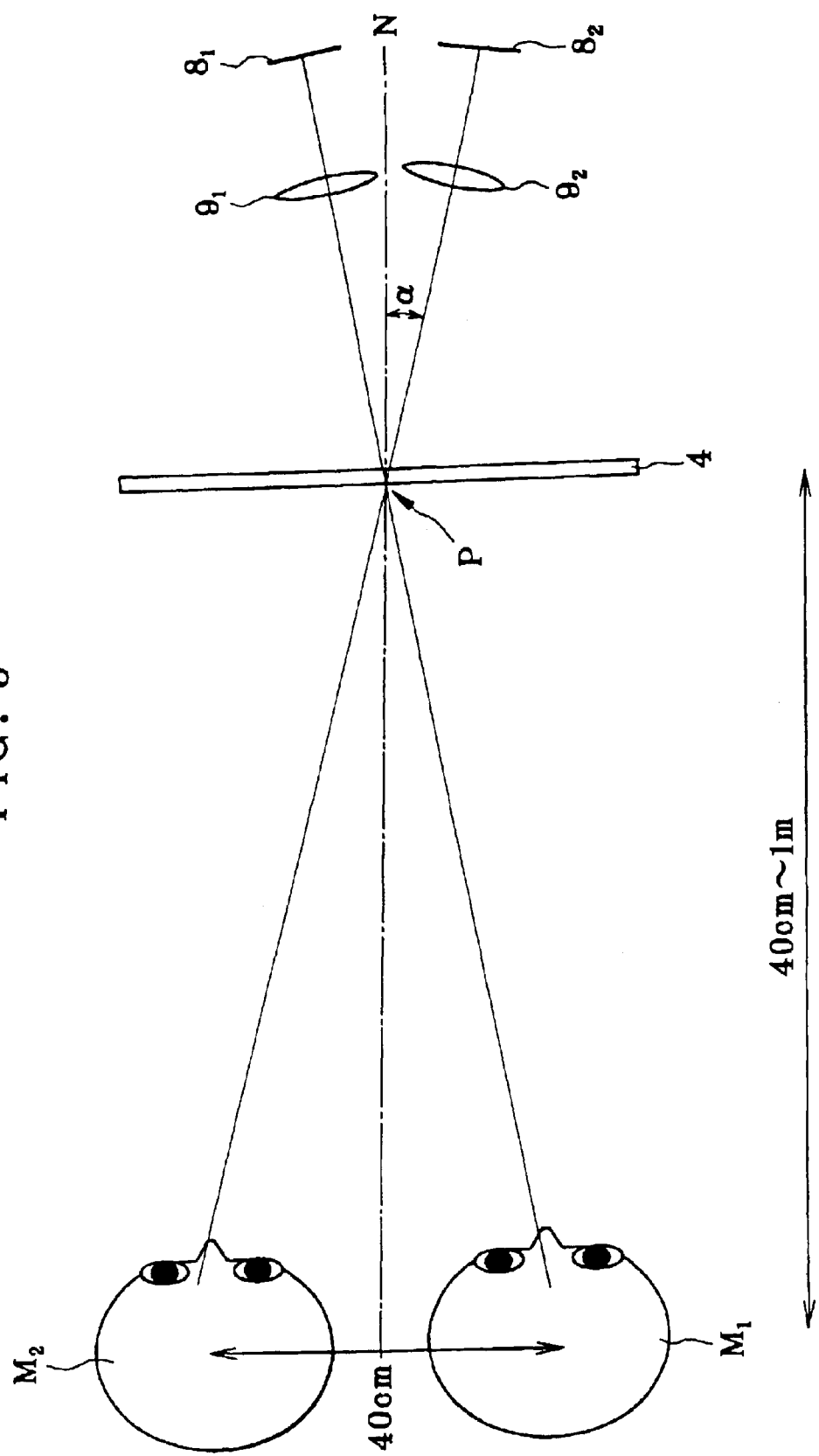
FIG. 9 is illustrative of the angle that the optical axis of the projection optical system, which is two-dimensionally decentered, makes with the perpendicular of the eyepiece optical system.

As shown in FIG. 9, the optical axes of the scanning means $8_1$ and $8_2$ to the eyepiece optical system 4 via the projection optical systems $9_1$ and $9_2$ pass through substantially the centers of the diffusing plate 5 and the eyepiece optical system 4, arriving at the positions of the eyeballs of the viewers $M_1$ and $M_2$. It is here understood that the diffusing action of the diffusing plate 5 is not taken into account.

The projection viewing system of the present invention has a possible application as a personal display. The personal display is designed such that at least two viewers can view an image formed on a single display plane from different directions. In this case, the distance between the display plane and the viewers is about 40 cm to about 1 m. Upon viewing, the faces of two or more viewers, for instance two viewers $M_1$ and $M_2$ are unlikely to be close to each other. In other words, the facial centers of both would be spaced at least 40 cm away from each other. In this case, the angle that the optical axis of the projection optical system $9_1$ subtends that of the projection optical system $9_2$ is in the range of 53° to 22.6°. In view of psychological factors of both faces being close to each other, the angle α that a perpendicular N to the eyepiece optical system 4 subtends either one of the optical axes of the projection optical systems $9_1$ and $9_2$ (the optical axes that enter from the scanning means $8_1$ and $8_2$ into the eyepiece optical system 4 via the projection optical systems $9_1$ and $9_2$) at a point P should preferably be at least 10°. Here the point P is located where at least either one of the optical axes of the projection optical systems $9_1$ and $9_2$ intersects the eyepiece optical system 4. It is noted that the perpendicular N to the eyepiece optical system 4 is to the major surface of the eyepiece optical system. It is also noted that when the eyepiece optical system 4 is constructed of a Fresnel lens or reflecting mirror, the perpendicular is defined to that Fresnel lens or reflecting mirror.

Figure 10:
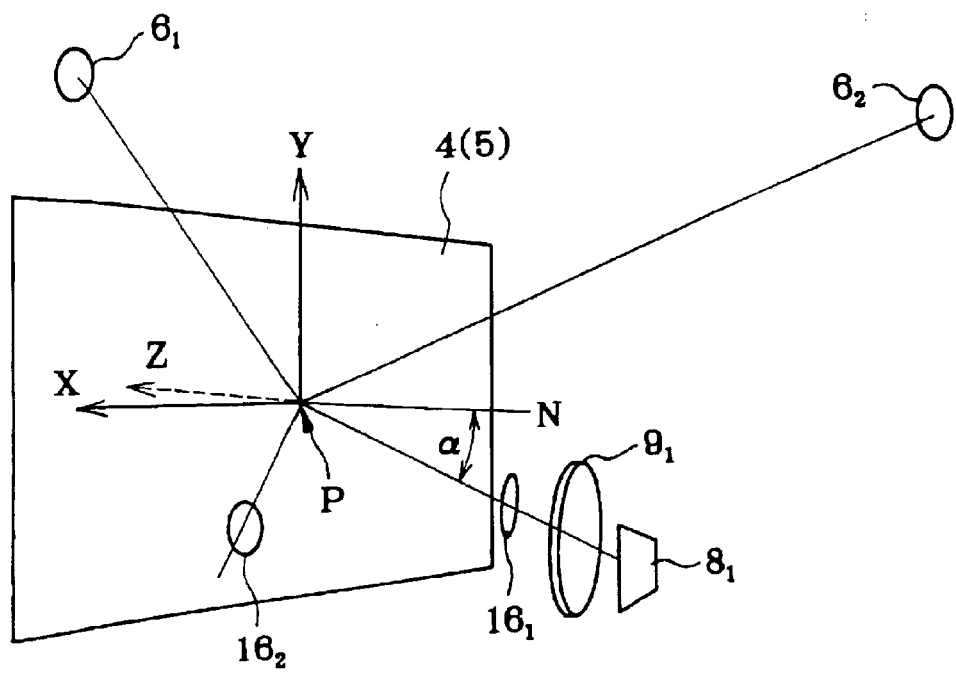
FIG. 10 is similar to FIG. 9, showing the case wherein the projection optical system is three-dimensionally decentered.

FIG. 9 illustrates an arrangement wherein the scanning means $8_1$ and $8_2$ and the projection optical systems $9_1$ and $9_2$ are located in a two-dimensionally decentered manner. The same holds true for the case where they are three-dimensionally located. FIG. 10 is illustrative in schematic of an arrangement where the scanning means $8_1$ and $8_2$ and the projection optical systems $9_1$ and $9_2$ are located in a three-dimensionally decentered manner. It is noted that only one scanning means $8_1$ and only one projection optical system $9_1$ are shown in FIG. 10. The exit pupils of the projection optical systems $9_1$ and $9_2$ are indicated by $16_1$ and $16_2$, respectively, and exit pupil images by $6_1$ and $6_2$, respectively. Here the exit pupil images $6_1$ and $6_2$ are projected images upon projection of the exit pupils $16_1$ and $16_2$ through the eyepiece optical system 4.

When the projection optical systems $9_1$ and $9_2$ are three-dimensionally located as shown in FIG. 10, too, it is desired that the angle α that the perpendicular N intersects the projection optical systems $9_1$ and $9_2$ at the point N is at least 10°, as in FIG. 9.

In the present invention, too, it is desired that the angle of diffusion of the diffusing plate 5 is up to 20° at full width half maximum. This diffusibility is imparted to the diffusing plate 5 thereby making it possible for the viewers to view separate projected images $3_1$ and $3_2$. At an angle of diffusion exceeding the upper limit of 20°, on the one hand, the projected images $3_1$ and $3_2$, if they are different from each other, cause a "cross talk" where the different images look in an overlapping manner. This makes it impossible for the viewers to have a proper observation of what is displayed. As the upper limit of 20° is exceeded, on the other hand, the angle of diffusion becomes too large and so an image under observation becomes dark; to ensure the necessary quantity of light, light sources $7_1$ and $7_2$ must be bulky. It is noted that when the projected images $3_1$ and $3_2$ are the same, there is no "cross talk" problem.

The diffusibility of the diffusing plate should preferably be such that the angle of diffusion is up to 40° at a ⅒ full width. Light rays diffusing at an angle of at least 40° do not reach the viewers. By satisfaction of this condition, unnecessary illumination light decreases with an improvement in the efficiency of utilization of illumination light. As a result, light sources of small size and low output can be used as the light sources $7_1$ and $7_2$. The diffusibility of the diffusing plate should also preferably be such that the intensity of diffused light drops sharply from full width half maximum.

Furthermore, the diffusibility of the diffusing plate 5 should preferably be such that the angle of diffusion is up to 30° at a ⅒ full width. Light rays diffusing at an angle of diffusion of at least 30° hardly reach the viewers, and so satisfaction of this condition could lead to the efficient utilization of illumination. The diffusibility of the diffusing plate should also preferably be such that the intensity of diffused light drops sharply from full width half maximum.

In the arrangements of FIGS. 9 and 10, the images scanned by the scanning means 81 and 82 are projected from oblique directions. When, in this case, the projection optical systems $9_1$ and $9_2$ are each constructed of a rotationally symmetric optical system, the projected images are tilted to cause an image distortion. This image distortion can be corrected by parallel location of the display plane formed by scanning by the scanning means $8_1$ and $8_2$, the major surfaces of the projection optical systems $9_1$ and $9_2$ and the major surface of the eyepiece optical system 4 and shifting of the projection optical systems $9_1$ and $9_2$ vertically to the optical axis, as shown in FIG. 10. Alternatively, the image distortion may be corrected by locating these three members in such a way as to satisfy Shymfluk law.

Still alternatively, such an image distortion could be corrected in an electrical fashion. In this case, the images formed by the scanning means $8_1$ and $8_2$ are previously distorted while allowing for electrical cancellation of that image distortion. Of course, it is acceptable to make use of both the optical correction method and the electrical correction method.

A decentered optical system should preferably be used as each of the projection optical systems $9_1$ and $9_2$. Preferably in this case, each projection optical system $9_1$, $9_2$ should have a rotationally asymmetric surface. Preferably but not exclusively, a free-form surface is used as the rotationally asymmetric surface. The free-form surface, for instance, is defined by formula (a) set forth in Patent Publication 7 (Patent Publication 8), wherein the Z-axis is the axis of the free-form surface.

At least one of the projection optical systems $9_1$ and $9_2$ is constructed of a decentered prism optical system. The decentered prism optical system comprises at least one decentered prism formed of a medium having a refractive index of greater than 1 (n>1). The decentered prism has an entrance surface for entering a light beam in the prism, at least one reflecting surface for reflecting the light beam in the prism and an exit surface through which the light beam leaves the prism. It is noted that the light beam entering the entrance surface is emanated from the scanning means or the display device.

The at least one reflecting surface of the decentered prism should preferably have a curved surface shape to give power to a light beam, wherein the curved surface shape is defined by a rotationally asymmetric surface shape capable of correcting decentration aberrations. This ensures that the ability to correct an image distortion is much improved. This is particularly preferable for the case where the optical axes of at least two projection optical systems $9_1$ and $9_2$ make an angle of at least 30°.

Figure 11:
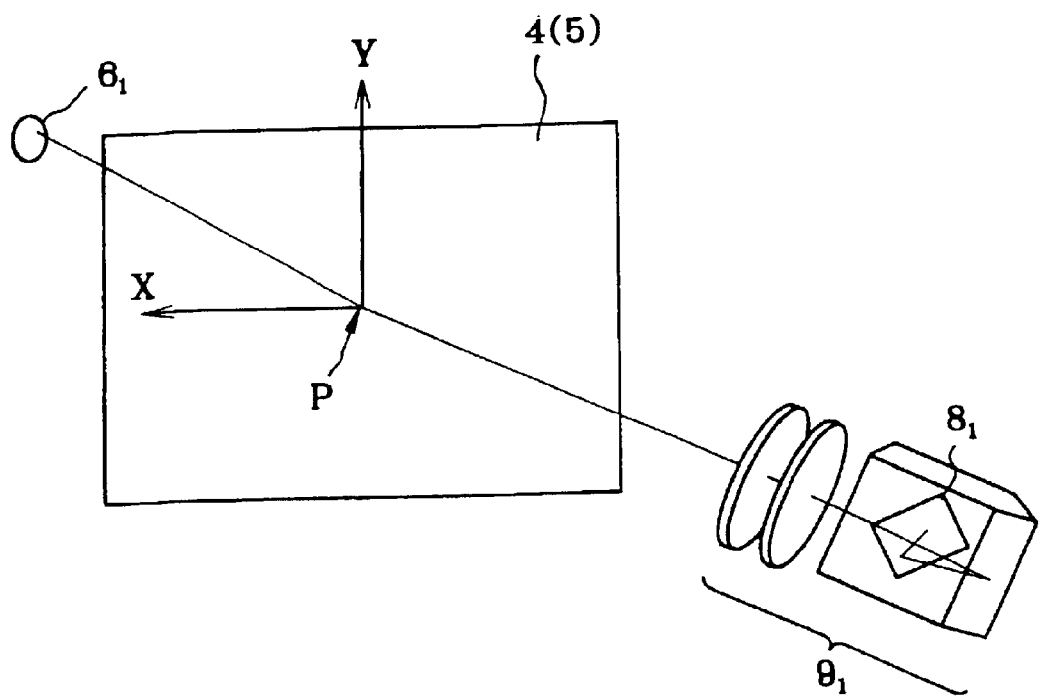
FIG. 11 is illustrative in schematic of the projection type optical system comprising a combination of a rotationally symmetric lens system and a decentered prism.

It is noted that the decentered prism optical system used as the projection optical system $9_1$, $9_2$ may comprise one or more decentered prisms. Alternatively, it is acceptable to use a combined rotationally symmetric lens system and decentered prism, as schematically shown in FIG. 11.

One example of the decentered prism has the following construction and features; that is, it comprises:

an entrance surface for entering light beams from the scanning means $8_1$ and $8_2$ in the prism, a first reflecting surface for reflecting the light beams entering the prism through the entrance surface in the prism, a second reflecting surface for reflecting the light beams reflected at the first reflecting surface in the prism, and an exit surface through which the light beams reflected at the second reflecting surface leaves the prism, wherein:

the entrance surface, the first and second reflecting surface and the exit surface are arranged such that the light beams from the entrance surface toward the first reflecting surface and the light beams from the second reflecting surface toward the exit surface intersect in the prism, and at least one of the entrance surface, the first and second reflecting surfaces and the exit surface comprises a rotationally asymmetric surface.

The use of such a decentered prism ensures that the optical path through the prism crosses over itself to make the angle of incidence of light on the reflecting surfaces (the first and second reflecting surfaces) small. As a result, the amount of decentration aberrations produced is reduced.

Another example of the decentered prism used for the projection optical system $9_1$, $9_2$ has the following construction and features; that is, it comprises:

an entrance surface for entering light beams from the scanning means $8_1$ and $8_2$ in the prism, a first reflecting surface for reflecting the light beams entering the prism through the entrance surface in the prism, a second reflecting surface for reflecting the light beams reflected at the first reflecting surface in the prism, and an exit surface through which the light beams reflected at the second reflecting surface leaves the prism, wherein:

the entrance surface and the second reflecting surface are defined by a single surface.

The decentered prism of the type that combines the second reflecting surface with the entrance surface allows a light ray to be largely flexed at the second reflecting surface. On the other hand, the first reflecting surface reflects the light ray toward the second reflecting surface at a small angle of flexion. With this decentered prism, it is thus possible to reduce the thickness of the prism optical system in the incident light ray direction.

The projection optical system $9_1$, $9_2$ constructed of such a decentered prism optical system has the following advantages. When images formed by the scanning means $8_1$ and $8_2$ are entered in the eyepiece optical system 4 from an oblique direction, the decentered prism optical system symmetric with respect to plane makes it easy to correct a distortion of a tilted image. An image distortion occurring in this oblique arrangement is of asymmetric shape as viewed from a given direction. However, this asymmetric shape is in agreement with the direction of occurrence of an asymmetric image distortion produced by the decentered prism optical system. It is thus possible to make correction for the image distortion by the decentration aberrations of the decentered prism optical system and, hence, make correction of aberrations easy. The "given direction" used herein is understood to refer to the plane-of-symmetry direction of the decentered prism optical system inclusive of a point P where the optical axis of the projection optical system $9_1$, $9_2$ intersects the eyepiece optical system 4.

In this case, too, such an image distortion could be corrected in an electrical manner. It is then noted that the images formed by the scanning means $8_1$ and $8_2$ are previously distorted, allowing for electrical cancellation of the image distortion. Of course, it is acceptable to rely on the above optical and electrical correction methods.

Suppose now that the projection optical system $9_1$, $9_2$ is constructed of the decentered prism optical system of shape symmetric with respect to plane. In this case, too, the angle that the perpendicular to the eyepiece optical system 4 subtends the (at least one) optical axis of the projection optical systems $9_1$ and $9_2$ at the point P must be at least 10° as already described.

A preferable arrangement for the decentered prism and the scanning means is now explained with reference to FIG. 11. In FIG. 11, P is a point of intersection of the optical axis of a decentered prism optical system $9_1$ with an eyepiece optical system 4. Having a plane of symmetry, the decentered prism optical system $9_1$ is located in such a way that the plane of symmetry includes the point P. A scanning means $8_1$ is provided on the entrance surface (object plane) side of the decentered prism optical system $9_1$. An image is formed by this scanning means $8_1$ in the vicinity of the eyepiece optical system 4. In this case, the scanning means $8_1$ is turned around the optical axis in such a way that the direction of movement of an image-forming light beam, i.e., the longitudinal or lateral scanning direction is substantially in line with the longitudinal or lateral direction of the eyepiece optical system 4. A decentered prism optical system $9_2$ and scanning means $8_2$, too, are located in the same manner.

By locating such scanning means $8_1$ and $8_2$ in this arrangement, a rotational asymmetric image distortion can be corrected with the decentered prism optical system of shape symmetrical with respect to plane. This rotationally asymmetrical image distortion is caused by the oblique location of the projection optical systems $9_1$ and $9_2$ with respect to the eyepiece optical system 4.

In the present invention, it is possible to provide the decentered prism optical systems of the same shape for both the projection optical systems $9_1$ and $9_2$. Thus, the fabrication cost of both the projection optical systems $9_1$ and $9_2$ can be much more reduced as compared with that of the projection optical systems $9_1$ and $9_2$ of varying shapes.

It is noted that such a two-dimensionally scanning mirror of the gimbal structure as set forth in Patent Publication 4 may be used as the scanning means $8_1$, $8_2$. It is then not always required to use the projection optical system $9_1$, $9_2$.

Referring again to the projection viewing systems of the constructions as shown in FIG. 1, FIG. 2 and FIGS. 8–11, diffusibility is primarily imparted to the diffusing plate 5 by a directional fine pit-and-projection surface or a roughened surface. However, a diffusing plate comprising a hologram could be used as the diffusing plate 5 for each projection viewing system. A transmission hologram and a reflection hologram would be used as possible hologram diffusing plates. Referring to a hologram recorded in a volume type photosensitive material, the transmission hologram is of low wavelength selectivity whereas the reflection hologram is of high wavelength selectivity. For a projection viewing system that presents color images, it is necessary to multi-record three hologram interference fringes, thereby diffusing light components of three R (red), G (green) and B (blue) wavelengths. For this reason, it is preferable to use a transmission hologram of relatively low wavelength selectivity as the hologram. For a projection viewing system of small size, it is preferable that a concave mirror (inclusive of a Fresnel concave reflecting mirror) as the eyepiece optical system is used in combination with a diffusing plate comprising such a transmission hologram. In the present disclosure, the diffusing plate comprising a transmission hologram will simply be called the diffusing plate.

The projection viewing system is now explained. For this projection viewing system, an eyepiece optical system comprising a concave mirror 24 and a diffusing plate 25 are used. For the diffusing plate 25, the transmission hologram is used. It is here noted that the display device, light sources and scanning means in the projection viewing system of this construction are not illustrated. As in FIGS. 1 and 2, etc., the eyepiece optical system is located on the entrance side of a projection optical system 2, 9. It is noted that only one of the left and right or a plurality of optical systems in the projection viewing system of this construction is now explained, and the rest is not referred to.

Figure 12A:
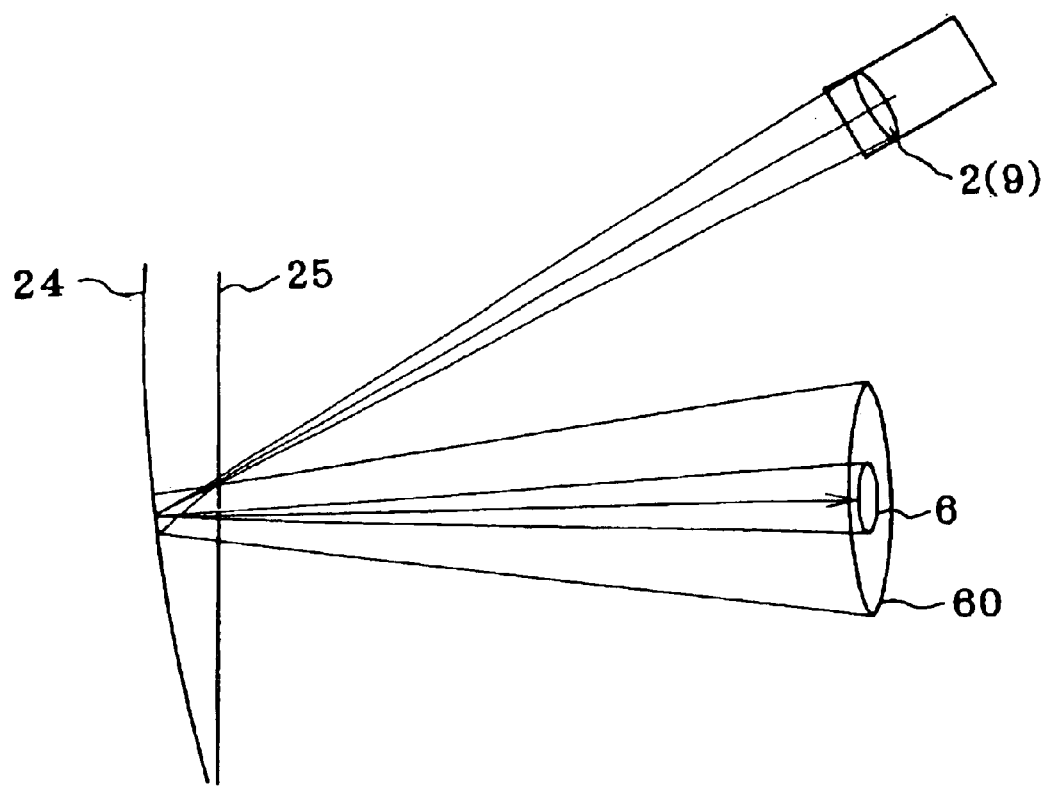
FIG. 12(a) is illustrative in conception of optical systems in the projection viewing system constructed according to the present invention.
Figure 12B:
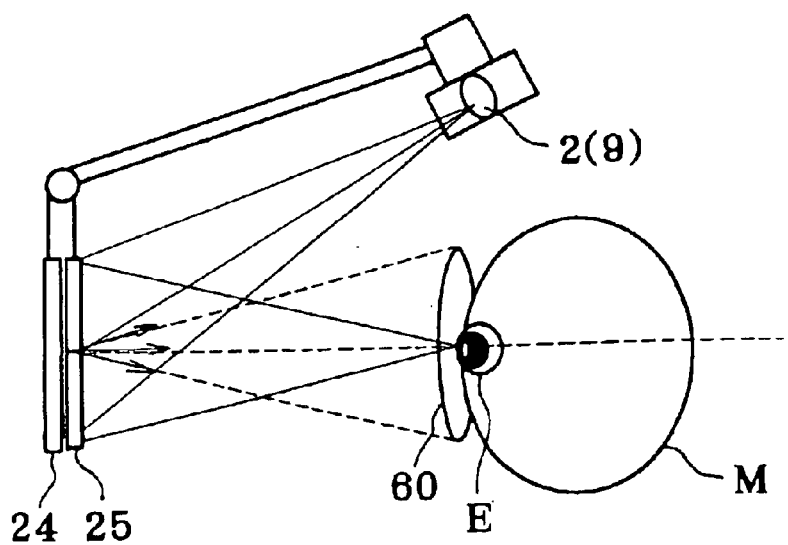
FIG. 12(b) is illustrative of how that projection viewing system is set up.

FIG. 12(a) is illustrative in conception of optical systems in the projection viewing system constructed according to the present invention, and FIG. 12(b) is illustrative of how that projection viewing system is set up. In FIG. 12(b), a concave mirror 24 is constructed of a Fresnel concave reflecting mirror. As already described, the display device, light sources and scanning mans are not shown. In FIG. 12(b), light beams from an image appearing on the display device or from the light sources for the same are deflected by the scanning means. The formed image is magnified and projected through the projection optical system 2(9). A diffusing plate 25 and an eyepiece optical system are located in the vicinity of the projected image.

Comprising the concave mirror 24, the eyepiece optical system forms the exit pupil of the projection optical system 2(9) at a given position that is substantially in line with the eyeball of a viewer M. In this projection viewing system, too, the exit pupil image 6 of the projection type optical system 2(9) is formed through the eyepiece optical system 24. The exit pupil image 6 is then magnified to an exit pupil image 60 of easy-to-view size by the diffusing plate 25. It is thus possible for the viewer M to view the projected image as an image under observation even when the eye E of the viewer M is more or less displaced from the exit pupil image 6. As a result, it is possible to achieve an easy-to-observe projection viewing system, as in FIG. 1 or the like.

In the present invention, the diffusing plate 25 is located on the entrance side of the concave mirror 24 forming the eyepiece optical system, as shown in FIG. 12(a). Accordingly, light rays from the projection viewing system 2(9) to the position of the exit pupil 60 make a total of two roundtrip transmissions through the transmission hologram 25. This is a feature of the present invention. In other words, the light is diffracted twice through the transmission hologram 25. On the basis of this, the angle of the first transmission (before incident on the concave mirror 24) of light through the transmission hologram 25 is intentionally allowed to differ from the angle of the second transmission (after incident on the concave mirror 24) of light through the transmission hologram 25, thereby preventing light from being diffracted only once depending on the wavelength selectivity of that hologram. The arrangement for this will be described later.

As is the case with the diffusing plate 5 and for the same reason as mentioned above, the diffusing plate 25 should preferably have an angle of diffusion of up to 20° at full width half maximum. More preferably, the angle of diffusion should be at least 10° at full width half maximum.

Moreover, the diffusibility of the diffusing plate 25 should be such that the angle of diffusion is preferably up to 40° and more preferably up to 30° at a 1/10 full width.

When a stereoscopic image is observed as in FIGS. 1 and 2, the diffusibility of the diffusing plate 25 should be such that the angle of diffusion is up to 8° at full width half maximum or up to 12° at a 1/10 full width.

Figure 13A:
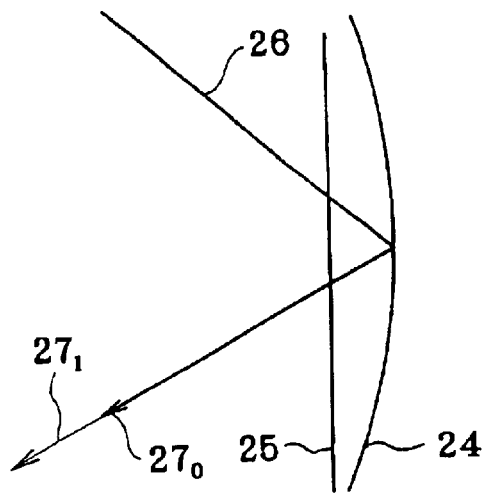
FIGS. 13(a), 13(b) and 13(c) are optical path diagrams for a combination of a diffusing plate comprising a transmission hologram through which light is flexed upon the first transmission with a concave mirror forming the eyepiece optical system.

Next, the relation between the flexion and the chromatic dispersion of the diffusing plate 25, and the position relation between the concave mirror 24 forming the eyepiece optical system and the diffusing plate 25 is explained. The diffusing plate 25 is fabricated by recording of interference between reference light and object light from a diffusing light source (secondary light source). Suppose here that reference light and object light are coaxially (in-line) positioned. Then, as shown in FIG. 13(a), an axial chief ray 26 from the projection optical system 2(9) is first incident on the diffusing plate 25, passing straightforward or without being flexed through the diffusing plate 25. The chief ray passing straightforward through the diffusing plate 25 is reflected at the concave mirror 24, turning direction. The reflected chief ray enters the diffusing plate 25 from its back surface, passing straightforward through the diffusing plate 25. If, in this case, the angle of incidence of the incident light upon the first incidence satisfies the angle of incidence of reconstruction light of the transmission hologram (diffusing plate 25) (the angle at which diffraction efficiency reaches substantially a peak), then diffused light by diffraction is distributed around the chief ray passing straightforward at the first transmission. Upon the second transmission, the diffused light passes substantially straightforward through the diffusing plate 25. On the other hand, if, upon the second incidence, the angle of incidence of the incident light satisfies the angle of incidence of the reconstruction light, then the axial chief ray 26 passes substantially straightforward or without being diffracted through the diffusing plate 25 upon the first transmission. Upon the second transmission, diffused light by diffraction is distributed around the chief ray passing straightforward through the diffusing plate 25. In any case, zero-order light $27_0$ and chief ray $27_1$ propagate in the same direction, as shown in FIG. 13(a), in which no diffused light is shown. In FIG. 13(a), only zero-order light $27_0$ not diffracted through the diffusing plate 25 and only chief ray (center ray) $27_1$ in the diffused light by diffraction are shown. In FIG. 13(a), the zero-order light $27_0$ and chief ray $27_1$ propagate in the same direction, arriving at the center of the exit pupil 60 of the viewing system. Therefore, when the diffusing plate 25 has only a diffusing action and has not any optical-path flexing action as shown in FIG. 13(a), not only the diffused light but also the zero-order light $27_0$ not diffused by diffraction arrives at the exit pupil 60. This is not preferable because the spot of zero-order light $27_0$ appears at the center of an image under observation.

Figure 13B:
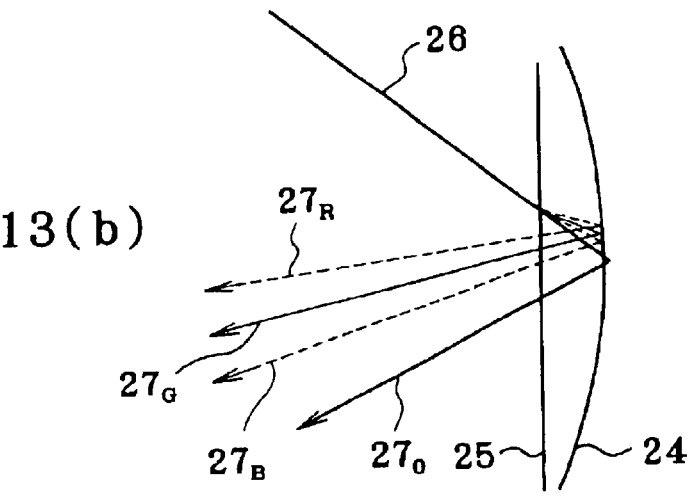
Figure 13C:
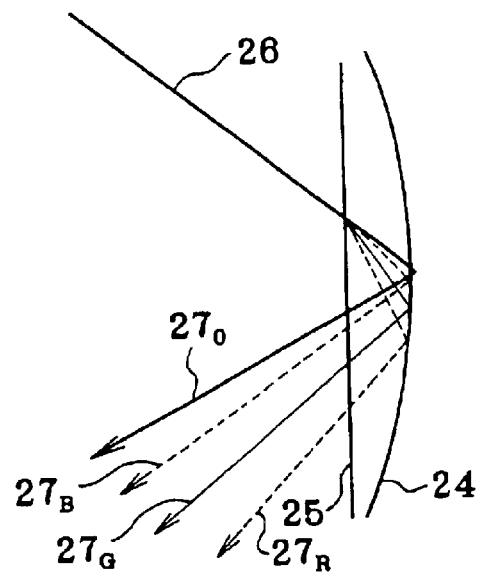
Figure 14A:
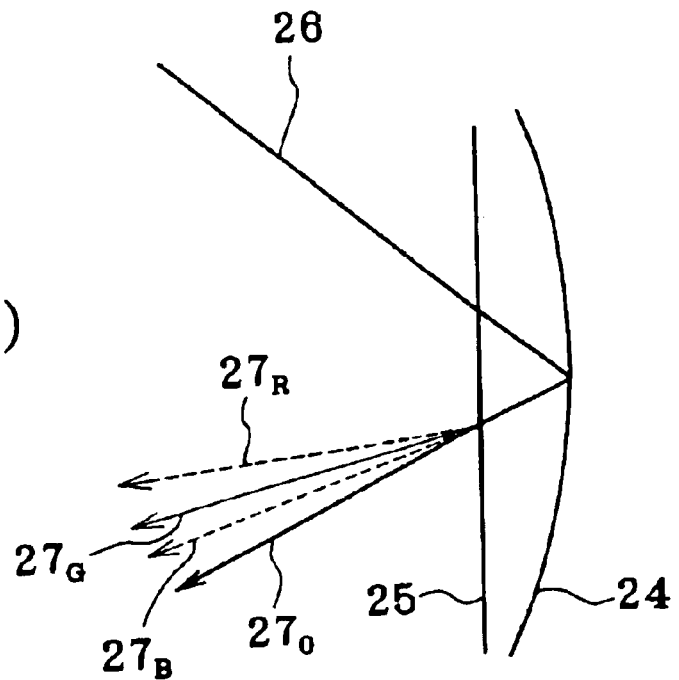
FIGS. 14(a) and 14(b) are optical path diagrams for a combination of a diffusing plate comprising a transmission hologram through which light is flexed upon the second transmission with a concave mirror forming the eyepiece optical system.
Figure 14B:
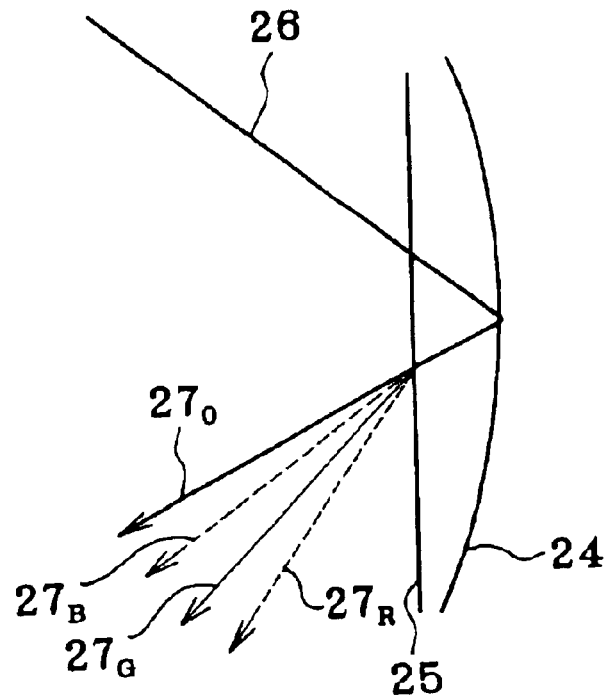

Therefore, a diffusing plate obtained by recording of interferences between reference light and object light in an off-line relation, viz., in a mutually uncoaxial relation is used as the diffusing plate 25. When light that satisfies the angle of incidence of reconstruction light is diffracted through the diffusing plate 25 obtained in such an off-line relation, the flexion of light rays occurs with chromatic dispersion. Such optical paths as shown in FIGS. 13(b) and 13(c) and such optical paths as shown in FIGS. 14(a) and 14(b) are taken depending on the direction of that flexion. However, it is noted that in FIGS. 13(b) and 13(c), the condition regarding the angle of incidence of reconstruction light for the diffusing plate 25 is satisfied upon the first incidence, and in FIGS. 14(a) and 14(b), that condition is satisfied upon the second incidence. In FIG. 13(b) and FIG. 14(a), the direction of flexion of light through the diffusing plate 25 is such that the angle of diffraction becomes small with respect to the angle of incidence to normal, and in FIG. 13(c) and FIG. 14(b), that direction is such that the angle of diffraction becomes large with respect to the angle of incidence. In these figures, no diffused light is shown. Chief rays (center rays) of R, G and B wavelengths diffracted and flexed through the diffusing plate 25 are indicated by $27_R$, $27_G$ and $27_B$. Suppose now that a transmission hologram having an action on the flexion of light rays is used. As can be seen from FIGS. 13 and 14, zero-order light $27_0$ can then be separated from diffracted light $27_R$, $27_G$ and $27_B$, thereby ensuring that the zero-order light be not incident on the exit pupil 60 of the viewing system. Specifically, it is desired that the zero-order light $27_0$ be incident on a position away from the center of the exit pupil 60 by at least ½ of the pupil diameter.

Here, the angle of flexion (deflection) of light through the transmission hologram is defined by the absolute value γ of a difference between the angle of incidence and the angle of diffraction, as measured at a d-line (of 587.6 nm wavelength). As the angle of flexion γ is too small, the zero-order light is entered in the image under observation, as described above. Conversely, as the angle of flexion is too large, chromatic dispersion becomes too large. As a result, the range where three R, G and B wavelengths are put one upon another at the exit pupil 60, i.e., the exit pupil range where images can be viewed with good chromatic reproducibility becomes too narrow.

Accordingly, the angle of flexion (deflection) γ at d-line through the diffusing plate 25 should preferably satisfy the following condition.

$$\gamma > 1° \qquad (7)$$

More preferably, $$\gamma > 2° \qquad (7\text{-}1)$$

Even more preferably, $$\gamma > 10° \qquad (7\text{-}2)$$

On the other hand, it is also preferable to satisfy the following condition:

$$\gamma < 45° \tag{8}$$

More preferably, $$\gamma < 20° \tag{8-1}$$

Combining condition (7-2) with condition (8-1) results in the following condition (9), which should preferably be satisfied.

$$10° < \gamma < 20° \tag{9}$$

Condition (9) is further explained. As the lower limit of 10° to this condition (9) is not reached, the zero-order light is less separable from normal viewing light enabling images under observation to be viewed. For this reason, as the viewer moves its head slightly, the glare of the zero-order light often enters his eye. As the upper limit of 20° is exceeded, chromatic dispersion due to the transmission hologram 25 becomes large. As a result, the viewing range becomes narrow.

Here let R be light of 700 nm wavelength and B be light of 400 nm wavelength. Then, the difference in the angle of diffraction between diffracted light $27_R$ and $27_B$ should preferably be reduced as much as possible. Specifically, that difference should preferably be up to 18°. This is necessary to prevent the exit pupil range where images can be viewed with good reproducibility from becoming too narrow, as described above. Again let R be light of 700 nm wavelength and B be light of 400 nm wavelength. At the position of the exit pupil 60 of the viewing system, the difference in the entrance position between diffracted light $27_R$ and $27_B$ should preferably be reduced as much as possible. Specifically, that difference should preferably be up to ½ of the diameter of the exit pupil 60.

In FIGS. 13 and 14, the axial chief ray 26 from the projection optical system 2(9) or the zero-order light $27_0$ is assumed to be obliquely incident on the concave mirror 24 (at an angle β with respect to normal at the entrance position of the concave mirror 24). Suppose here that the axial chief rays 26 or the zero-order light $27_0$ is incident at substantial right angles (β≈0°) on the concave mirror 24. Then, the chief rays 27R, 27G and 27B leaving the hologram after passed twice through the diffusing plate 25 travel in a substantially opposite direction to the axial chief ray 26. This results in interference of the position of the exit pupil 60 of the viewing system with the projection optical system 2(9). Accordingly, the angle of incidence β of the axial chief ray 27 from the projection optical system 2(9) or the zero-order light $27_0$ on the concave mirror 24 should preferably satisfy the following condition.

$$0° < \beta < 45° \tag{10}$$

More preferably, $$5° < \beta < 20° \tag{10-1}$$

This condition (10-1) is further explained. As the lower limit of 5° to this condition is not reached, the amount of decentration of the concave mirror 24 becomes small, resulting in conjugate reconstruction at the diffusing plate 25 and, hence, a decrease in the quantity of light that can be utilized for observation of displayed images. As the upper limit of 20° to this condition is exceeded, the amount of decentration of the concave mirror 24 becomes too large, resulting in an increase in projected pupil aberration and rendering it difficult to view images of uniform brightness.

In FIGS. 13 and 14, the axial chief ray 26 is assumed to be incident on substantial centers of the diffusing plate 25 and the concave mirror 24 on the back surface side, and there is assumed to be no decentration between the diffusing plate 25 and the concave mirror 24. As can be seen from FIGS. 13 and 14, the projected (diffracted) light $27_R$, $27_G$ and $27_B$ are at angles with respect to the diffusing plate 25, and the exit pupil 60 of the viewing system is not positioned on the front of the diffusing plate 25. Accordingly, the viewer would view images projected from an oblique direction; the image under observation would become a tilted image leading to an image distortion.

Figure 15A:
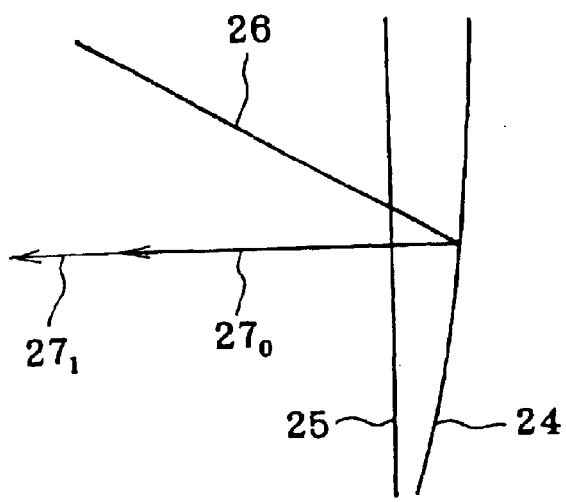
FIGS. 15(a), 15(b) and 15(c) are optical path diagrams for a combination of a diffusing plate comprising a transmission hologram through which light is flexed upon the first transmission with a decentered concave mirror forming the eyepiece optical system.
Figure 15B:
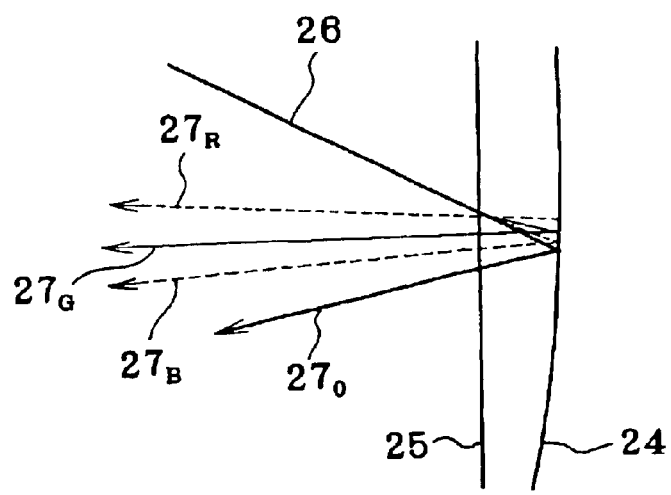
Figure 15C:
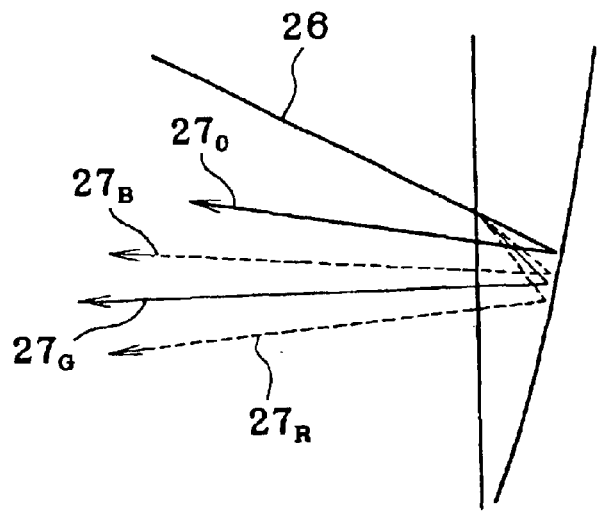

To avoid this, the concave mirror 24 is decentered (e.g., upward) with respect to the diffusing plate 25, as shown in FIGS. 15(a), 15(b) and 15(c), so that the chief rays $27_R$, $27_G$ and $27_B$ reflected at the concave mirror 24 are at substantially right angles with the diffusing plate 25 after the second transmission through the diffusing plate 25. It is noted that FIGS. 15(a), 15(b) and 15(c) correspond to FIGS. 13(a), 13(b) and 13(c), respectively.

It should be understood that since the projected image is projected from the projection optical system 2(9) obliquely onto the diffusing plate 25, the projected image on the diffusing plate 25, too, becomes a tilted image leading to an image distortion. It is thus preferable to use an optical system having a function to correct such a tilted image leading to an image distortion as the projection optical system 2(9).

The exit pupil 60 of the viewing system is positioned on the front of the diffusing plate 25, and the axial chief ray 26 from the projection optical system 2(9) or the zero-order light $27_0$ is allowed to be obliquely incident on the concave mirror 24, so that surface specular light providing noise light can be prevented from entering the exit pupil 60 of the viewing system. This noise light stems from the reflection at the surface of the diffusing plate 25 of the projected light from the projection optical system 2(9).

The ratio γ/β between the above angle of flexion (deflection) and the angle of incidence of light on the concave surface 24 should preferably satisfy the following condition.

$$0.01 < \gamma/\beta < 1{,}000 \tag{11}$$

More preferably, $$0.5 < \gamma/\beta < 2 \tag{11-1}$$

This condition (11-1) is further explained. As the lower limit of 0.5 to this condition is not reached, the angle of flexion of light through the transmission hologram 25 becomes small. This would cause the zero-order light not diffracted through the transmission hologram 25 to enter the exit pupil 60 of the viewing system, resulting in spot flares appearing on an image under observation. As the upper limit of 2 is exceeded, the amount of decentration of the concave mirror 24 becomes relatively small. In addition, there is an undesired light ray that, upon incidence on the transmission hologram 25, is reflected at the concave mirror 24, then Fresnel reflected, if slight, at the back surface of the transmission hologram 25, and again reflected at the concave mirror 24. This light ray would enter the exit pupil 60, and then be viewed as a spot flare.

Even more preferably in view of prevention of spot flares, $$1 < \gamma/\beta < 1.5 \tag{11-2}$$

When the diffusing plate 25 is used, it is desired to use LEDs or LDs of high chromaticity for light sources for illuminating the display devices 1, 1L, 1R, preferably in combination with three RGB colors. For the incidence of light on the scanning means 8, 8L, 8R, 8₁, 8₂, too, it is preferable to use such LEDs or LDs as the light sources 7, 7L, 7R, 7₁, 7₂.

Embodiments of the optical systems in the projection viewing system of the invention are now explained.

Figure 16:
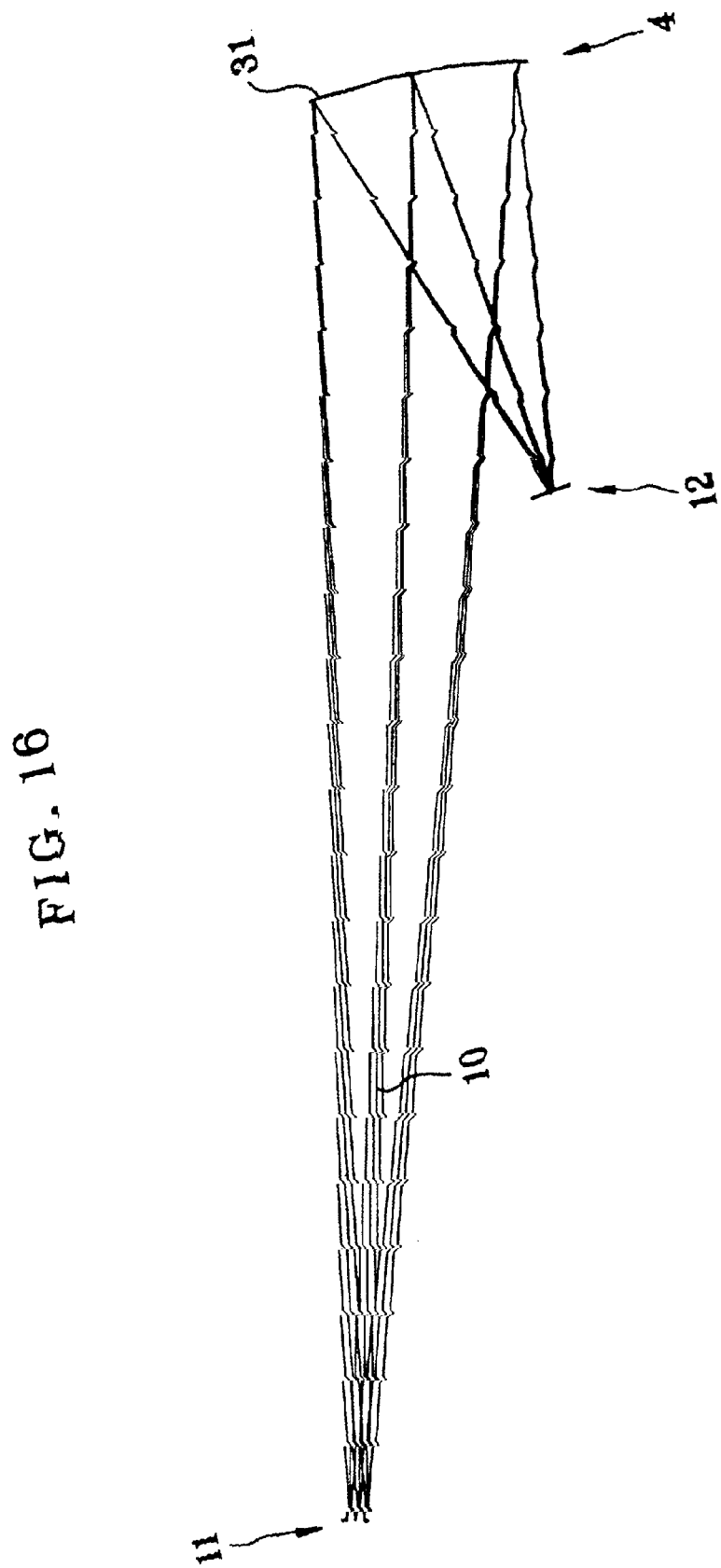
FIG. 16 is an optical path diagram for Example 1 of the eyepiece optical system of the invention, inclusive of its optical axis.
Figure 17:
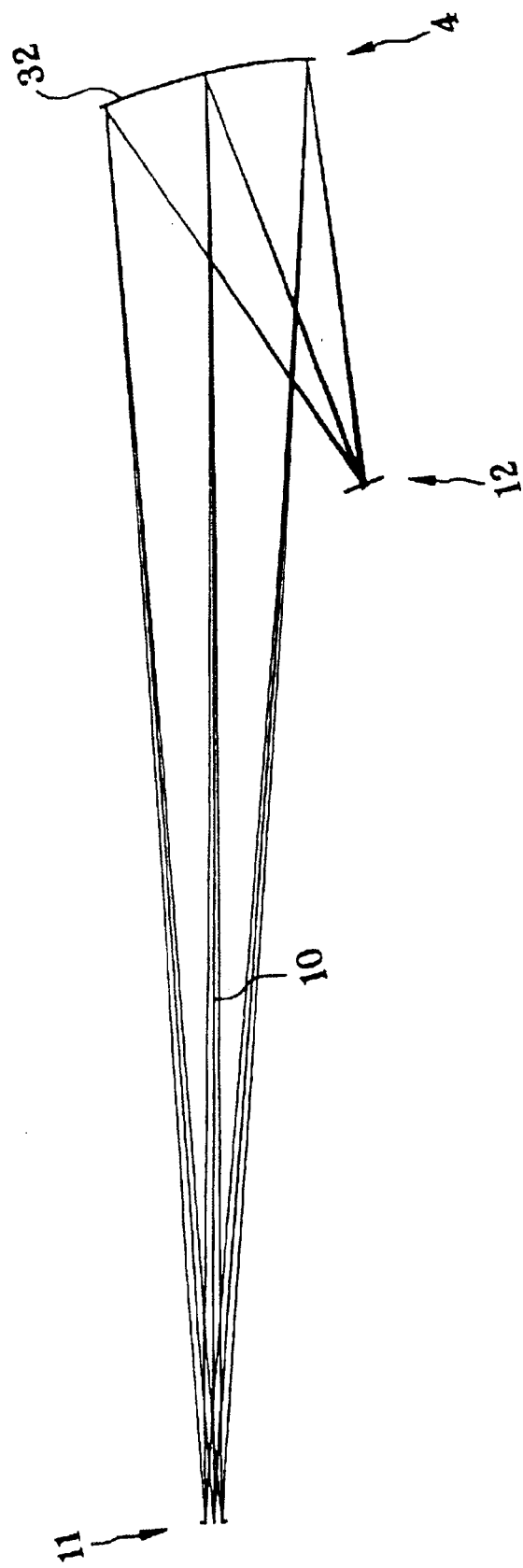
FIG. 17 is an optical path diagram for Example 2 of the eyepiece optical system of the invention, inclusive of its optical axis.
Figure 18:
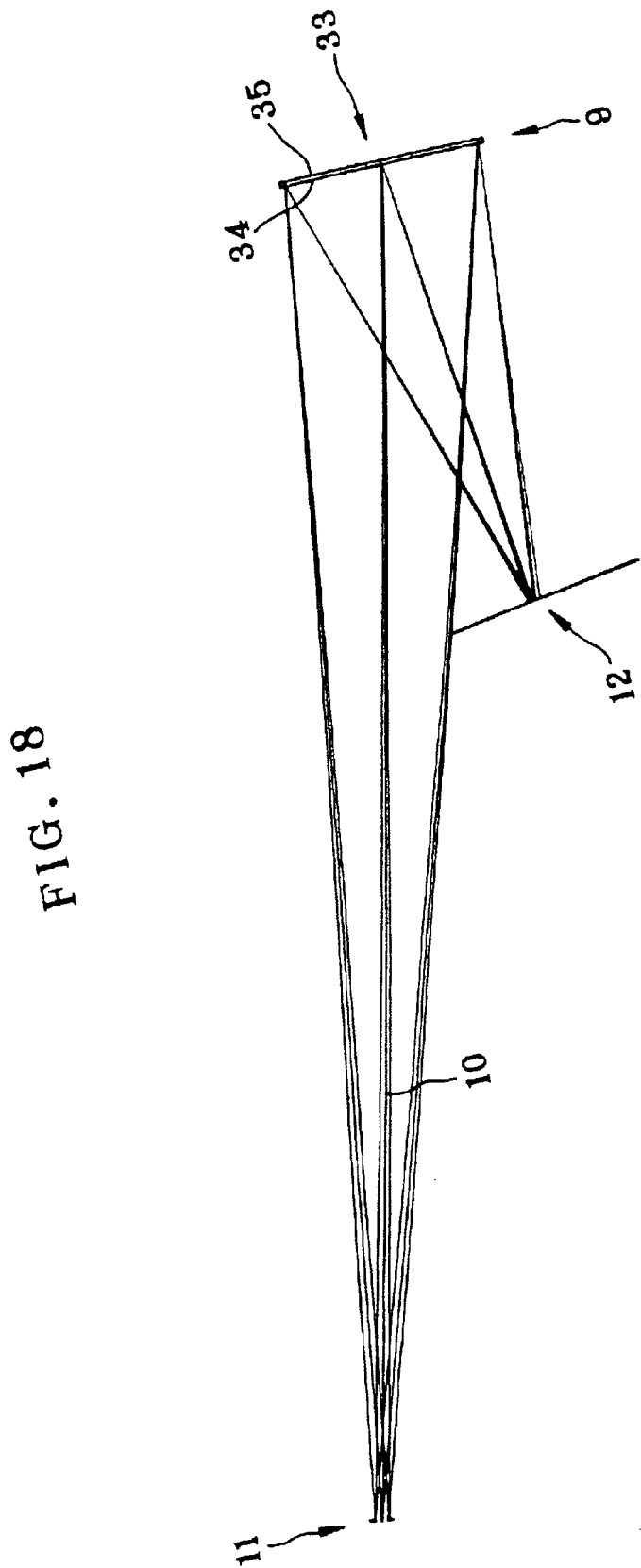
FIG. 18 is an optical path diagram for Example 3 of the eyepiece optical system of the invention, inclusive of its optical axis.

First, examples of the eyepiece optical system 4 are given. The eyepiece optical system 4 used with the projection type optical system of the invention is embodied as Examples 1 to 3. Optical path diagrams for the respective examples are shown in FIGS. 16 to 18. In each example, ray tracing is carried out in the form of back tracing from surface 11 (object plane) to surface 12 (image plane). Here the surface 11 corresponds to the pupil position of the viewer, and the surface 12 corresponds to the positions of the exit pupils $16_1$ and $16_2$ (FIG. 10) of the projection optical system 9L, 9R, $9_1$, $9_2$ (FIGS. 2–3 and FIGS. 9–11). It is noted that in a practical embodiment of the projection viewing system, a diffusing surface having a diffusing action or a diffusing plate having a diffusing action is located in the vicinity of the eyepiece optical system. In Examples 1 to 3 given below, however, it is presumed that there is neither any diffusing plate nor any diffusing surface.

Each surface is expressed in terms of the amount of decentration from the reference eyepiece optical system 4, and the diffusing surface having a diffusing action is to be located in the vicinity of the surface of the eyepiece optical system 4.

In any case, the size of the screen (the eyepiece optical system) is 162.56×121.92 mm.

EXAMPLE 1

As shown in FIG. 16, an anamorphic reflecting mirror 31 is constructed as the eyepiece optical system 4.

EXAMPLE 2

As shown in FIG. 17, a reflecting surface 32 defined by a free-form surface is constructed as the eyepiece optical system 4.

EXAMPLE 3

As shown in FIG. 18, a Fresnel back-surface mirror 33 is constructed as the eyepiece optical system 4. The Fresnel back-surface mirror 33 has an entrance surface 34 defined by a plane and a back surface 35 defined by a Fresnel reflecting surface.

Construction parameters for Examples 1–3 will be given later.

Examples of the projection optical systems 9L, 9R, $9_1$ and $9_2$ are given. The projection optical system used with the projection viewing system of the invention is embodied as Examples 4 and 5. Optical path diagrams for the respective examples are shown in FIGS. 19–22. In Examples 4 and 5, normal ray tracing is carried out; that is, rays are traced from a light source 7 toward a scanning surface 40. Referring to the reference coordinates for decentration, the amount of decentration is given on the basis of the light source 7. In either case, the size of the scanning surface 40 is 162.56× 121.92 mm.

EXAMPLE 4

Figure 19:
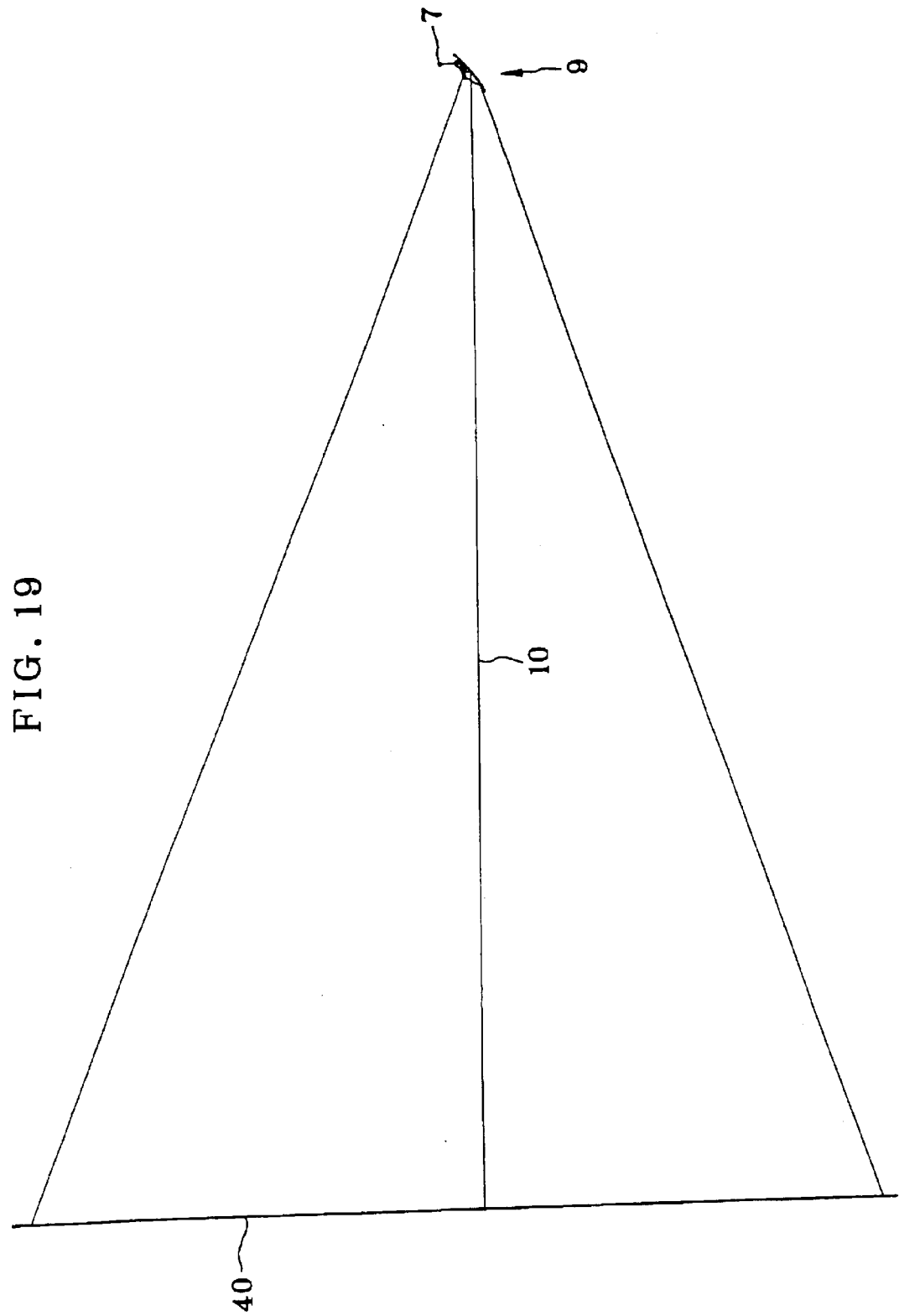
FIG. 19 is an optical path diagram illustrative in Y-Z section of the whole optical system of Example 4 of the invention from the light source to the scanning surface.
Figure 20:
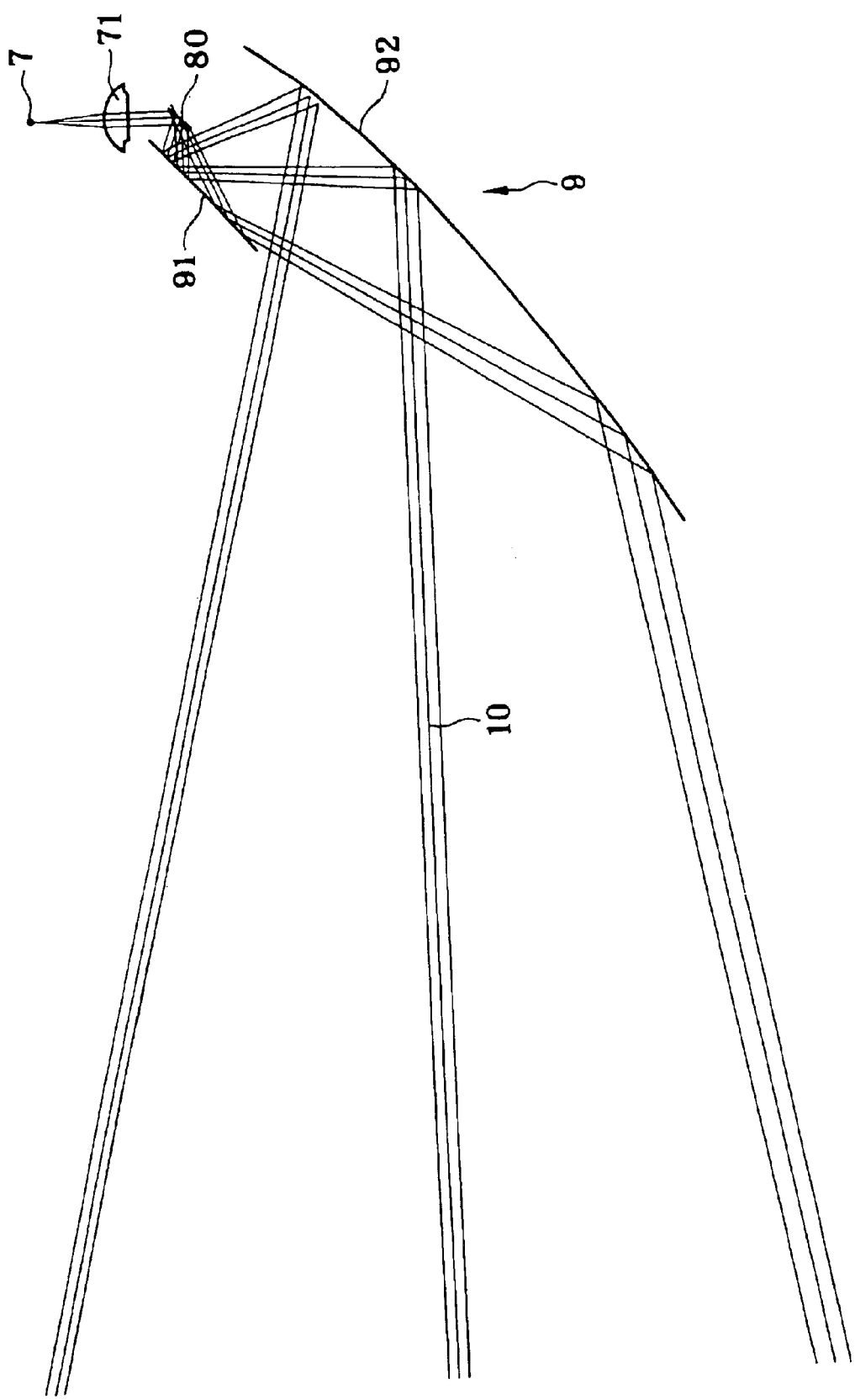
FIG. 20 is an optical path diagram illustrative in Y-Z section of part of FIG. 19.

This example is illustrated in FIGS. 19 and 20. FIG. 19 is an optical path diagram illustrative in Y-Z section of the whole optical system from the light source 7 to the scanning surface 40, and FIG. 20 is an optical path diagram illustrative in Y-Z section of part of the optical system.

Light rays leaving the light source 7 are collimated via a planeconvex positive lens 71 into a substantially parallel light beam. The planoconvex positive lens 71 forms an illumination optical system, and the second surface thereof comprises an aspheric surface. The substantially parallel light beam enters a scanning mirror 80 that rotates around two orthogonal axes.

The light beam reflected and scanned by the scanning mirror 80 is reflected at decentered reflecting mirrors 91 and 92 in this order to form scanning lines on the scanning surface 40 located far away from the light source 7. The decentered reflecting mirrors 91 and 92 form a projection optical system 9, and comprise free-form surfaces.

The scanning mirror 80 in this example has an angle of inclination of ±10.9886° around the X-axis and an angle of inclination of ±13.3719° around the Y-axis.

EXAMPLE 5

Figure 21:
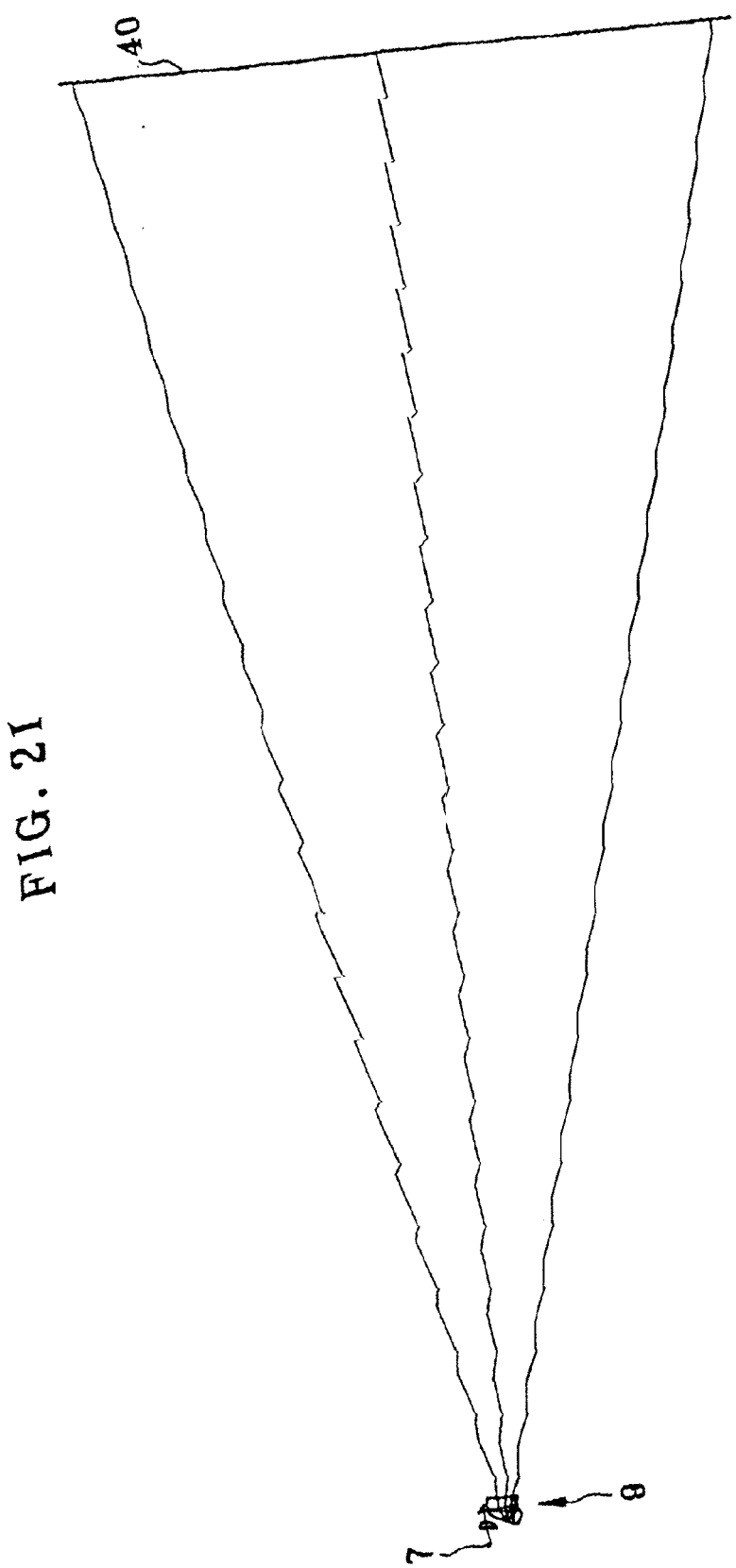
FIG. 21 is an optical path diagram illustrative in Y-Z section of the whole optical system of Example 5 of the invention from the light source to the scanning surface.
Figure 22:
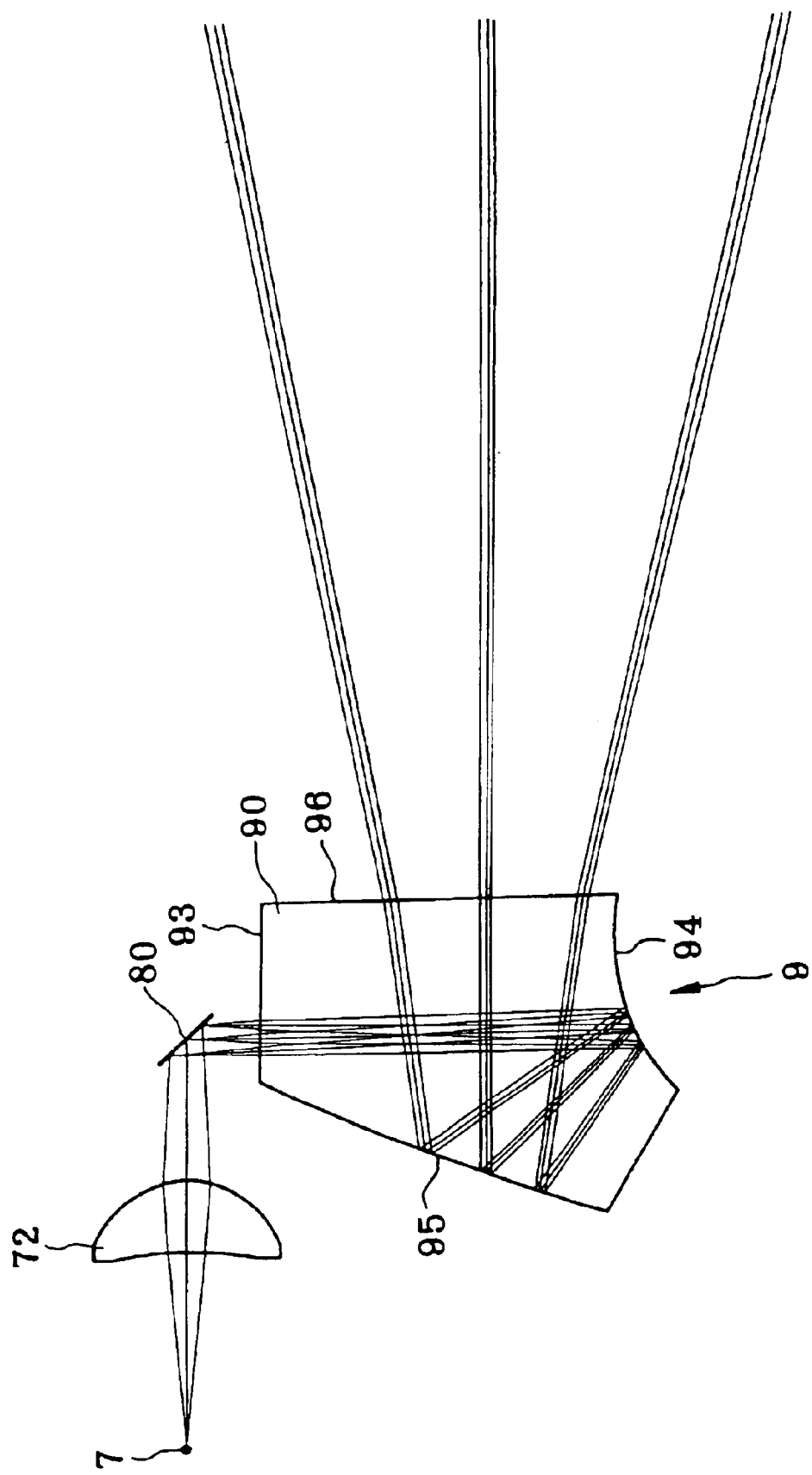
FIG. 22 is an optical path diagram illustrative in Y-Z section of part of FIG. 21.

This example is illustrated in FIGS. 21 and 22. FIG. 21 is an optical path diagram illustrative in Y-Z section of the whole optical system from the light source 7 to the scanning surface 40, and FIG. 22 is an optical path diagram illustrative in Y-Z section of part of the optical system.

Light rays leaving the light source 7 are collimated via a positive meniscus lens 72 into a substantially parallel light beam. The positive meniscus lens 72 forms an illumination optical system, taking on a meniscus shape concave with respect to the light source 7. The substantially parallel light beam enters a scanning mirror 80 that rotates around two orthogonal axes.

The light beam reflected and scanned at the scanning mirror 80 enters a decentered prism 90 from the first surface 93. The decentered prism 90 forms a projection optical system 9. The second surface 94 and the third surface 95 of the decentered prism 90 are each comprised of a free-form surface. The light beam entered in the prism is reflected at the second surface 94 and then at the third surface 95. At this time, the light beam reflected at the third surface 95 crosses an optical path through the prism from the first surface 93 toward the second surface 94. Then, the light beam leaves the prism from the fourth surface 96 to form scanning lines on a scanning surface 40 located far away from the light source 7.

The scanning mirror 80 in this example has an angle of inclination of ±1.5924° around the X-axis and an angle of inclination of ±0.6945° around the Y-axis.

Next, Examples 6 to 13 of the projection optical system 2(9) are given. The projection optical system 2 is provided to magnify and project an exit pupil, and is a combined optical system comprising a concave mirror 24 and a diffusing plate 25 defined by a transmission hologram. In any case, the concave mirror 24 is defined by a Fresnel concave reflecting mirror 24'.

In each example, an object plane is defined by the exit pupil 16 of the projection optical system 2(9), and an image plane is defined by the exit pupil (the magnified exit pupil image of the exit pupil 16) 60 of the viewing system. Ray tracing is carried out in the form of normal ray tracing from the center of the exit pupil 16 of the projection optical system 2(9) to the exit pupil 60 of the viewing system.

EXAMPLE 6

Figure 23:
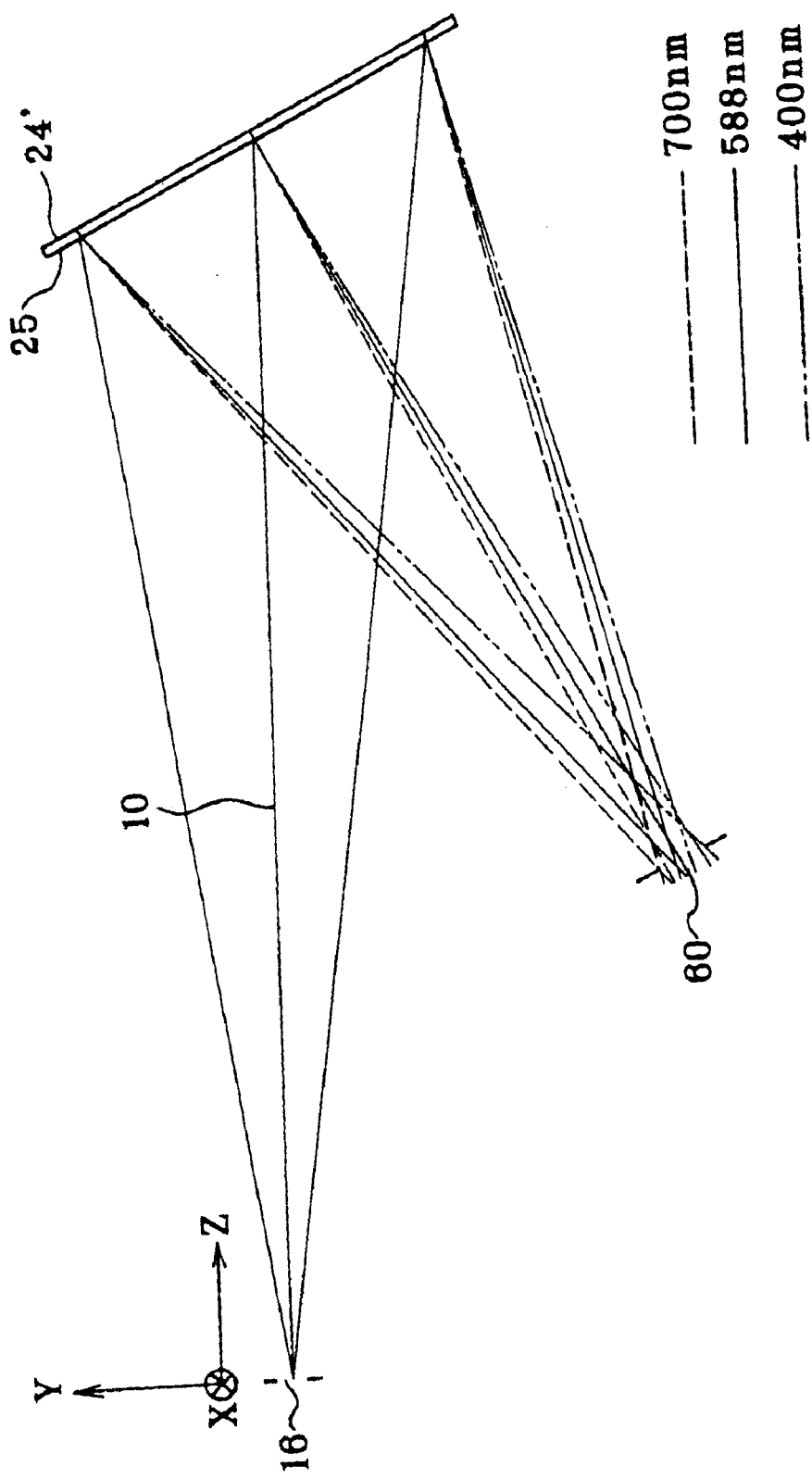
FIG. 23 is an optical path diagram illustrative in Y-Z section of Example 6 of the invention.
Figure 24:
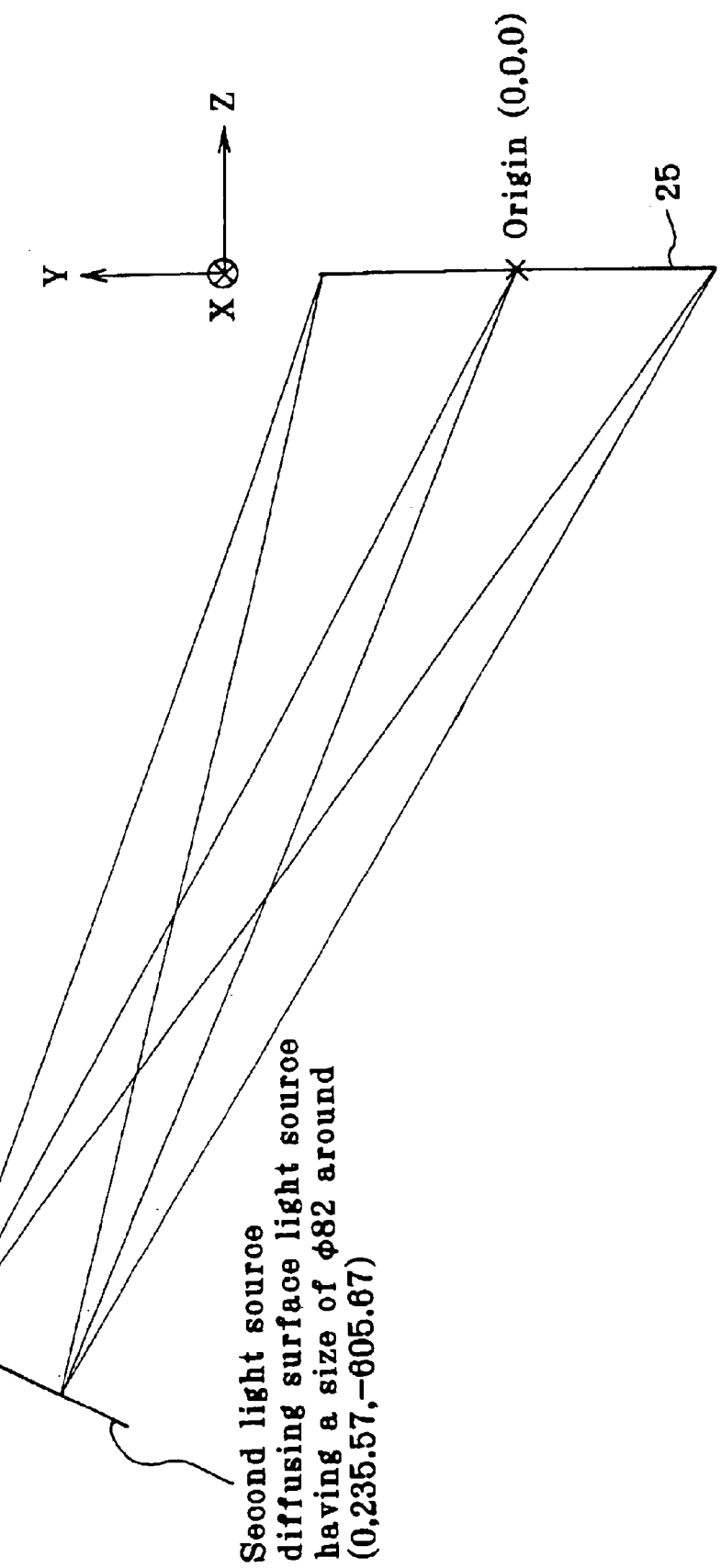
FIG. 24 is illustrative of how to fabricate a transmission hologram used as the diffusing plate in Example 6 of the invention.
Figure 25:
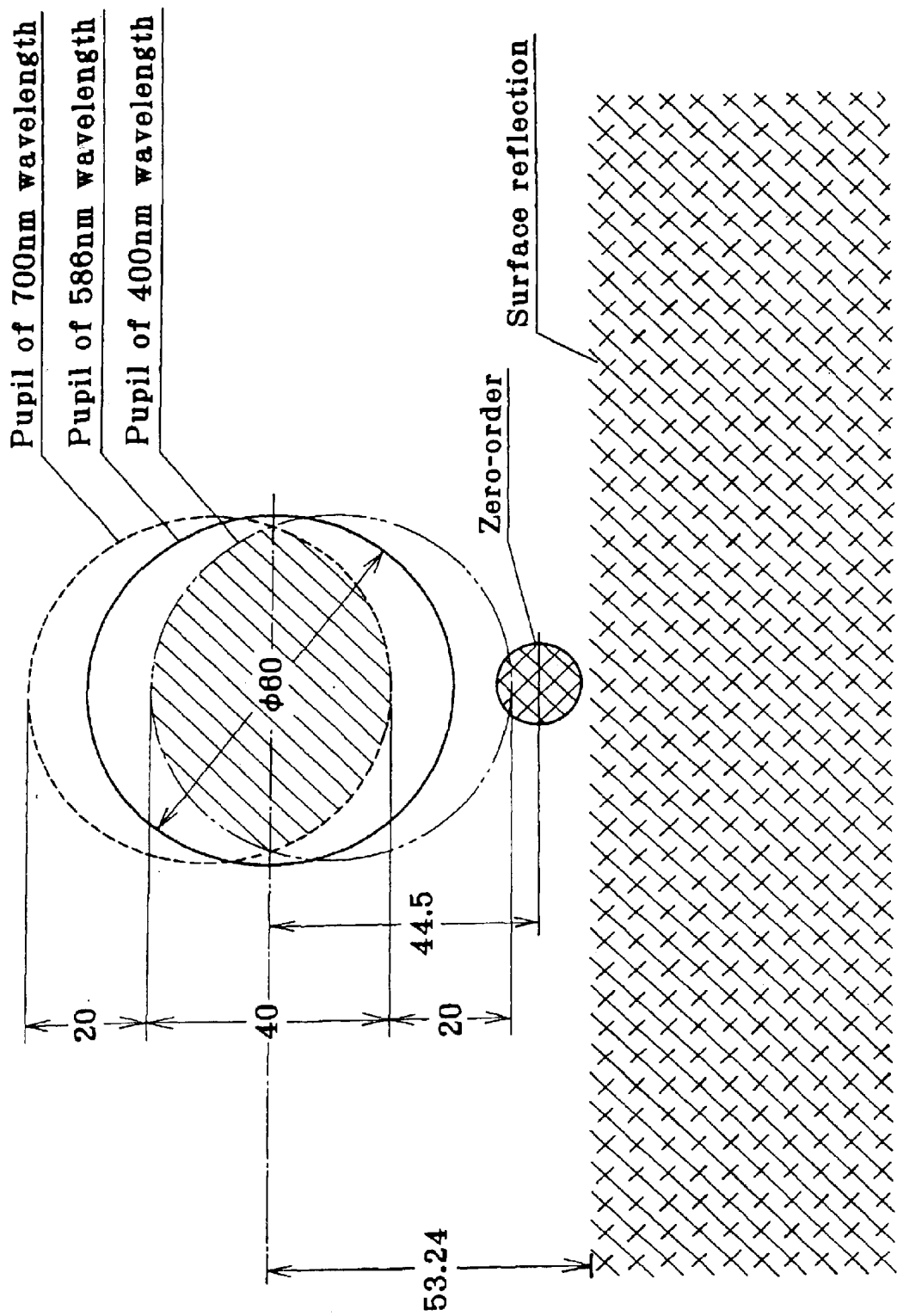
FIG. 25 is illustrative of to what degree RGB exit pupil images overlap at the position of the exit pupil of Example 6 and the positions of incidence of zero-order light and surface reflected light.

An optical path diagram in Y-Z section for this example is illustrated in FIG. 23. FIG. 24 is illustrative of how to fabricate a transmission hologram used as the diffusing plate 25 in this example. FIG. 25 is illustrative of to what degree exit pupil images overlap at the position of the exit pupil 60 in this example, and the positions of incidence of zero-order light and surface reflected light. The exit pupil images are those at 400 nm wavelength, 586 nm wavelength and 700 nm wavelength. In FIGS. 24 and 25, the numeral values are given in mm.

Example 6 corresponds to FIG. 13(b). In Example 6, the condition regarding the angle of incidence of reconstruction light is satisfied upon the first incidence, and no diffraction occurs upon the second incidence. The direction of flexion of light through the diffusing plate 25 is such that the angle of diffraction becomes small with respect to the angle of incidence to normal.

The Fresnel concave reflecting surface 24' is made up of a Fresnel back-surface mirror. Here let MY represent the amount of decentration of the Fresnel back-surface mirror, $\gamma$ represent the angle of deflection of an axial chief ray 10 through the transmission hologram 25, and $\beta$ represent the angle of incidence of light on the Fresnel concave reflecting mirror 24'. Then, MY=89.27 mm $\gamma$=13.15° (in a vitreous material having a refractive index of 1.49)

$\beta$=7.02° (in a vitreous material having a refractive index of 1.49)

Exposure conditions for the transmission hologram 25 in this example are illustrated in FIG. 24, wherein the origin is defined by the point of incidence of an axial chief ray 10 on the surface of the transmission hologram 25. Referring here to a coordinate system for exposure, the hologram surface is defined by an X-Y plane and a Z-axis is defined by a direction going away from the exit pupil 16 of the projection optical system 2(9).

The first light source position (X1, Y1, Z1) for exposure is determined as follows, provided that the light source is given by a point light source.

(X1, Y1, Z1)=(0, 297.11, −578.12)

The second light source position (X2, Y2, Z2) is determined as follows, provided that the second light source is given by a diffusing surface light source having an area of $\phi$82 mm around the light source position.

(X2, Y2, Z2)=(0, 235.57, −605.67)

The transmission hologram fabricated under the above exposure conditions is used as the diffusing plate 25. The light beam diffused through the diffusing plate 25 is reflected at the Fresnel concave back-surface mirror 24' to form a magnified pupil 60 of $\phi$60 at the pupil plane of the viewer.

EXAMPLE 7

Figure 26:
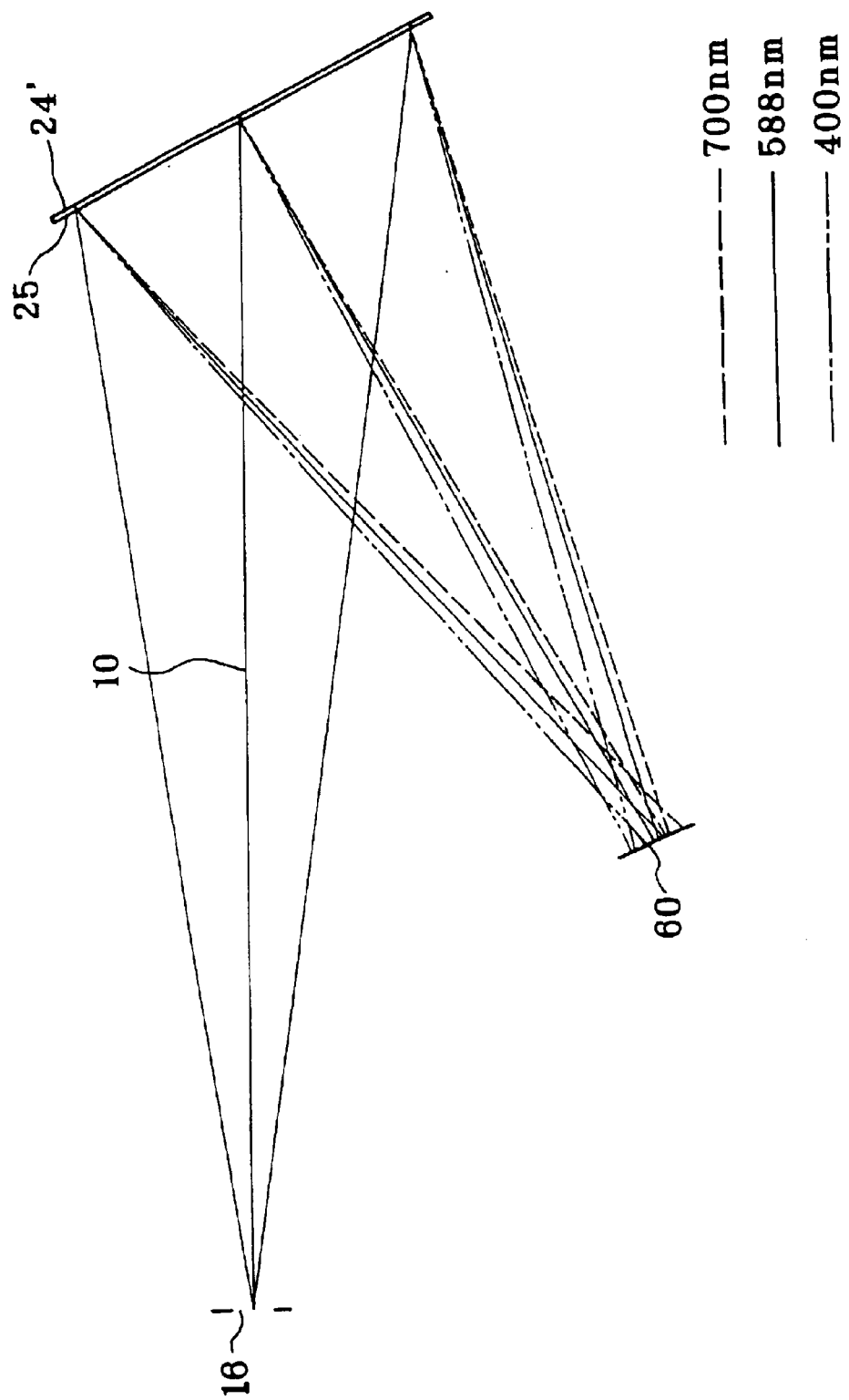
FIG. 26 is an optical path diagram illustrative in Y-Z section of Example 7 of the invention.
Figure 27:
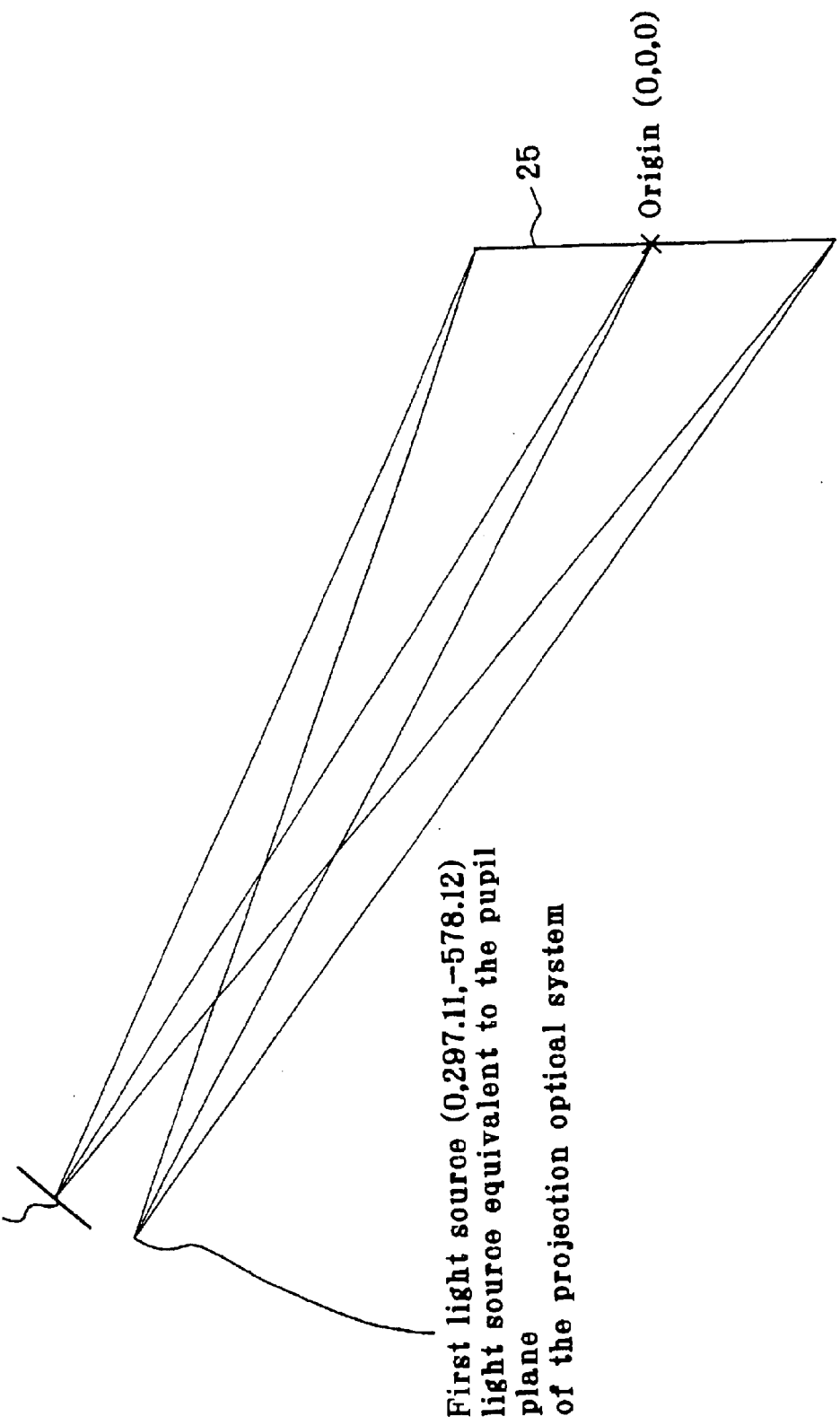
FIG. 27 is illustrative of how to fabricate a transmission hologram used as the diffusing plate in Example 7 of the invention.
Figure 28:
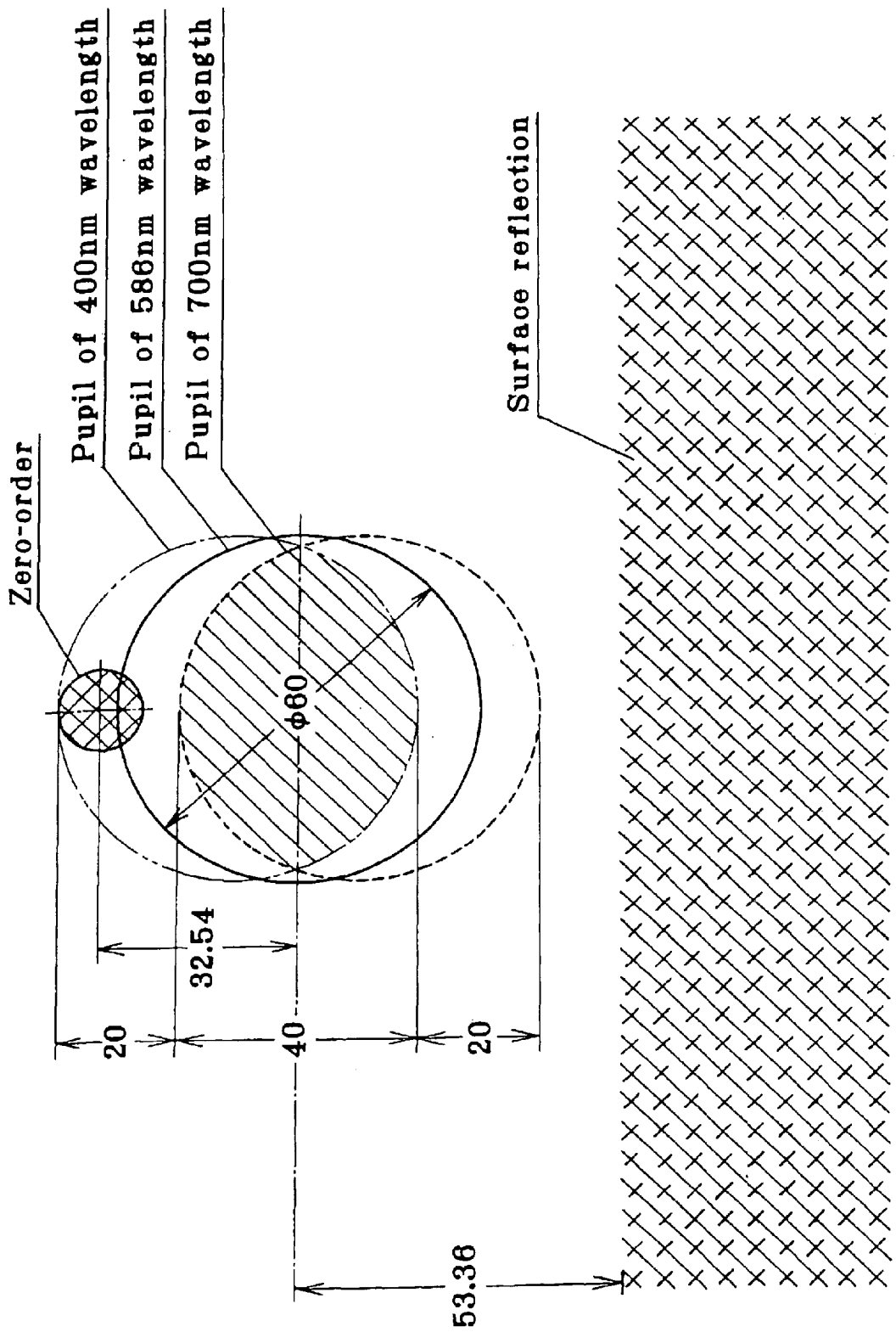
FIG. 28 is illustrative of to what degree RGB exit pupil images overlap at the position of the exit pupil of Example 7 and the positions of incidence of zero-order light and surface reflected light.

An optical path diagram in Y-Z section for this example is illustrated in FIG. 26. FIG. 27 is illustrative of how to fabricate a transmission hologram used as the diffusing plate 25 in this example. FIG. 28 is illustrative of to what degree exit pupil images overlap at the position of the exit pupil 60 in this example, and the positions of incidence of zero-order light and surface reflected light. The exit pupil images are those at 400 nm wavelength, 586 nm wavelength and 700 nm wavelength. In FIGS. 27 and 28, the numeral values are given in mm.

Example 7 corresponds to FIG. 13(c). In Example 7, the condition regarding the angle of incidence of reconstruction light is satisfied upon the first incidence, and no diffraction occurs upon the second incidence. The direction of flexion of light through the diffusing plate 25 is such that the angle of diffraction becomes large with respect to the angle of incidence to normal.

The Fresnel concave reflecting surface 24' is made up of a Fresnel back-surface mirror. Here let MY represent the amount of decentration of the Fresnel back-surface mirror, $\gamma$ represent the angle of deflection of an axial chief ray 10 through the transmission hologram 25, and $\beta$ represent the angle of incidence of light on the Fresnel concave reflecting mirror 24'. Then, MY=130.46 mm $\gamma$=6.61° (in a vitreous material having a refractive index of 1.49)

$\beta$=10.29° (in a vitreous material having a refractive index of 1.49)

Exposure conditions for the transmission hologram 25 in this example are illustrated in FIG. 27, wherein the origin is defined by the point of incidence of an axial chief ray 10 on the surface of the transmission hologram 25. Referring here to a coordinate system for exposure, the hologram surface is defined by an X-Y plane and a Z-axis is defined by a direction going away from the exit pupil 16 of the projection optical system 2(9).

The first light source position (X1, Y1, Z1) for exposure is determined as follows, provided that the light source is given by a point light source.

(X1, Y1, Z1)=(0, 297.11, −578.12)

The second light source position (X2, Y2, Z2) is determined as follows, provided that the second light source is given by a diffusing surface light source having an area of $\phi$82 mm around the light source position.

(X2, Y2, Z2)=(0, 341,33, −553.14)

The transmission hologram fabricated under the above exposure conditions is used as the diffusing plate 25. The light beam diffused through the diffusing plate 25 is reflected at the Fresnel concave back-surface mirror 24' to form a magnified pupil 60 of $\phi$60 at the pupil plane of the viewer.

EXAMPLE 8

Figure 29:
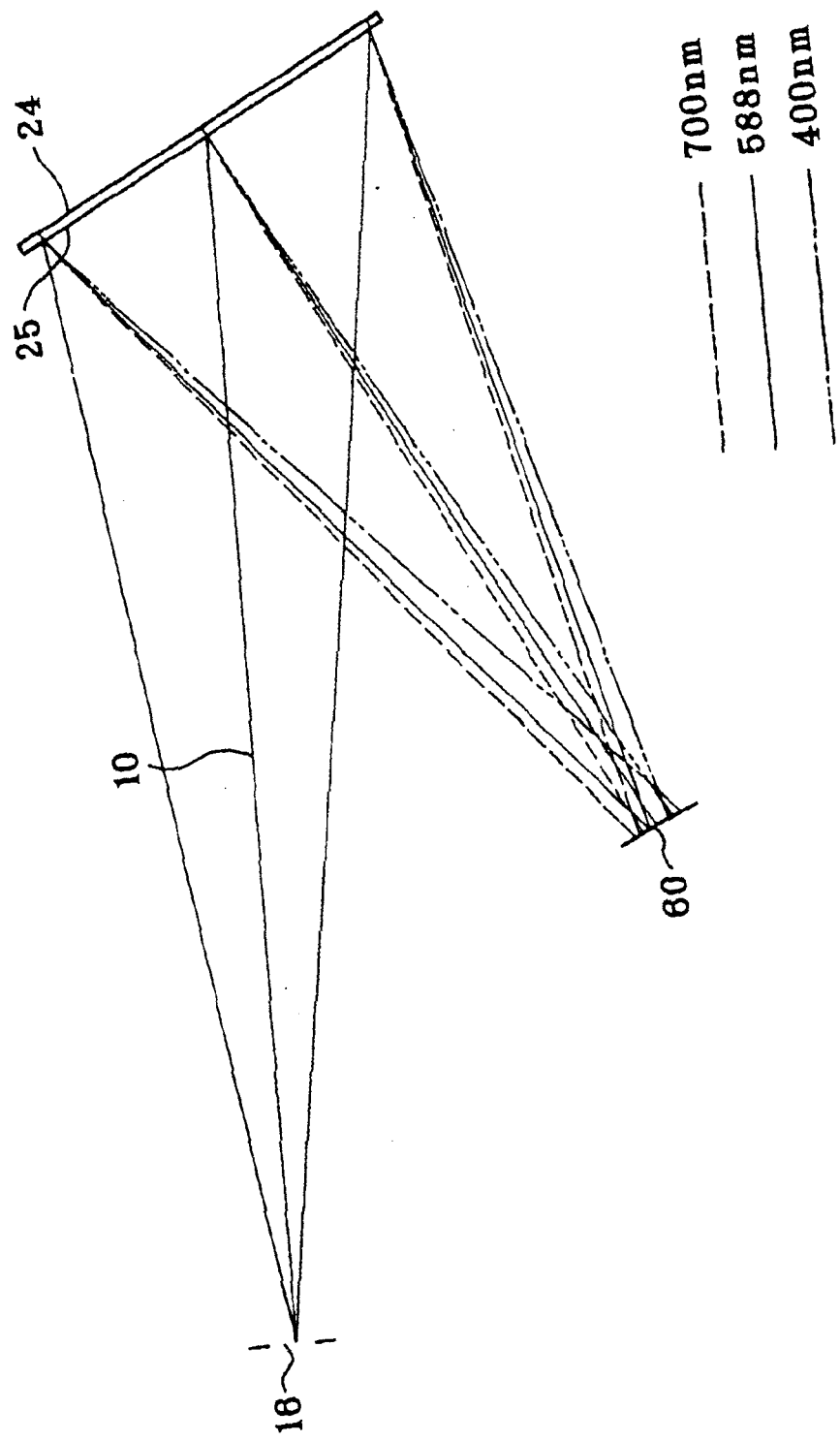
FIG. 29 is an optical path diagram illustrative in Y-Z section of Example 8 of the invention.
Figure 30:
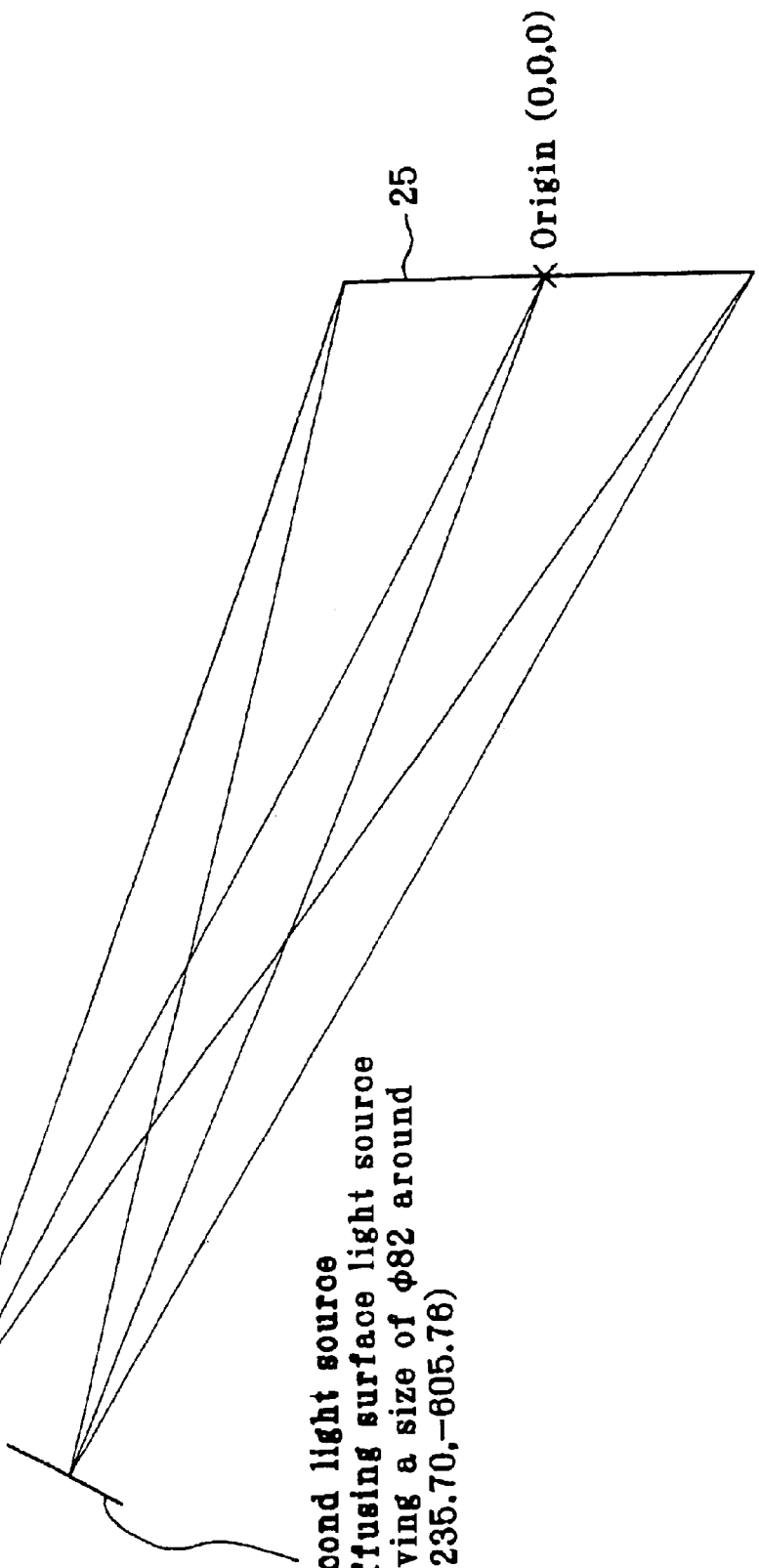
FIG. 30 is illustrative of how to fabricate a transmission hologram used as the diffusing plate in Example 8 of the invention.
Figure 31:
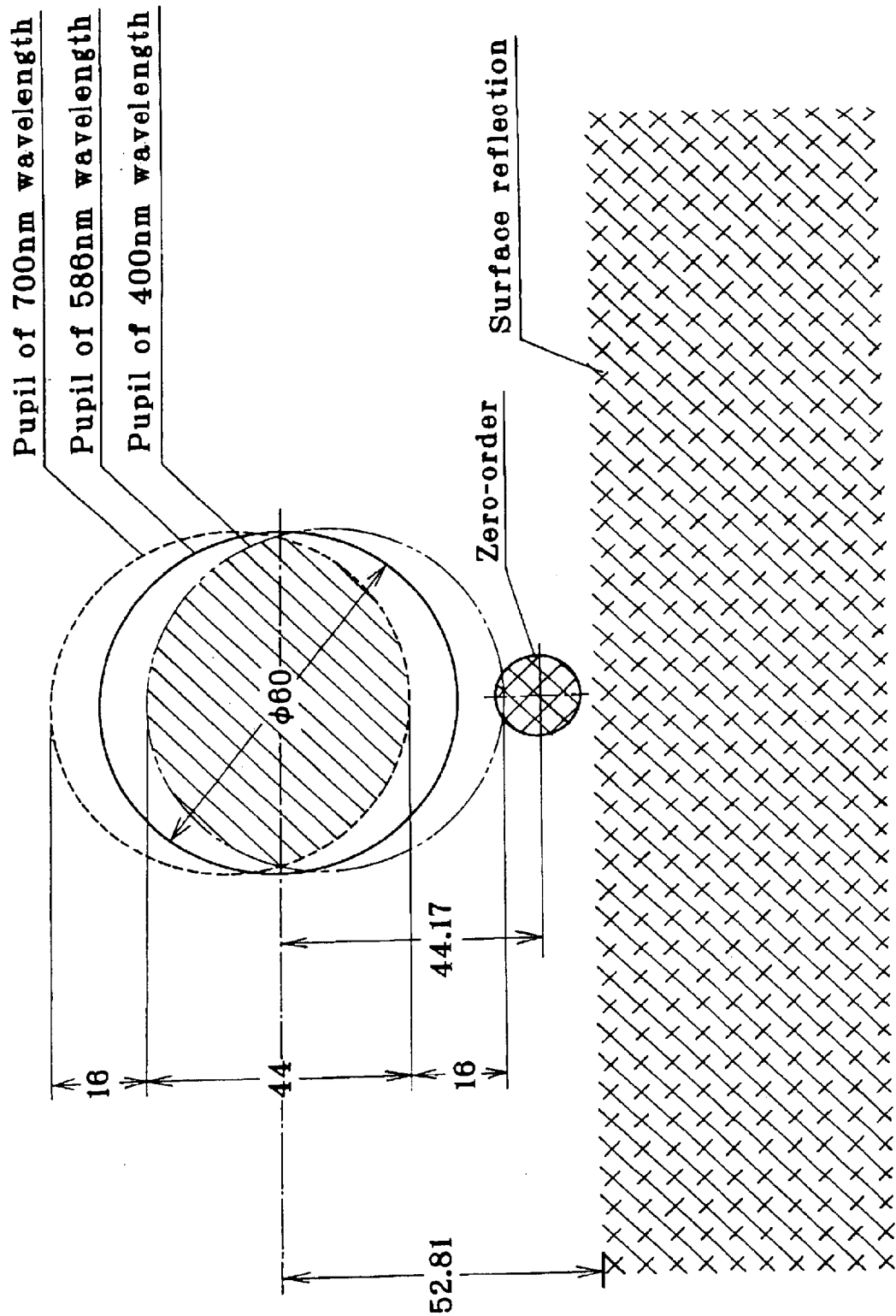
FIG. 31 is illustrative of to what degree RGB exit pupil images overlap at the position of the exit pupil of Example 8 and the positions of incidence of zero-order light and surface reflected light.

An optical path diagram in Y-Z section for this example is illustrated in FIG. 29. FIG. 30 is illustrative of how to fabricate a transmission hologram used as the diffusing plate 25 in this example. FIG. 31 is illustrative of to what degree exit pupil images overlap at the position of the exit pupil 60 in this example, and the positions of incidence of zero-order light and surface reflected light. The exit pupil images are those at 400 nm wavelength, 586 nm wavelength and 700 nm wavelength. In FIGS. 30 and 31, the numeral values are given in mm.

Example 8 corresponds to FIG. 13(b). In Example 8, the condition regarding the angle of incidence of reconstruction light is satisfied upon the first incidence, and no diffraction occurs upon the second incidence. The direction of flexion of light through the diffusing plate 25 is such that the angle of diffraction becomes small with respect to the angle of incidence to normal.

The Fresnel concave reflecting surface 24' is made up of a Fresnel back-surface mirror. Here let MY represent the amount of decentration of the Fresnel back-surface mirror, $\gamma$ represent the angle of deflection of an axial chief ray 10 through the transmission hologram 25, and $\beta$ represent the angle of incidence of light on the Fresnel concave reflecting mirror 24'. Then, MY=90.64 mm γ=14.28° (in a vitreous material having a refractive index of 1.62)

β=6.46° (in a vitreous material having a refractive index of 1.62)

Exposure conditions for the transmission hologram 25 in this example are illustrated in FIG. 30, wherein the origin is defined by the point of incidence of an axial chief ray 10 on the surface of the transmission hologram 25. Referring here to a coordinate system for exposure, the hologram surface is defined by an X-Y plane and a Z-axis is defined by a direction going away from the exit pupil 16 of the projection optical system 2(9).

The first light source position (X1, Y1, Z1) for exposure is determined as follows, provided that the light source is given by a point light source.

(X1, Y1, Z1)=(0, 297.11, −578.12)

The second light source position (X2, Y2, Z2) is determined as follows, provided that the second light source is given by a diffusing surface light source having an area of φ82 mm around the light source position.

(X2, Y2, Z2)=(0, 235.70, −605.76)

The transmission hologram fabricated under the above exposure conditions is used as the diffusing plate 25. The light beam diffused through the diffusing plate 25 is reflected at the Fresnel concave back-surface mirror 24' to form a magnified pupil 60 of φ60 at the pupil plane of the viewer.

EXAMPLE 9

Figure 32:
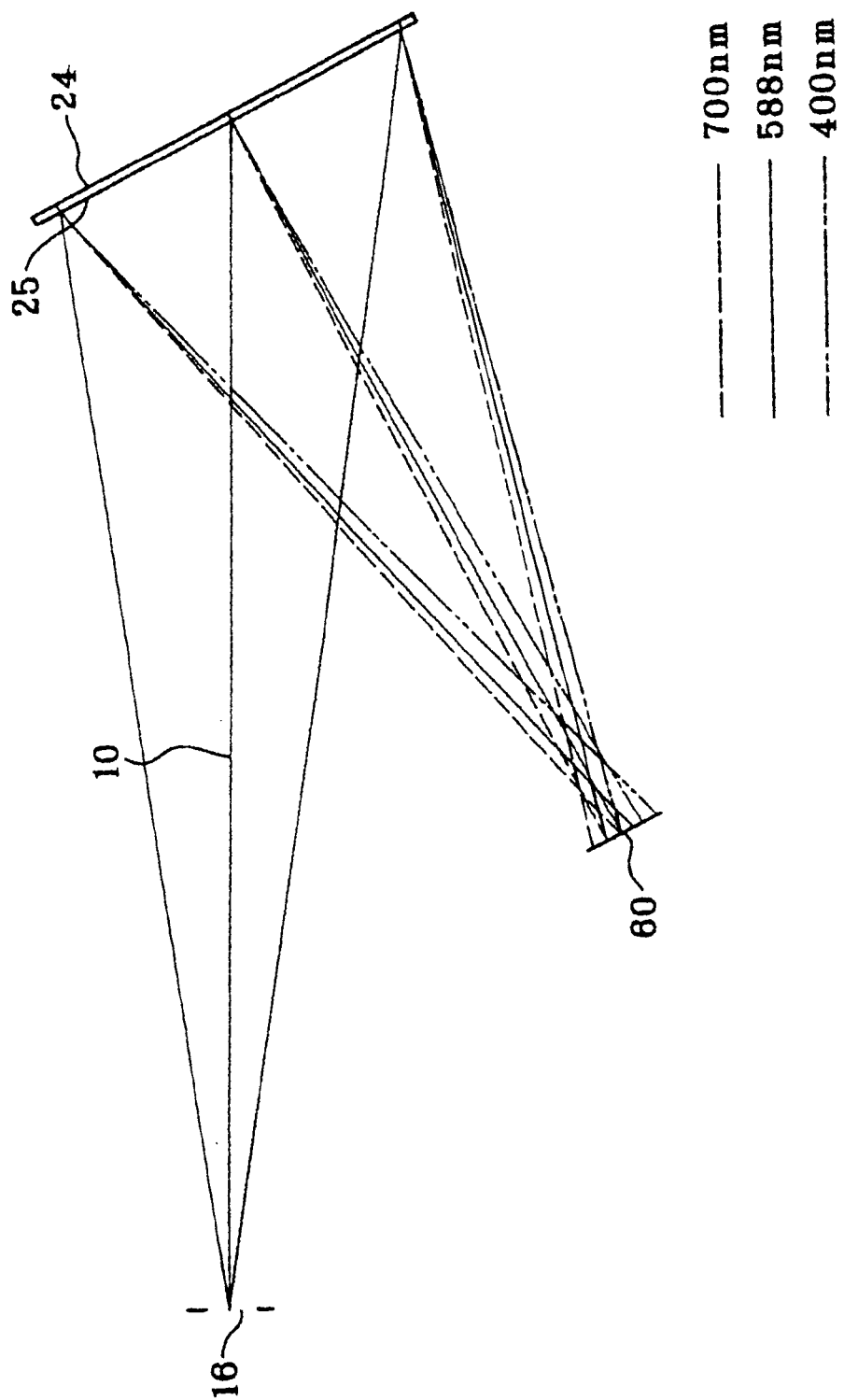
FIG. 32 is an optical path diagram illustrative in Y-Z section of Example 9 of the invention.
Figure 33:
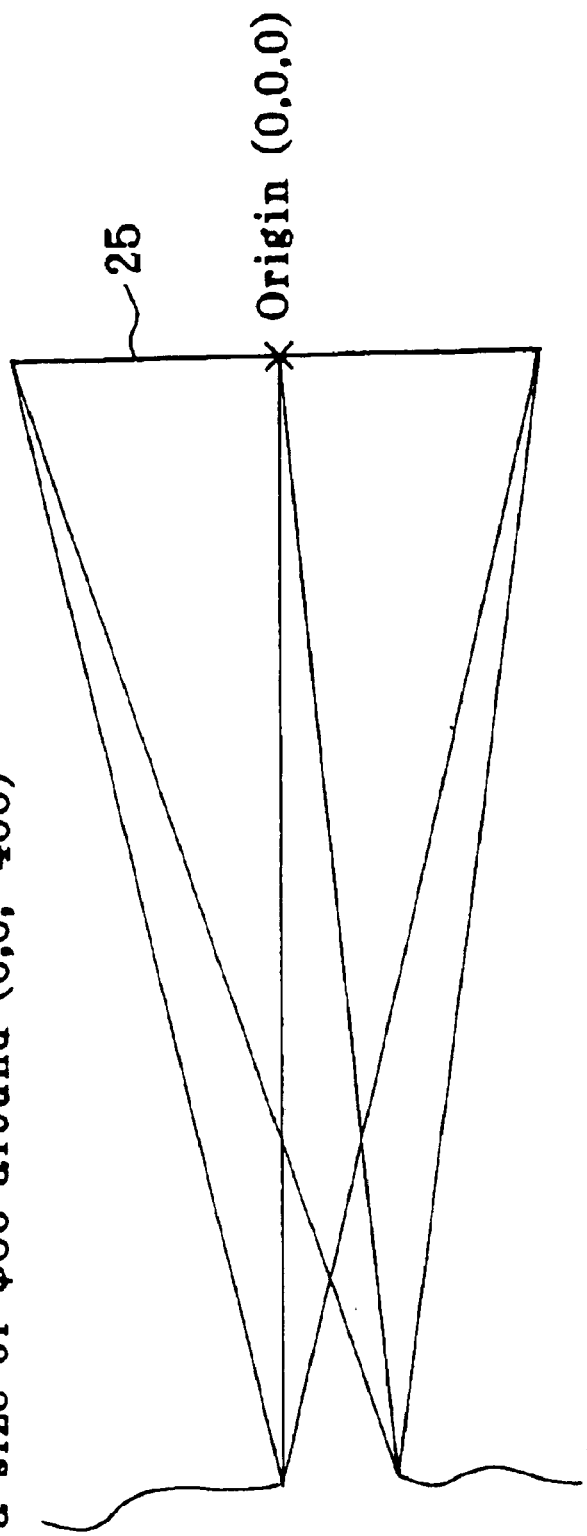
FIG. 33 is illustrative of how to fabricate a transmission hologram used as the diffusing plate in Example 9 of the invention.
Figure 34:
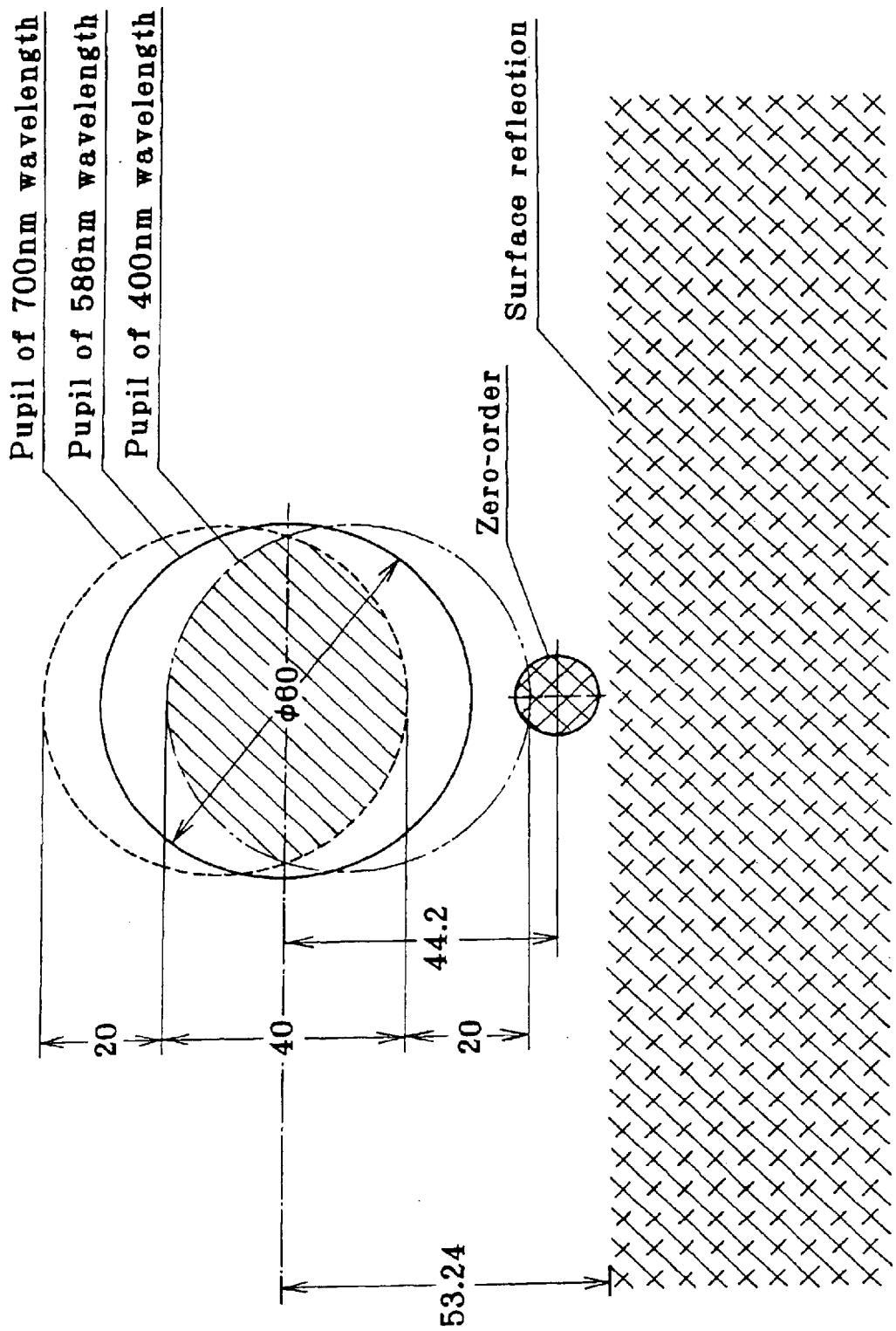
FIG. 34 is illustrative of to what degree RGB exit pupil images overlap at the position of the exit pupil of Example 9 and the positions of incidence of zero-order light and surface reflected light.

An optical path diagram in Y-Z section for this example is illustrated in FIG. 32. FIG. 33 is illustrative of how to fabricate a transmission hologram used as the diffusing plate 25 in this example. FIG. 34 is illustrative of to what degree exit pupil images overlap at the position of the exit pupil 60 in this example, and the positions of incidence of zero-order light and surface reflected light. The exit pupil images are those at 400 nm wavelength, 586 nm wavelength and 700 nm wavelength. In FIGS. 33 and 34, the numeral values are given in mm.

Example 9 corresponds to FIG. 14(a). In Example 9, the condition regarding the angle of incidence of reconstruction light is satisfied upon the second incidence, and no diffraction occurs upon the first incidence. The direction of flexion of light through the diffusing plate 25 is such that the angle of diffraction becomes small with respect to the angle of incidence to normal.

The Fresnel concave reflecting surface 24' is made up of a Fresnel back-surface mirror. Here let MY represent the amount of decentration of the Fresnel back-surface mirror, γ represent the angle of deflection of an axial chief ray 10 through the transmission hologram 25, and β represent the angle of incidence of light on the Fresnel concave reflecting mirror 24'. Then, MY=89.27 mm γ=3.76° (in a vitreous material having a refractive index of 1.49)

β=10.80° (in a vitreous material having a refractive index of 1.49)

Exposure conditions for the transmission hologram 25 in this example are illustrated in FIG. 33, wherein the origin is defined by the point of incidence of an axial chief ray 10 on the surface of the transmission hologram 25. Referring here to a coordinate system for exposure, the hologram surface is defined by an X-Y plane and a Z-axis is defined by a direction going away from the exit pupil 16 of the projection optical system 2(9).

The first light source position (X1, Y1, Z1) for exposure is determined as follows, provided that the light source is given by a point light source.

(X1, Y1, Z1)=(0, 0, −450)

The second light source position (X2, Y2, Z2) is determined as follows, provided that the second light source is given by a diffusing surface light source having an area of φ60 mm around the light source position.

(X2, Y2, Z2)=(0, −41.73, −424.62)

The transmission hologram fabricated under the above exposure conditions is used as the diffusing plate 25. After reflected at the Fresnel concave reflecting mirror 24, the light beam is diffused through the diffusing plate 25 to form a magnified pupil 60 of φ60 at the pupil plane of the viewer.

EXAMPLE 10

An optical path diagram in Y-Z section for this example is illustrated in FIG. 35. FIG. 36 is illustrative of how to fabricate a transmission hologram used as the diffusing plate 25 in this example. FIG. 37 is illustrative of to what degree exit pupil images overlap at the position of the exit pupil 60 in this example, and the positions of incidence of zero-order light and surface reflected light. The exit pupil images are those at 400 nm wavelength, 550 nm wavelength and 650 nm wavelength. In FIGS. 36 and 37, the numeral values are given in mm.

Example 10 corresponds to FIG. 13(b). In Example 10, the condition regarding the angle of incidence of reconstruction light is satisfied upon the first incidence, and no diffraction occurs upon the second incidence. The direction of flexion of light through the diffusing plate 25 is such that the angle of diffraction becomes small with respect to the angle of incidence to normal.

The Fresnel concave reflecting surface 24' is made up of a Fresnel back-surface mirror. Here let MY represent the amount of decentration of the Fresnel back-surface mirror, γ represent the angle of deflection of an axial chief ray 10 through the transmission hologram 25, and β represent the angle of incidence of light on the Fresnel concave reflecting mirror 24'. Then, MY=43.23 mm γ=15.00° (in a vitreous material having a refractive index of 1.4924)

β=3.36° (in a vitreous material having a refractive index of 1.4924)

Figures 36A, 36B, 36C:
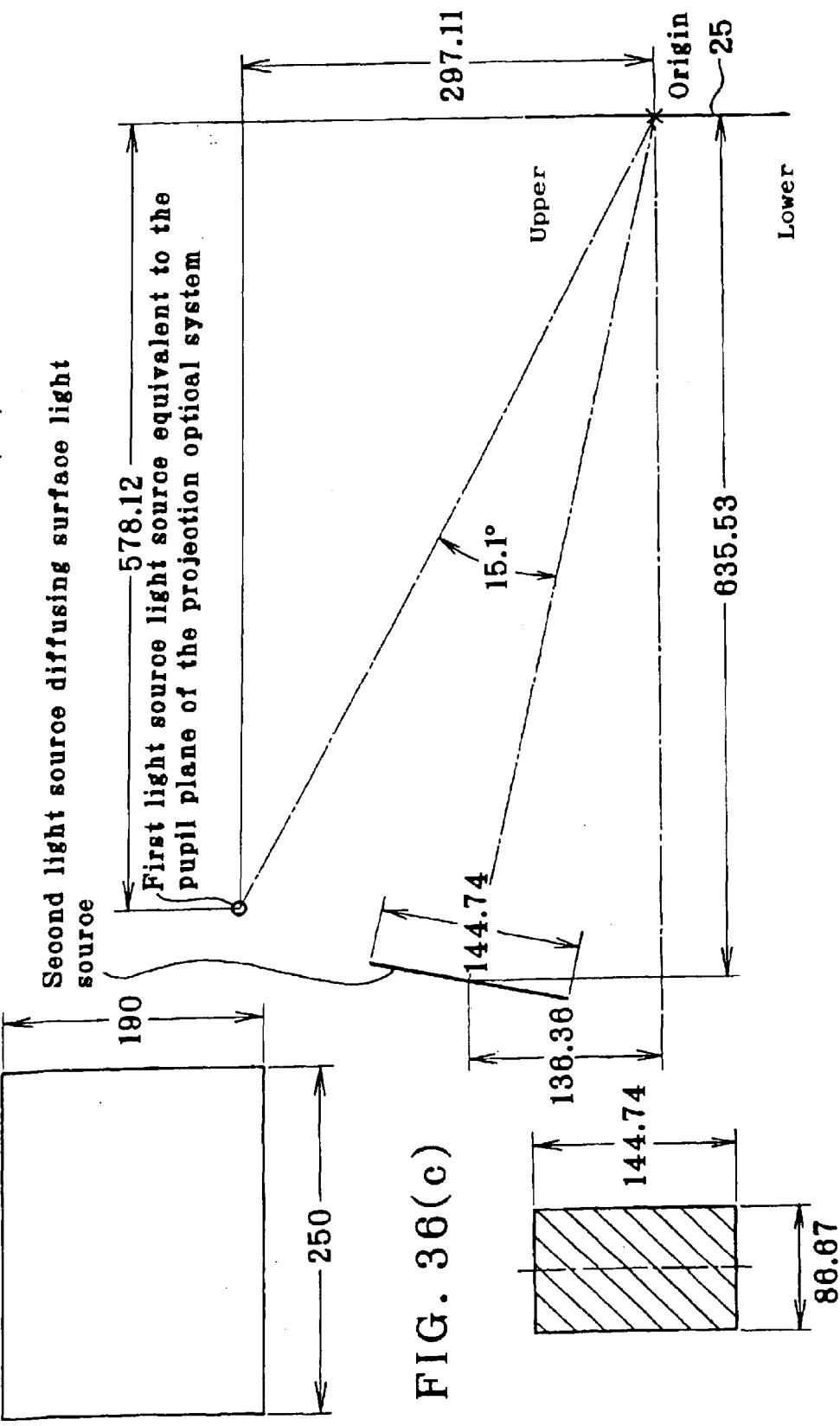
FIG. 36 is illustrative of how to fabricate a transmission hologram used as the diffusing plate in Example 10 of the invention.

Exposure conditions for the transmission hologram 25 in this example are illustrated in FIG. 36(a), wherein the origin is defined by the point of incidence of an axial chief ray 10 on the surface of the transmission hologram 25. Referring here to a coordinate system for exposure, the hologram surface is defined by an X-Y plane and a Z-axis is defined by a direction going away from the exit pupil 16 of the projection optical system 2(9).

The hologram size is shown in FIG. 36(b). As shown, a 190 mm×250 mm hologram is used.

The first light source position (X1, Y1, Z1) for exposure is determined as follows, provided that the light source is given by a point light source.

(X1, Y1, Z1)=(0, 297.11, −578.12)

The second light source position (X2, Y2, Z2) is determined as follows, provided that the second light source is given by a diffusing surface light source having an area of 144.74 mm×86.67 mm, as shown in FIG. 36(c).

(X2, Y2, Z2)=(0, 136.36, −635.53)

The transmission hologram fabricated under the above exposure conditions is used as the diffusing plate 25. After diffused through the diffusing plate 25, the light beam is reflected at the Fresnel concave reflecting mirror 24' to form a magnified pupil 60 of 60 mm×60 mm square, as shown in FIG. 37. This range ensures an exit pupil range wherein images can be viewed, with good color reproducibility, on the pupil plane of the viewer, and a circular pupil of φ60 can be obtained.

In the instant example, the chromatic aberration of the pupil is 40.2 mm. It is noted that this chromatic aberration stems from a displacement between the exit pupil image of 450 nm wavelength and the exit pupil image of 650 nm wavelength.

It is here noted that when the transmission hologram 25 is fabricated by exposure, a rectangular diffusing surface light source is used, and the exit pupil 60 is of square shape. This is preferable because the range wherein the viewer can view a displayed image with good color reproducibility is wider than achieved with a circular pupil. The same will hold true for Examples 11 to 13.

EXAMPLE 11

An optical path diagram in Y-Z section for this example is illustrated in FIG. 38. FIG. 39 is illustrative of how to fabricate a transmission hologram used as the diffusing plate 25 in this example. FIG. 40 is illustrative of to what degree exit pupil images overlap at the position of the exit pupil 60 in this example, and the positions of incidence of zero-order light and surface reflected light. The exit pupil images are those at 400 nm wavelength, 550 nm wavelength and 650 nm wavelength. In FIGS. 39 and 40, the numeral values are given in mm.

Example 11 corresponds to FIG. 14(a). In Example 11, the condition regarding the angle of incidence of reconstruction light is satisfied upon the second incidence, and no diffraction occurs upon the first incidence. The direction of flexion of light through the diffusing plate 25 is such that the angle of diffraction becomes small with respect to the angle of incidence to normal.

The Fresnel concave reflecting surface 24' is made up of a Fresnel back-surface mirror. Here let MY represent the amount of decentration of the Fresnel back-surface mirror, γ represent the angle of deflection of an axial chief ray 10 through the transmission hologram 25, and β represent the angle of incidence of light on the Fresnel concave reflecting mirror 24'. Then, MY=49.77 mm γ=12.30° (in a vitreous material having a refractive index of 1.4924)

β=12.60° (in a vitreous material having a refractive index of 1.4924)

Figure 39A:
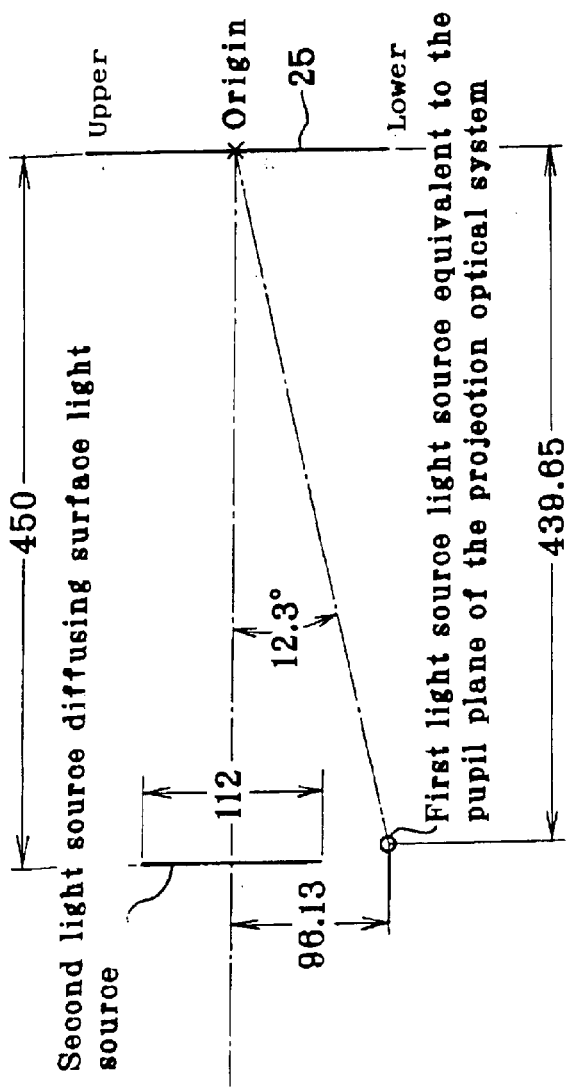
FIG. 39 is illustrative of how to fabricate a transmission hologram used as the diffusing plate in Example 11 of the invention.

Exposure conditions for the transmission hologram 25 in this example are illustrated in FIG. 39(a), wherein the origin is defined by the point of incidence of an axial chief ray 10 on the surface of the transmission hologram 25. Referring here to a coordinate system for exposure, the hologram surface is defined by an X-Y plane and a Z-axis is defined by a direction going away from the exit pupil 16 of the projection optical system 2(9).

Figure 39B:
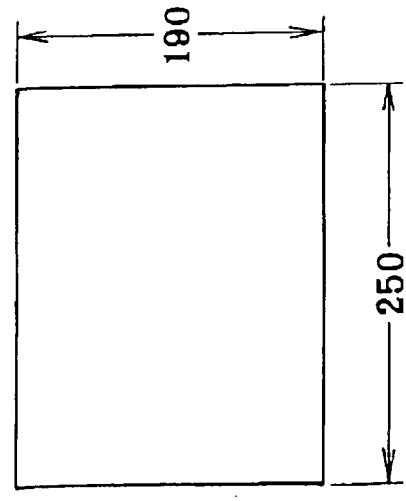

The hologram size is shown in FIG. 39(b). As shown, a 190 mm×250 mm hologram is used.

The first light source position (X1, Y1, Z1) for exposure is determined as follows, provided that the light source is given by a point light source.

(X1, Y1, Z1)=(0, −96.13, −439.65)

Figure 39C:
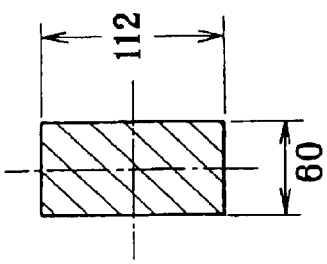

The second light source position (X2, Y2, Z2) is determined as follows, provided that the second light source is given by a diffusing surface light source having an area of 112 mm×60 mm, as shown in FIG. 39(c).

(X2, Y2, Z2)=(0, 0, −450.00)

The transmission hologram fabricated under the above exposure conditions is used as the diffusing plate 25. After reflected at the Fresnel concave reflecting mirror 24', the light beam is diffused through the diffusing plate 25 to form a magnified pupil 60 of 60 mm×60 mm square, as shown in FIG. 40. This range ensures an exit pupil range wherein images can be viewed, with good color reproducibility, on the pupil plane of the viewer, and a circular pupil of φ60 can be obtained.

In the instant example, the chromatic aberration of the pupil is 52 mm. It is noted that this chromatic aberration stems from a displacement between the exit pupil image of 450 nm wavelength and the exit pupil image of 650 nm wavelength.

EXAMPLE 12

Figure 41:
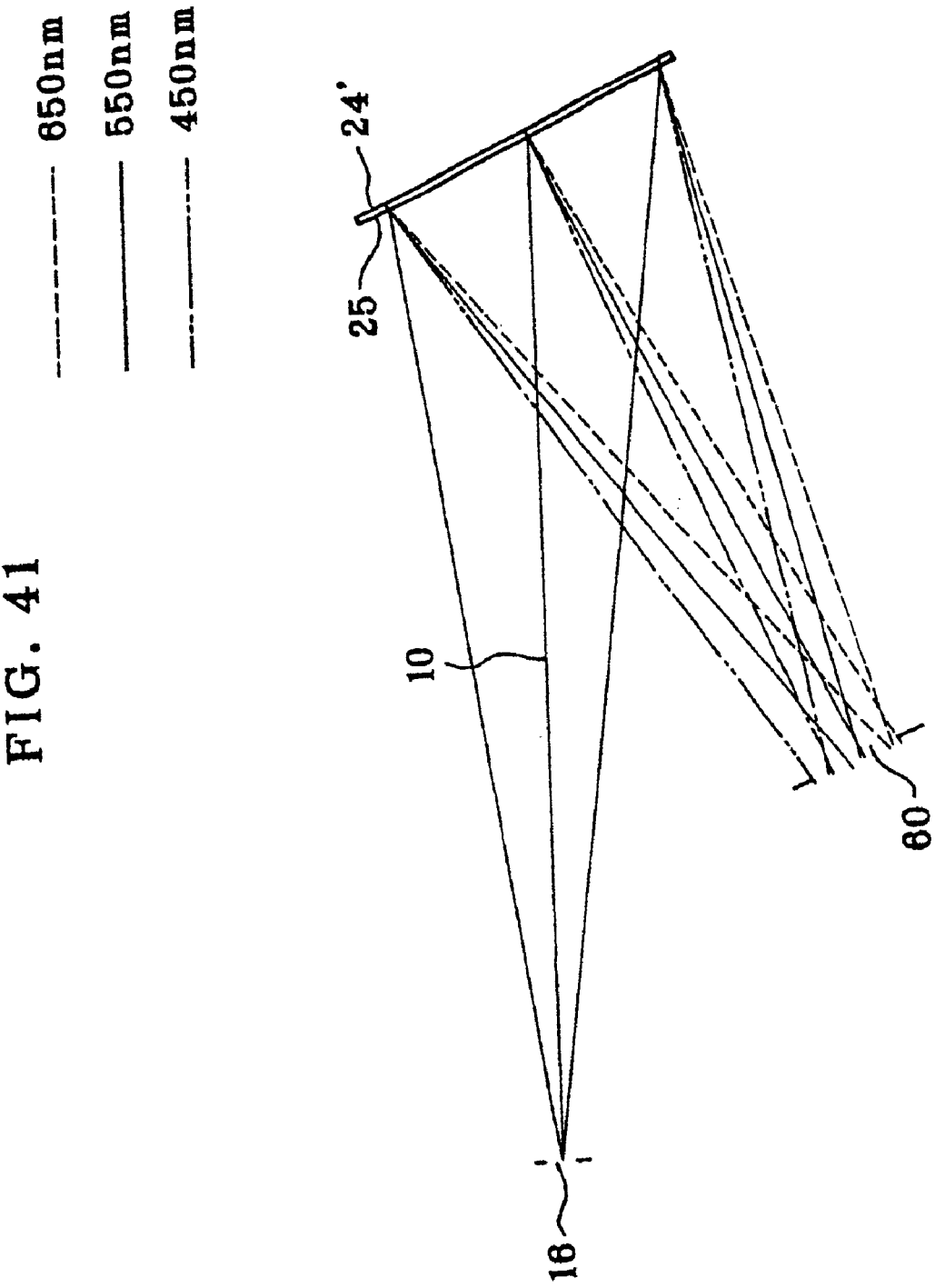
FIG. 41 is an optical path diagram illustrative in Y-Z section of Example 12 of the invention.

An optical path diagram in Y-Z section for this example is illustrated in FIG. 41. FIG. 42 is illustrative of how to fabricate a transmission hologram used as the diffusing plate 25 in this example. FIG. 43 is illustrative of to what degree exit pupil images overlap at the position of the exit pupil 60 in this example, and the positions of incidence of zero-order light and surface reflected light. The exit pupil images are those at 400 nm wavelength, 550 nm wavelength and 650 nm wavelength. In FIGS. 42 and 43, the numeral values are given in mm.

Example 12 corresponds to FIG. 13(c). In Example 12, the condition regarding the angle of incidence of reconstruction light is satisfied upon the first incidence, and no diffraction occurs upon the second incidence. The direction of flexion of light through the diffusing plate 25 is such that the angle of diffraction becomes large with respect to the angle of incidence to normal.

The Fresnel concave reflecting surface 24' is made up of a Fresnel back-surface mirror. Here let MY represent the amount of decentration of the Fresnel back-surface mirror, γ represent the angle of deflection of an axial chief ray 10 through the transmission hologram 25, and β represent the angle of incidence of light on the Fresnel concave reflecting mirror 24'. Then, MY=157.23 mm γ=15.00° (in a vitreous material having a refractive index of 1.4924)

β=12.57° (in a vitreous material having a refractive index of 1.4924)

Figure 42A:
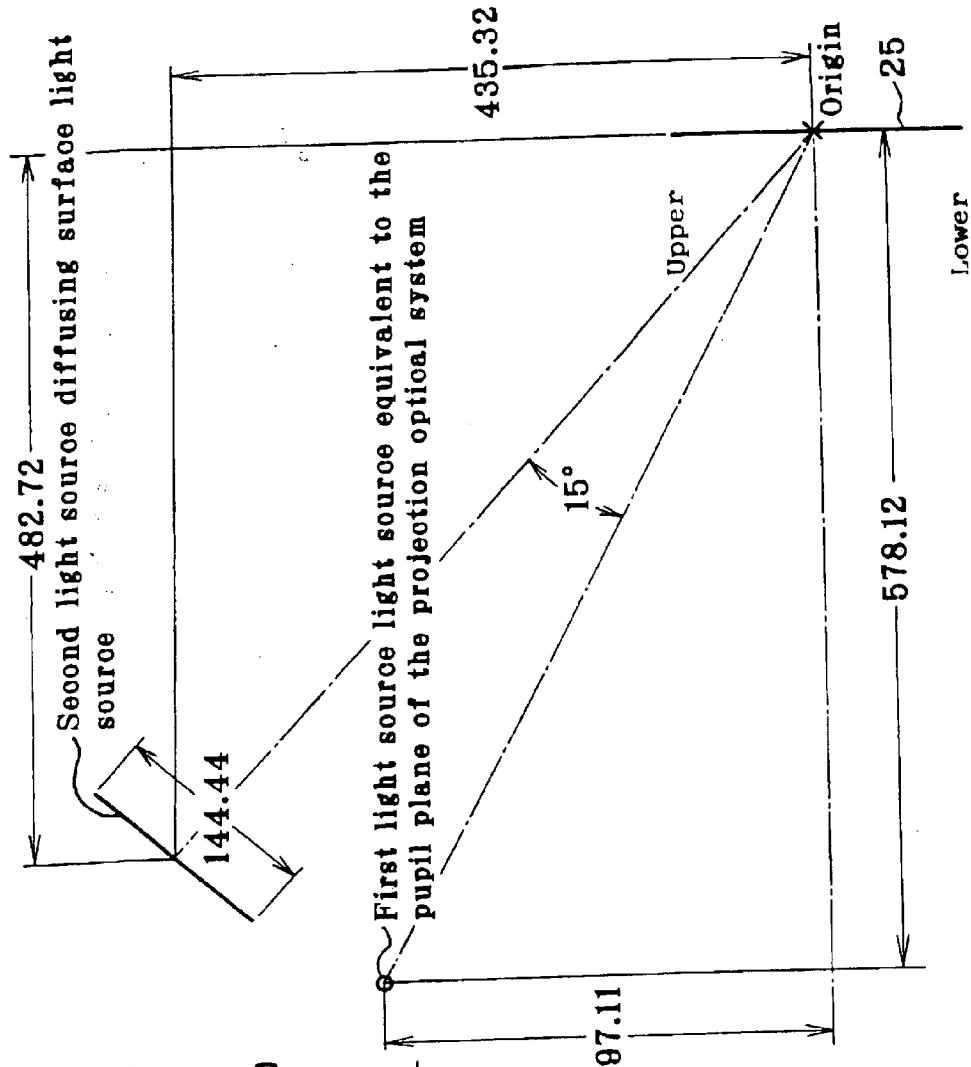
FIG. 42 is illustrative of how to fabricate a transmission hologram used as the diffusing plate in Example 12 of the invention.

Exposure conditions for the transmission hologram 25 in this example are illustrated in FIG. 42(a), wherein the origin is defined by the point of incidence of an axial chief ray 10 on the surface of the transmission hologram 25. Referring here to a coordinate system for exposure, the hologram surface is defined by an X-Y plane and a Z-axis is defined by a direction going away from the exit pupil 16 of the projection optical system 2(9).

Figure 42B:
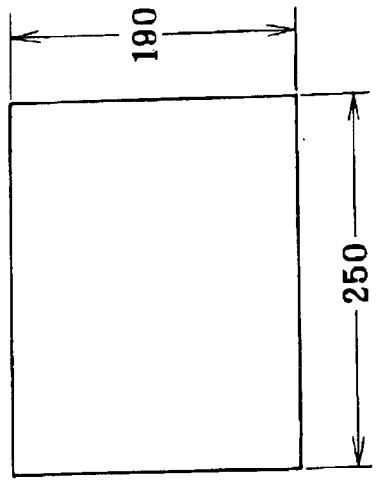

The hologram size is shown in FIG. 42(b). As shown, a 190 mm×250 mm hologram is used.

The first light source position (X1, Y1, Z1) for exposure is determined as follows, provided that the light source is given by a point light source.

(X1, Y1, Z1)=(0, 297.11, −578.12)

Figure 42C:
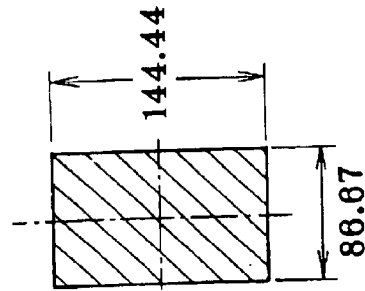

The second light source position (X2, Y2, Z2) is determined as follows, provided that the second light source is given by a diffusing surface light source having an area of 144.44 mm×86.67 mm, as shown in FIG. 42(c).

(X2, Y2, Z2)=(0, 435.32, −482.72)

The transmission hologram fabricated under the above exposure conditions is used as the diffusing plate 25. After diffused through the diffusing plate 25, the light beam is reflected at the Fresnel concave reflecting mirror 24' to form a magnified pupil 60 of 60 mm×60 mm square, as shown in FIG. 40. This range ensures an exit pupil range wherein images can be viewed, with good color reproducibility, on the pupil plane of the viewer, and a circular pupil of φ60 can be obtained.

In the instant example, the chromatic aberration of the pupil is 40 mm. It is noted that this chromatic aberration stems from a displacement between the exit pupil image of 450 nm wavelength and the exit pupil image of 650 nm wavelength.

EXAMPLE 13

Figure 44:
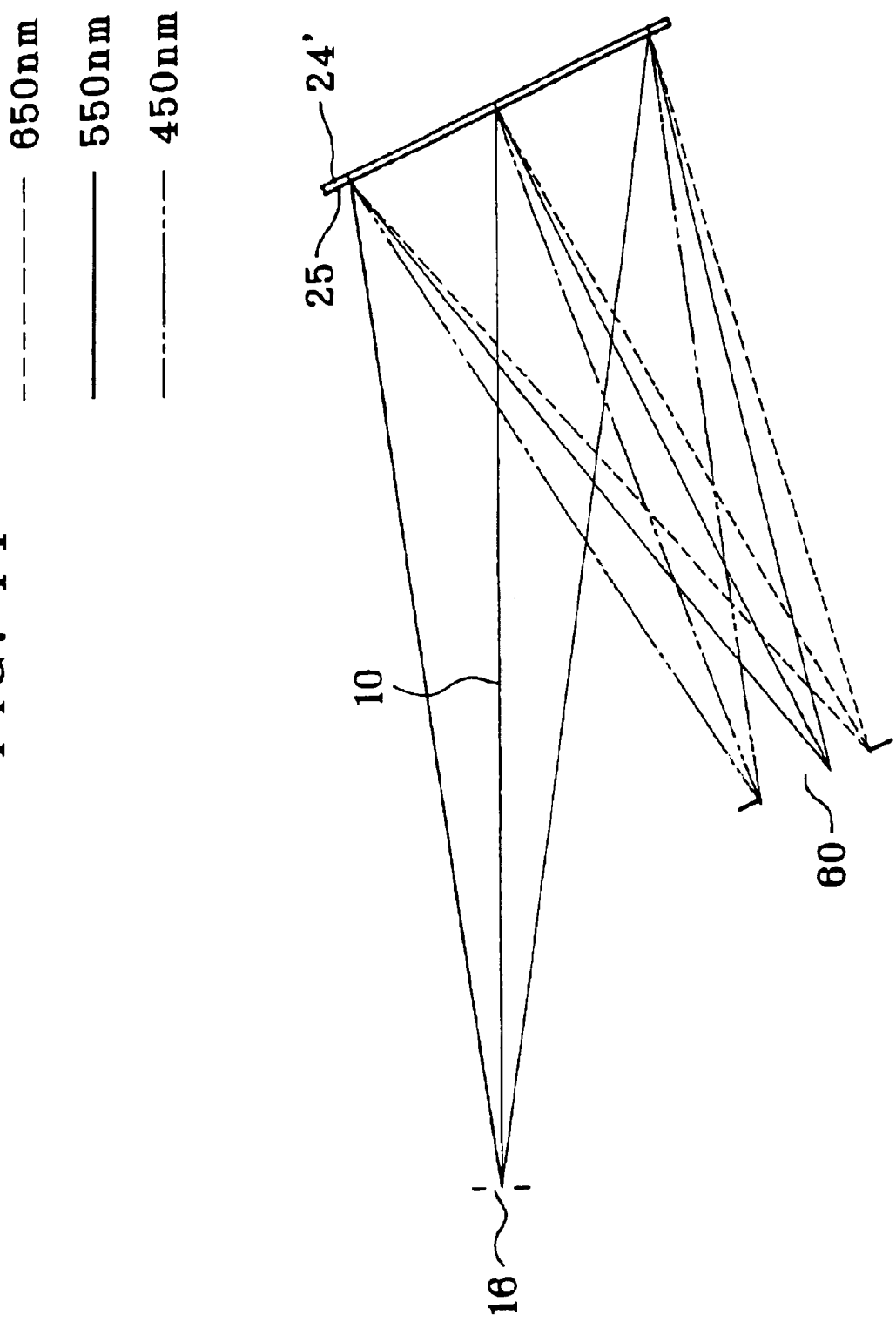
FIG. 44 is an optical path diagram illustrative in Y-Z section of Example 13 of the invention.

An optical path diagram in Y-Z section for this example is illustrated in FIG. 44. FIG. 45 is illustrative of how to fabricate a transmission hologram used as the diffusing plate 25 in this example. FIG. 46 is illustrative of to what degree exit pupil images overlap at the position of the exit pupil 60 in this example, and the positions of incidence of zero-order light and surface reflected light. The exit pupil images are those at 400 nm wavelength, 550 nm wavelength and 650 nm wavelength. In FIGS. 45 and 46, the numeral values are given in mm.

Example 13 corresponds to FIG. 14(b). In Example 13, the condition regarding the angle of incidence of reconstruction light is satisfied upon the second incidence, and no diffraction occurs upon the first incidence. The direction of flexion of light through the diffusing plate 25 is such that the angle of diffraction becomes large with respect to the angle of incidence to normal.

The Fresnel concave reflecting surface 24' is made up of a Fresnel back-surface mirror. Here let MY represent the amount of decentration of the Fresnel back-surface mirror, γ represent the angle of deflection of an axial chief ray 10 through the transmission hologram 25, and β represent the angle of incidence of light on the Fresnel concave reflecting mirror 24'. Then, MY=171.54 mm γ=15.00° (in a vitreous material having a refractive index of 1.4924)

β=2.88° (in a vitreous material having a refractive index of 1.4924)

Exposure conditions for the transmission hologram 25 in this example are illustrated in FIG. 45(a), wherein the origin is defined by the point of incidence of an axial chief ray 10 on the surface of the transmission hologram 25. Referring here to a coordinate system for exposure, the hologram surface is defined by an X-Y plane and a Z-axis is defined by a direction going away from the exit pupil 16 of the projection optical system 2(9).

The hologram size is shown in FIG. 45(b). As shown, a 190 mm×250 mm hologram is used.

The first light source position (X1, Y1, Z1) for exposure is determined as follows, provided that the light source is given by a point light source.

(X1, Y1, Z1)=(0, 116.62, −434.63)

The second light source position (X2, Y2, Z2) is determined as follows, provided that the second light source is given by a diffusing surface light source having an area of 128 mm×60 mm, as shown in FIG. 45(c).

(X2, Y2, Z2)=(0, 0, −450.00)

The transmission hologram fabricated under the above exposure conditions is used as the diffusing plate 25. After reflected at the Fresnel concave reflecting mirror 24', the light beam is diffused through the diffusing plate 25 to form a magnified pupil 60 of 60 mm×60 mm square, as shown in FIG. 46. This range ensures an exit pupil range wherein images can be viewed, with good color reproducibility, on the pupil plane of the viewer, and a circular pupil of φ60 can be obtained.

In the instant example, the chromatic aberration of the pupil is 68 mm. It is noted that this chromatic aberration stems from a displacement between the exit pupil image of 450 nm wavelength and the exit pupil image of 650 nm wavelength.

In Examples 6–9, at the position of the exit pupil 60 of the system, the difference in the position of incidence between the optical axis of 700 nm wavelength and the optical axis of 400 nm wavelength is not greater than ½ of the diameter of the exit pupil. In other words, the range where RGB pupils overlap is kept wide, and any incidence of zero-order light and surface reflected light at the hologram does not occur within that range. It follows that there is ensured a wide exit pupil range where images can be viewed with high color reproducibility, as can be seen from FIGS. 25, 28, 31 and 34.

In Examples 10–13, at the position of the exit pupil 60 of the system, the difference (chromatic aberration) in the position of incidence between the optical axis of 650 nm wavelength and the optical axis of 650 nm wavelength is not greater than ½ of the diameter of the exit pupil. In other words, the (60 mm×60 mm square) range where RGB pupils overlap is kept wide, and any incidence of zero-order light and surface reflected light at the hologram does not occur within that range. It follows that there is ensured a wide exit pupil range where images can be viewed with high color reproducibility, as can be seen from FIGS. 37, 40, 43 and 46.

It is noted that in Examples 10–13, the position of incidence of zero-order light is spaced more away from the magnified pupil 60 than in Examples 6–9.

Construction parameters in Examples 1–13 are set out below. As mentioned above, the axial chief ray 10 in Examples 1–3 is defined by a light ray that leaves the center of the object plane 11 and passes through the center of a stop surface (that is located at the position of the entrance surface of the eyepiece optical system 4), arriving at the center of the image plane 12. The axial chief ray 10 in Examples 4–5 is defined by a light ray that leaves the center of the light source 7 and passes through the center of the scanning mirror 80 forming the pupil of the optical system, arriving at the scanning surface 40. The axial chief ray 10 in Examples 6–13 is defined by a light ray that leaves the center of the exit pupil 16 (the projection optical system 2(9)) and passes through the center of the diffusing plate 25, arriving at the center of the exit pupil 60 of the system.

In Examples 1–3, back ray tracing is carried out with the origin defined by the center of the stop surface. An X-Y plane is defined by the stop surface, a Z-axis direction is defined by a direction vertical to the stop surface, and a Z-axis positive direction is defined by a direction toward the back surface of the eyepiece optical system 4. In Examples 4–5, normal ray tracing is carried out with the origin defined by the center of the light source 7. A Z-axis positive direction is defined by the direction of propagation of the axial chief ray 10, and a Y-Z plane is defined by the decentered surface of the projection optical system 9. In Examples 6–13, normal ray tracing is carried out with the origin defined by the center of the exit pupil 16 of the projection optical system 2(9). An X-Y plane is defined by the pupil plane, and a Z-axis positive direction is defined by the direction of propagation of the axial chief ray 10 vertical to the pupil.

For the decentered surface, there are given the amount of decentration of its apex from the origin of the optical system and the angles of inclination of its center axis around the X-, Y- and Z-axes ($\alpha$, $\beta$, $\gamma$(°)).

Here the amounts of decentration in the X-, Y- and Z-axis directions are referred to as X, Y and Z. The center axis is defined by the Z-axis of the aforesaid formula (a) for the free-form surface, the Z-axis of the following formula (b) for the aspheric surface, and the Z-axis of the following formula (c) for the anamorphic surface.

In that case, the positive for $\alpha$ and $\beta$ means counterclockwise rotation with respect to the positive direction of the respective axes, and the positive for $\gamma$ means clockwise rotation with respect to the positive direction of the Z-axis. For $\alpha$, $\beta$ and $\gamma$ rotation of the center axis of the surface, the center axis of the surface and its XYZ orthogonal coordinate system are first counterclockwise rotated around the X-axis by $\alpha$. Then, the center axis of the rotated surface is counterclockwise rotated around the Y-axis of a new coordinate system by $\beta$ while the once rotated coordinate system is counterclockwise rotated around the Y-axis by $\gamma$. Then, the center axis of the twice rotated surface is clockwise rotated around the Z-axis of a new coordinate system by $\gamma$.

The surface shape of the free-form surface used herein, for instance, is defined by formula (a) in Patent Publication 7 (Patent Publication 8), and the Z-axis of the defining formula (a) gives the axis of the free-form surface.

The aspheric surface is a rotationally symmetric aspheric surface given by the following defining formula:

$$Z=(Y^2/R)/[1+\{1-(1+K)Y^2/R^2\}^{1/2}]+AY^4+BY^6+CY^8+DY^{10}+ \quad (b)$$

where Z is an optical axis (axial chief ray) provided that the direction of propagation of light is positive, and Y is in the direction vertical to the optical axis. Here R is a paraxial radius of curvature, K is a conical constant, and A, B, C, D, . . . are the 4th, 6th, 8th and 10th aspheric coefficients.

The shape of the anamorphic surface is given by the following formula while the axis of the anamorphic surface is defined by a straight line that passes through the origin of the surface shape and is vertical to the optical surface.

$$Z=(CxX^2+Cy\cdot Y^2)/[1+\{1-(1+Kx)Cx^2\cdot X^2-(1+Ky)Cy^2\cdot Y^2\}^{1/2}]+ \Sigma Rn\{(1-Pn)X^2+(1+Pn)Y^2\}^{(n+1)}$$

Here, consider n=4 (fourth-order term) as an example. Upon extended, Z is given by the following formula (c).

$$Z = (Cx\cdot X^2 + Cy\cdot Y^2)/ \quad (c)$$
$$\left[1 + \{1 - (1 + Kx)Cx^2 \cdot X^2 - (1 + Ky)Cy^2 \cdot Y^2\}^{\frac{1}{2}}\right] +$$
$$R1\{(1-P1)X^2 + (1+P1)Y^2\}^2 + R2$$
$$\{(1-P2)X^2 + (1+P2)Y^2\}^3 + R3\{(1-P3)X^2 + (1+P3)Y^2\}^4 +$$
$$R4\{(1-P4)X^2 + (1+P4)Y^2\}^5$$

Here Z is the amount of displacement of the surface shape from a tangent plane to the origin, Cx is a curvature in the X-axis direction, Cy is a curvature in the Y-axis direction, Kx is a conical coefficient in the X-axis direction, Ky is a conical coefficient in the Y-axis direction, Rn is a rotationally symmetric component of the aspheric term, and Pn is a rotationally asymmetric component of the aspheric term. It is noted that among the radius of curvature Rx in the X-axis direction, the radius of curvature Ry in the Y-axis direction and the curvatures Cx and Cy there is the following relation:

$$Rx=1/Cx,\ Ry=1/Cy$$

It is noted that the term regarding free-form surfaces on which no data is give is zero. Refractive indexes are given on a d-line basis (587.56 nm). Length is given in mm.

Construction parameters for Examples 1–13 are set out below. In what follows, "FFS", "ASS", "ANM", "FL", "RE", "SM", "HOE" and "PIM" represent a free-form surface, an aspheric surface, an anamorphic surface, a Fresnel surface, a reflecting surface, a scanning mirror, a transmission hologram and an image projection surface, respectively.

EXAMPLE 1

| Surface No. | Radius of curvature | Surface separation | Displacement and tilt | Refractive index | Abbe's No. |
|---|---|---|---|---|---|
| Object plane | ∞ | | (1) | | |
| 1 | ANM(1) (Stop, RE) | | | | |
| Image plane | ∞ | | (2) | | |

| ANM(1) | |
|---|---|
| Rx | −502.13 |
| Kx | 1.0632 × 10$^{+1}$ |
| R1 | 5.3570 × 10$^{−1}$ |
| R2 | 6.9470 × 10$^{−1}$ |
| Ry | −399.96 |
| Ky | 1.0632 × 10$^{+1}$ |
| P1 | 1.0015 × 10$^{−8}$ |
| P2 | 1.9188 × 10$^{−13}$ |

| Displacement and tilt(1) | | | | | |
|---|---|---|---|---|---|
| X | −500.00 | Y | 150.38 | Z | −852.87 |
| α | −10.00 | β | −30.00 | γ | 0.00 |

| Displacement and tilt(2) | | | | | |
|---|---|---|---|---|---|
| X | 150.00 | Y | −45.12 | Z | −255.86 |
| α | 10.00 | β | 30.00 | γ | 0.00 |

EXAMPLE 2

| Surface No. | Radius of curvature | Surface separation | Displacement and tilt | Refractive index | Abbe's No. |
|---|---|---|---|---|---|
| Object plane | ∞ | | (1) | | |
| 1 | FFS(1) (Stop, RE) | | | | |
| Image plane | ∞ | | (2) | | |

FFS(1)

| $C_4$ | $-9.4100 \times 10^{-4}$ | $C_6$ | $-1.2455 \times 10^{-3}$ |
|---|---|---|---|

Displacement and tilt(1)

| X | −500.00 | Y | 150.38 | Z | −852.87 |
|---|---|---|---|---|---|
| α | −10.00 | β | −30.00 | γ | 0.00 |

Displacement and tilt(2)

| X | 150.00 | Y | −45.12 | Z | −255.86 |
|---|---|---|---|---|---|
| α | 10.00 | β | 30.00 | γ | 0.00 |

EXAMPLE 3

| Surface No. | Radius of curvature | Surface separation | Displacement and tilt | Refractive index | Abbe's No. |
|---|---|---|---|---|---|
| Object plane | ∞ | | (1) | | |
| 1 | ∞ (Stop) | | | 1.5163 | 64.1 |
| 2 | ASS(1) (RE, FL) | | (2) | 1.5163 | 64.1 |
| 3 | ∞ | | | | |
| Image plane | ∞ | | (3) | | |

ASS(1)

| R | −1039.03 |
|---|---|
| K | $9.3942 \times 10^{+1}$ |
| A | $-4.0647 \times 10^{-8}$ |
| B | $5.7192 \times 10^{-12}$ |

Displacement and tilt(1)

| X | −500.00 | Y | 150.38 | Z | −852.87 |
|---|---|---|---|---|---|
| α | −10.00 | β | −30.00 | γ | 0.00 |

Displacement and tilt(2)

| X | 0.00 | Y | −0.07 | Z | 2.00 |
|---|---|---|---|---|---|
| α | −0.49 | β | 0.00 | γ | 0.00 |

Displacement and tilt(3)

| X | 150.00 | Y | −45.12 | Z | −255.86 |
|---|---|---|---|---|---|
| α | 10.00 | β | 30.00 | γ | 0.00 |

EXAMPLE 4

| Surface No. | Radius of curvature | Surface separation | Displacement and tilt | Refractive index | Abbe's No. |
|---|---|---|---|---|---|
| Object plane | ∞ | | | | |
| 1 | 1.36 | | (1) | 1.5163 | 64.1 |
| 2 | ASS(1) | | (2) | | |
| 3 | ∞ (Stop, SM) | | (3) | | |
| 4 | FFS(1) (RE) | | (4) | | |
| 5 | FFS(2) (RE) | | (5) | | |
| Image plane | ∞ | | (6) | | |

ASS(1)

| R | ∞ |
|---|---|
| K | $-6.4654 \times 10^{+6}$ |
| A | $1.4044 \times 10^{-1}$ |
| B | $-2.8953 \times 10^{-1}$ |

FFS(1)

| $C_4$ | $-7.9957 \times 10^{-3}$ | $C_6$ | $-1.5691 \times 10^{-2}$ | $C_8$ | $-8.7517 \times 10^{-3}$ |
|---|---|---|---|---|---|
| $C_{10}$ | $-9.2783 \times 10^{-4}$ | $C_{11}$ | $-8.7817 \times 10^{-4}$ | $C_{13}$ | $-5.7719 \times 10^{-4}$ |
| $C_{15}$ | $-3.5738 \times 10^{-5}$ | | | | |

FFS(2)

| $C_4$ | $-9.5591 \times 10^{-3}$ | $C_6$ | $-1.0370 \times 10^{-2}$ | $C_8$ | $-1.0324 \times 10^{-3}$ |
|---|---|---|---|---|---|
| $C_{10}$ | $-2.0894 \times 10^{-4}$ | $C_{11}$ | $-6.6411 \times 10^{-6}$ | $C_{13}$ | $-1.7961 \times 10^{-5}$ |
| $C_{15}$ | $-2.8612 \times 10^{-6}$ | | | | |

Displacement and tilt(1)

| X | 0.00 | Y | 0.00 | Z | 2.80 |
|---|---|---|---|---|---|
| α | 0.00 | β | 0.00 | γ | 0.00 |

Displacement and tilt(2)

| X | 0.00 | Y | 0.00 | Z | 3.80 |
|---|---|---|---|---|---|
| α | 0.00 | β | 0.00 | γ | 0.00 |

Displacement and tilt(3)

| X | 0.00 | Y | 0.00 | Z | 5.80 |
|---|---|---|---|---|---|
| α | 45.00 | β | 0.00 | γ | 0.00 |

Displacement and tilt(4)

| X | 0.00 | Y | −2.00 | Z | 5.80 |
|---|---|---|---|---|---|
| α | −45.00 | β | 0.00 | γ | 0.00 |

Displacement and tilt(5)

| X | 0.00 | Y | −2.00 | Z | 8.00 |
|---|---|---|---|---|---|
| α | −45.00 | β | 0.00 | γ | 0.00 |

Displacement and tilt(6)

| X | 0.00 | Y | −292.00 | Z | 8.00 |
|---|---|---|---|---|---|
| α | 0.00 | β | 0.00 | γ | 0.00 |

EXAMPLE 5

| Surface No. | Radius of curvature | Surface separation | Displacement and tilt | Refractive index | Abbe's No. |
|---|---|---|---|---|---|
| Object plane | ∞ | | | | |
| 1 | −4.6344 | | (1) | 1.5163 | 64.1 |
| 2 | ASS(1) | | (2) | | |
| 3 | ∞ (Stop, SM) | | (3) | | |
| 4 | ∞ | | (4) | 1.5163 | 64.1 |
| 5 | FFS(1) (RE) | | (5) | 1.5163 | 64.1 |
| 6 | FFS(2) (RE) | | (6) | 1.5163 | 64.1 |
| 7 | ∞ | | (7) | | |
| Image plane | ∞ | | (8) | | |

-continued

ASS(1)

| | | |
|---|---|---|
| R | | −1.06 |
| K | | −5.4859 × $10^{-1}$ |
| A | | 2.2734 × $10^{-2}$ |
| B | | 5.2264 × $10^{-3}$ |

FFS(1)

| | | | | | |
|---|---|---|---|---|---|
| $C_4$ | −7.3742 × $10^{-2}$ | $C_6$ | −1.3926 × $10^{-1}$ | $C_8$ | −1.2695 × $10^{-2}$ |
| $C_{10}$ | 1.3989 × $10^{-3}$ | $C_{11}$ | −1.1007 × $10^{-2}$ | $C_{13}$ | −6.4887 × $10^{-2}$ |
| $C_{15}$ | −7.2394 × $10^{-3}$ | | | | |

FFS(2)

| | | | | | |
|---|---|---|---|---|---|
| $C_4$ | 2.5914 × $10^{-1}$ | $C_6$ | −1.4332 × $10^{-2}$ | $C_8$ | −1.1310 × $10^{-2}$ |
| $C_{10}$ | −2.9605 × $10^{-4}$ | $C_{11}$ | 3.4328 × $10^{-4}$ | $C_{13}$ | −2.9433 × $10^{-2}$ |
| $C_{15}$ | −2.0034 × $10^{-4}$ | | | | |

Displacement and tilt(1)

| X | 0.00 | Y | 0.00 | Z | 2.80 |
|---|---|---|---|---|---|
| α | 0.00 | β | 0.00 | γ | 0.00 |

Displacement and tilt(2)

| X | 0.00 | Y | 0.00 | Z | 3.80 |
|---|---|---|---|---|---|
| α | 0.00 | β | 0.00 | γ | 0.00 |

Displacement and tilt(3)

| X | 0.00 | Y | 0.00 | Z | 5.80 |
|---|---|---|---|---|---|
| α | 45.00 | β | 0.00 | γ | 0.00 |

Displacement and tilt(4)

| X | 0.00 | Y | −1.00 | Z | 5.80 |
|---|---|---|---|---|---|
| α | 90.00 | β | 0.00 | γ | 0.00 |

Displacement and tilt(5)

| X | 0.00 | Y | −6.00 | Z | 5.80 |
|---|---|---|---|---|---|
| α | 112.50 | β | 0.00 | γ | 0.00 |

Displacement and tilt(6)

| X | 0.00 | Y | −4.00 | Z | 3.80 |
|---|---|---|---|---|---|
| α | 157.50 | β | 0.00 | γ | 0.00 |

Displacement and tilt(7)

| X | 0.00 | Y | −4.00 | Z | 7.80 |
|---|---|---|---|---|---|
| α | 0.00 | β | 0.00 | γ | 0.00 |

Displacement and tilt(8)

| X | 0.00 | Y | −4.00 | Z | 288.86 |
|---|---|---|---|---|---|
| α | 0.00 | β | 0.00 | γ | 0.00 |

EXAMPLE 6

| Surface No. | Radius of curvature | Surface separation | Displacement and tilt | Refractive index | Abbe's No. |
|---|---|---|---|---|---|
| Object plane | ∞ | | | | |
| 1 | HOE | | (1) | 1.49 | 57.4 |
| 2 | ∞ (PIM) | | (2) | 1.49 | 57.4 |
| 3 | ASS(1) (RE, FL) | | (3) | 1.49 | 57.4 |
| 4 | ∞ | | (1) | | |
| Image plane | ∞ | | (4) | | |

ASS(1)

| | | |
|---|---|---|
| R | | −816.43 |
| K | | −2.0000 × $10^{-6}$ |
| A | | 1.4845 × $10^{-11}$ |
| B | | −5.8165 × $10^{-15}$ |
| C | | 2.3649 × $10^{-19}$ |
| D | | −1.5631 × $10^{-24}$ |

Displacement and tilt(1)

| X | 0.00 | Y | 0.00 | Z | 650.00 |
|---|---|---|---|---|---|
| α | 27.2 | β | 0.00 | γ | 0.00 |

Displacement and tilt(2)

| X | 0.00 | Y | 0.46 | Z | 650.89 |
|---|---|---|---|---|---|
| α | 27.2 | β | 0.00 | γ | 0.00 |

Displacement and tilt(3)

| X | 0.00 | Y | MY | Z | 604.70 |
|---|---|---|---|---|---|
| α | 27.2 | β | 0.00 | γ | 0.00 |

Displacement and tilt(4)

| X | 0.00 | Y | −205.69 | Z | 249.76 |
|---|---|---|---|---|---|
| α | 27.2 | β | 0.00 | γ | 0.00 |

EXAMPLE 7

| Surface No. | Radius of curvature | Surface separation | Displacement and tilt | Refractive index | Abbe's No. |
|---|---|---|---|---|---|
| Object plane | ∞ | | | | |
| 1 | HOE | | (1) | 1.49 | 57.4 |
| 2 | ∞ (PIM) | | (2) | 1.49 | 57.4 |
| 3 | ASS(1) (RE, FL) | | (3) | 1.49 | 57.4 |
| 4 | ∞ | | (1) | | |
| Image plane | ∞ | | (4) | | |

ASS(1)

| | | |
|---|---|---|
| R | | −816.43 |
| K | | −2.0000 × $10^{-6}$ |
| A | | 1.4845 × $10^{-11}$ |
| B | | −5.8165 × $10^{-15}$ |
| C | | 2.3649 × $10^{-19}$ |
| D | | −1.5631 × $10^{-24}$ |

Displacement and tilt(1)

| X | 0.00 | Y | 0.00 | Z | 650.00 |
|---|---|---|---|---|---|
| α | 27.2 | β | 0.00 | γ | 0.00 |

Displacement and tilt(2)

| X | 0.00 | Y | 0.46 | Z | 650.89 |
|---|---|---|---|---|---|
| α | 27.2 | β | 0.00 | γ | 0.00 |

Displacement and tilt(3)

| X | 0.00 | Y | MY | Z | 584.08 |
|---|---|---|---|---|---|
| α | 27.2 | β | 0.00 | γ | 0.00 |

Displacement and tilt(4)

| X | 0.00 | Y | −205.69 | Z | 249.76 |
|---|---|---|---|---|---|
| α | 27.2 | β | 0.00 | γ | 0.00 |

EXAMPLE 8

| Surface No. | Radius of curvature | Surface separation | Displacement and tilt | Refractive index | Abbe's No. |
|---|---|---|---|---|---|
| Object plane | ∞ | | | | |
| 1 | HOE | | (1) | 1.62 | 23.9 |
| 2 | ∞ (PIM) | | (2) | 1.62 | 23.9 |

-continued

| | | | | | |
|---|---|---|---|---|---|
| 3 | ASS(1) (RE, FL) | | (3) | 1.62 | 23.9 |
| 4 | ∞ | | (1) | | |
| Image plane | ∞ | | (4) | | |

ASS(1)

| | |
|---|---|
| R | −835.62 |
| K | 0.0332 |
| A | $4.8760 \times 10^{-9}$ |
| B | $-2.5964 \times 10^{-13}$ |
| C | $6.8805 \times 10^{-18}$ |
| D | $-6.6177 \times 10^{-23}$ |

Displacement and tilt(1)

| X | 0.00 | Y | 0.00 | Z | 650.00 |
|---|---|---|---|---|---|
| α | 27.2 | β | 0.00 | γ | 0.00 |

Displacement and tilt(2)

| X | 0.00 | Y | 0.46 | Z | 650.89 |
|---|---|---|---|---|---|
| α | 27.2 | β | 0.00 | γ | 0.00 |

Displacement and tilt(3)

| X | 0.00 | Y | MY | Z | 604.54 |
|---|---|---|---|---|---|
| α | 27.2 | β | 0.00 | γ | 0.00 |

Displacement and tilt(4)

| X | 0.00 | Y | −205.69 | Z | 249.76 |
|---|---|---|---|---|---|
| α | 27.2 | β | 0.00 | γ | 0.00 |

EXAMPLE 9

| Surface No. | Radius of curvature | Surface separation | Displacement and tilt | Refractive index | Abbe's No. |
|---|---|---|---|---|---|
| Object plane | ∞ | | | | |
| 1 | ∞ | | (1) | 1.49 | 57.4 |
| 2 | ∞ (PIM) | | (2) | 1.49 | 57.4 |
| 3 | ASS(1) (RE, FL) | | (3) | 1.49 | 57.4 |
| 4 | HOE | | (1) | | |
| Image plane | ∞ | | (4) | | |

ASS(1)

| | |
|---|---|
| R | −816.43 |
| K | $-2.0000 \times 10^{-6}$ |
| A | $1.4845 \times 10^{-11}$ |
| B | $-5.8165 \times 10^{-15}$ |
| C | $2.3649 \times 10^{-19}$ |
| D | $-1.5631 \times 10^{-24}$ |

Displacement and tilt(1)

| X | 0.00 | Y | 0.00 | Z | 650.00 |
|---|---|---|---|---|---|
| α | 27.2 | β | 0.00 | γ | 0.00 |

Displacement and tilt(2)

| X | 0.00 | Y | 0.46 | Z | 650.89 |
|---|---|---|---|---|---|
| α | 27.2 | β | 0.00 | γ | 0.00 |

Displacement and tilt(3)

| X | 0.00 | Y | MY | Z | 604.70 |
|---|---|---|---|---|---|
| α | 27.2 | β | 0.00 | γ | 0.00 |

Displacement and tilt(4)

| X | 0.00 | Y | −205.69 | Z | 249.76 |
|---|---|---|---|---|---|
| α | 27.2 | β | 0.00 | γ | 0.00 |

EXAMPLE 10

| Surface No. | Radius of curvature | Surface separation | Displacement and tilt | Refractive index | Abbe's No. |
|---|---|---|---|---|---|
| Object plane | ∞ | | | | |
| 1 | HOE | | (1) | 1.4924 | 57.6 |
| 2 | ∞ (PIM) | | (1) | 1.4924 | 57.6 |
| 3 | ASS(1) (RE, FL) | | (2) | 1.4924 | 57.6 |
| 4 | ∞ | | (1) | | |
| Image plane | ∞ | | (3) | | |

ASS(1)

| | |
|---|---|
| R | −794.83 |
| K | $-5.3753 \times 10$ |
| A | $1.0973 \times 10^{-6}$ |
| B | $2.4736 \times 10^{-11}$ |
| C | $-2.7488 \times 10^{-16}$ |

Displacement and tilt(1)

| X | 0.00 | Y | 0.00 | Z | 650.00 |
|---|---|---|---|---|---|
| α | 25.00 | β | 0.00 | γ | 0.00 |

Displacement and tilt(2)

| X | 0.00 | Y | MY | Z | 630.94 |
|---|---|---|---|---|---|
| α | 25.00 | β | 0.00 | γ | 0.00 |

Displacement and tilt(3)

| X | 0.00 | Y | −190.18 | Z | 242.16 |
|---|---|---|---|---|---|
| α | 25.00 | β | 0.00 | γ | 0.00 |

EXAMPLE 11

| Surface No. | Radius of curvature | Surface separation | Displacement and tilt | Refractive index | Abbe's No. |
|---|---|---|---|---|---|
| Object plane | ∞ | | | | |
| 1 | ∞ (PIM) | | (1) | 1.4924 | 57.6 |
| 2 | ASS(1) (RE, FL) | | (2) | 1.4924 | 57.6 |
| 3 | ∞ | | (1) | | |
| 4 | HOE | | (1) | 1.4924 | 57.6 |
| Image plane | ∞ | | (3) | | |

ASS(1)

| | |
|---|---|
| R | −792.61 |
| K | 0.0000 |
| A | $3.7000 \times 10^{-9}$ |
| B | $-2.3710 \times 10^{-13}$ |
| C | $5.4398 \times 10^{-18}$ |

Displacement and tilt(1)

| X | 0.00 | Y | 0.00 | Z | 650.00 |
|---|---|---|---|---|---|
| α | 25.00 | β | 0.00 | γ | 0.00 |

Displacement and tilt(2)

| X | 0.00 | Y | MY | Z | 627.89 |
|---|---|---|---|---|---|
| α | 25.00 | β | 0.00 | γ | 0.00 |

Displacement and tilt(3)

| X | 0.00 | Y | −190.18 | Z | 242.16 |
|---|---|---|---|---|---|
| α | 25.00 | β | 0.00 | γ | 0.00 |

EXAMPLE 12

| Surface No. | Radius of curvature | Surface separation | Displacement and tilt | Refractive index | Abbe's No. |
|---|---|---|---|---|---|
| Object plane | ∞ | | | | |
| 1 | HOE | | (1) | 1.4924 | 57.6 |
| 2 | ∞ (PIM) | | (1) | 1.4924 | 57.6 |
| 3 | ASS(1) (RE, FL) | | (2) | 1.4924 | 57.6 |
| 4 | ∞ | | (1) | | |
| Image plane | ∞ | | (3) | | |

| ASS(1) | |
|---|---|
| R | −407.45 |
| K | −5.8103 × 10 |
| A | −7.5130 × 10$^{-7}$ |
| B | 7.5802 × 10$^{-12}$ |
| C | −3.1478 × 10$^{-17}$ |

| Displacement and tilt(1) | | | | | |
|---|---|---|---|---|---|
| X | 0.00 | Y | 0.00 | Z | 650.00 |
| α | 25.00 | β | 0.00 | γ | 0.00 |

| Displacement and tilt(2) | | | | | |
|---|---|---|---|---|---|
| X | 0.00 | Y | MY | Z | 577.79 |
| α | 25.00 | β | 0.00 | γ | 0.00 |

| Displacement and tilt(3) | | | | | |
|---|---|---|---|---|---|
| X | 0.00 | Y | −190.18 | Z | 242.16 |
| α | 25.00 | β | 0.00 | γ | 0.00 |

EXAMPLE 13

| Surface No. | Radius of curvature | Surface separation | Displacement and tilt | Refractive index | Abbe's No. |
|---|---|---|---|---|---|
| Object plane | ∞ | | | | |
| 1 | ∞ (PIM) | | (1) | 1.4924 | 57.6 |
| 2 | ASS(1) (RE, FL) | | (2) | 1.4924 | 57.6 |
| 3 | ∞ | | (1) | | |
| 4 | HOE | | (1) | 1.4924 | 57.6 |
| Image plane | ∞ | | (3) | | |

| ASS(1) | |
|---|---|
| R | −763.19 |
| K | −2.3408 |
| A | −1.8903 × 10$^{-8}$ |
| B | 1.4268 × 10$^{-13}$ |
| C | −4.9692 × 10$^{-19}$ |

| Displacement and tilt(1) | | | | | |
|---|---|---|---|---|---|
| X | 0.00 | Y | 0.00 | Z | 650.00 |
| α | 25.00 | β | 0.00 | γ | 0.00 |

| Displacement and tilt(2) | | | | | |
|---|---|---|---|---|---|
| X | 0.00 | Y | MY | Z | 571.11 |
| α | 25.00 | β | 0.00 | γ | 0.00 |

| Displacement and tilt(3) | | | | | |
|---|---|---|---|---|---|
| X | 0.00 | Y | −190.18 | Z | 242.16 |
| α | 25.00 | β | 0.00 | γ | 0.00 |

Next one specific embodiment of the invention where the projection viewing system is set up as a stereoscopic viewing system is explained with reference to the projection viewing system as shown in FIG. 1.

FIGS. 47(a) and 47(b) are illustrative of one specific embodiment where the projection viewing system of construction of FIG. 1 is constructed in the form of a stereoscopic viewing system. FIG. 47(a) is illustrative in schematic of a transmission type stereoscopic viewing system, and FIG. 47(b) is illustrative in schematic of a reflection type stereoscopic viewing system. In FIG. 47(b), only the arrangement for the right eye is shown for simplicity of illustration; no arrangement for the left eye is shown.

Each of the viewing systems of FIGS. 47(a) and 47(b) are built up of display devices 1L and 1R, projection optical systems 2L and 2R, an eyepiece optical system 4 and a diffusing plate 5 (not shown).

The projection optical systems 2L and 2R project images displayed on the display devices 1L and 1R on a viewer side. The optical system is then constructed such that the projected images are projected onto the same display plane. The exit pupils 16L and 16R of the projection optical systems 2L and 2R are projected on the viewer side. As the viewer moves his eyes EL and ER in line with the positions of the projected exit pupil images, he can view the images displayed on the display devices 1L and 1R. The diffusing plate 5 functions to magnify the pupil for observation. The eyepiece optical system 4 and the diffusing plate 5 are located at the position of the display plane.

At the position of the display plane, the images on the display devices 1L and 1R, which are projected through the projection optical systems 2L and 2R, are formed. For the transmission type stereoscopic viewing system (FIG. 47(a)), a Fresnel lens is provided as the eyepiece optical system 4 at this image-formation position, and for the reflection type stereoscopic viewing system (FIG. 47(b)), a Fresnel mirror is provided.

The Fresnel mirror is designed such that the images of two exit pupils 16L and 16R are formed on the viewer side, as is the case with the Fresnel lens. Since each Fresnel surface is located at (or near) the position of the display plane, there is no deterioration in the quality of the projected images. Unlike the concave mirror, the Fresnel surface is located in a flat plate form.

Figure 48:
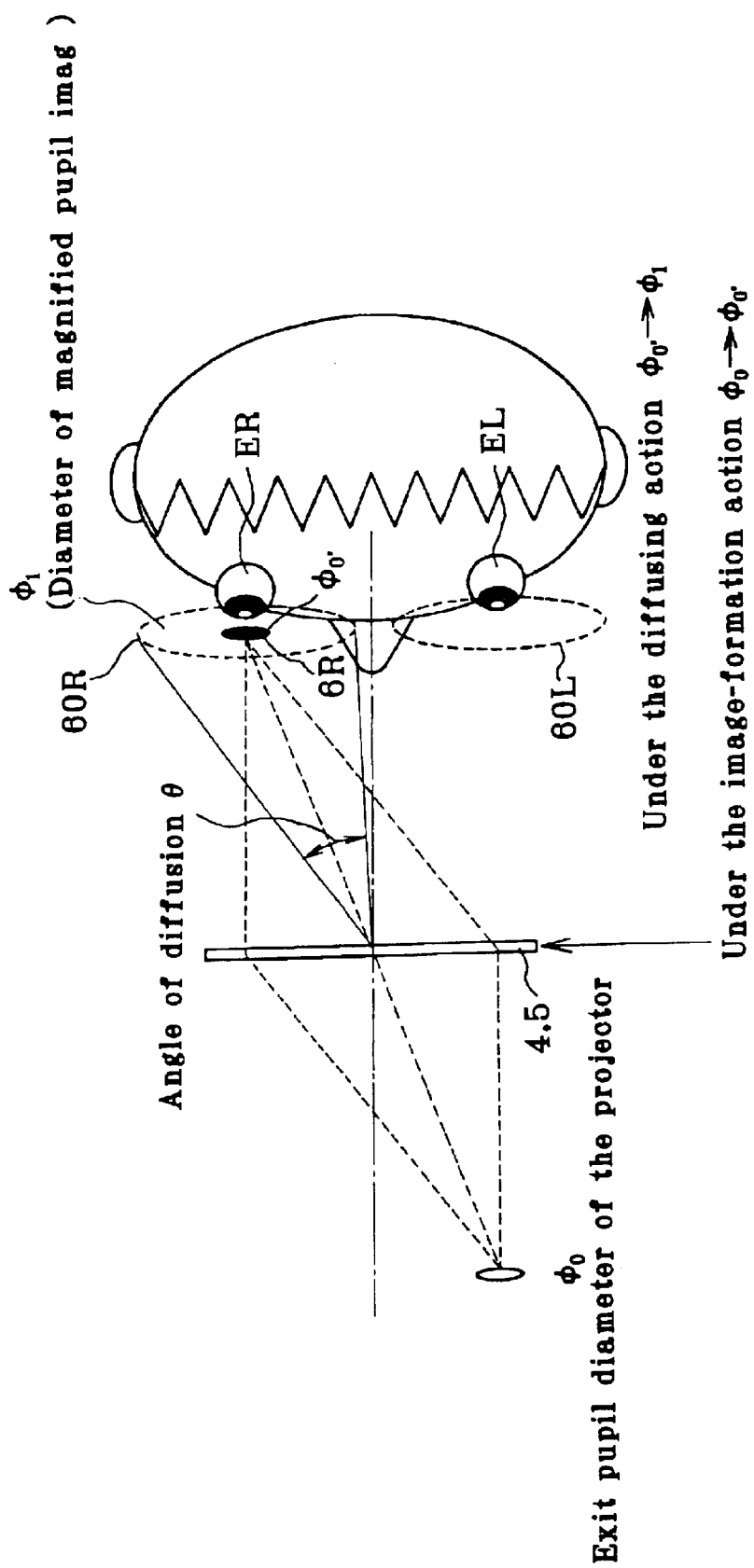
FIG. 48 is illustrative of the principle of why the exit pupil image (the pupil for observation) is magnified in the transmission type stereoscopic viewing system of FIG. 47($a$).

FIG. 48 is illustrative of the principle of why the exit pupil image (the pupil for observation) is magnified in the transmission type stereoscopic viewing system.

The eyepiece optical system 4 is located at or near the planar display plane together with the diffusing plate 5. In FIG. 48, the eyepiece optical system 4 acts to form the images of the exit pupils 16L and 16R of the left and right projection optical systems 2L and 2R at given positions on the viewer side. In this case, the diameters $\phi_0$ of the exit pupils 16L and 16R are each projected with a diameter $\phi_0'$.

At the given positions, the eyeballs (pupils) EL and ER of the viewer are located. Here, the diffusing plate 5 is set such that the pupil images of the exit pupils 6L and 6R of the left and right projection optical systems 2L and 2R, which are to be inherently formed with the diameter $\phi_0'$, are each magnified by its diffusing action to a diameter $\phi_1$. It is noted that the left and right exit pupil images 60L and 60R magnified through the diffusing plate 5 are formed such that they are not superposed one upon another at the viewing position having a distance L for the purpose of preventing the occurrence of cross talks. In the transmission type stereoscopic viewing system, this diffusing plate 5 exerts its diffusing action only once because the light transmits only once through the diffusing plate 5 located at the position of the display plane. In the reflection type stereoscopic viewing system (not shown in FIG. 48), by contrast, the diffusing plate 5 exerts its diffusing action twice because the light transmits twice through the diffusing optical system located at the position of the display plane.

Figure 49A:
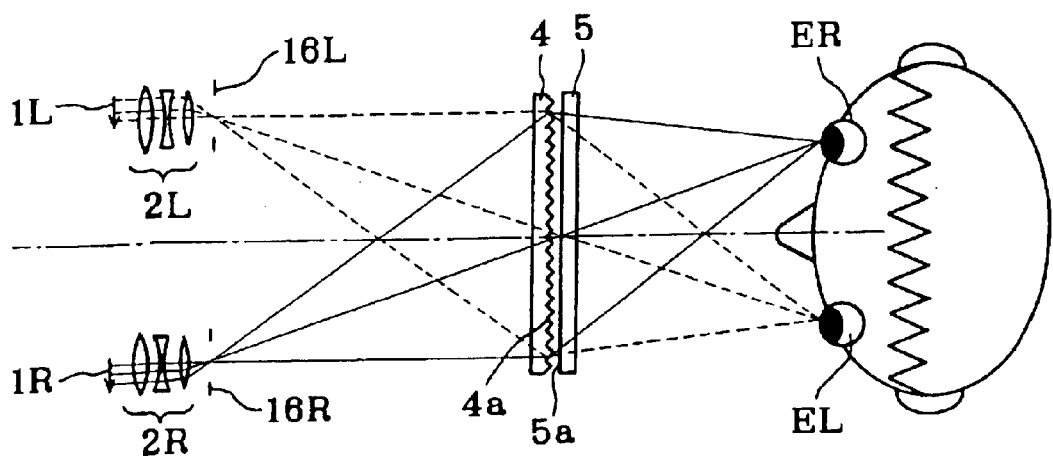
FIGS. 49($a$) and 49($b$) are illustrative of one embodiment of the stereoscopic viewing system according to the invention.
Figure 49B:
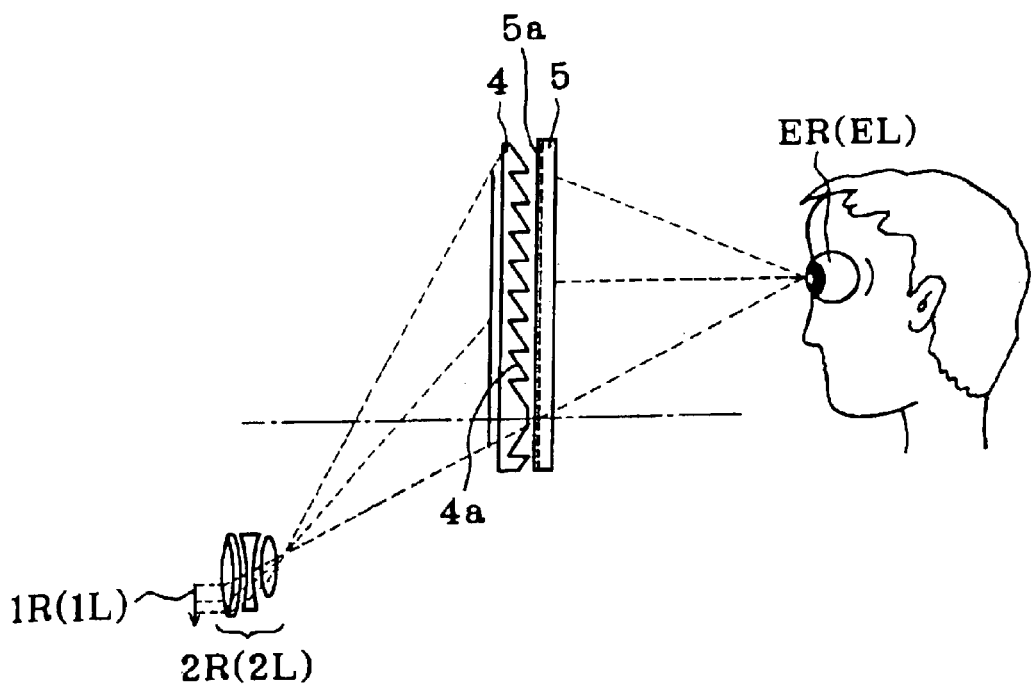

FIGS. 49(a) and 49(b) are illustrative of one embodiment of the stereoscopic viewing system according to the invention. More specifically, FIG. 49(a) is a schematic of the stereoscopic viewing system as viewed from above, and FIG. 49(b) is a side view of the stereoscopic viewing system. This stereoscopic viewing system is of the transmission type. At the position of a display plane, there is located an eyepiece optical system 4 for projecting the exit pupils 16L and 16R of projection optical systems 2L and 2R on a viewer side. As the viewer moves his eyeballs (pupils) EL and ER in line with the projected positions, he can view images.

For this eyepiece optical system 4, a Fresnel lens having a Fresnel surface 4a directed toward the viewer side is used. This Fresnel lens 4 combines with a diffusing plate 5 located in the vicinity thereof for the purpose of magnifying the pupils to form a transmission type display panel. In the instant embodiment, the Fresnel lens surface 4a is located at an image-formation position for the images projected through the projection optical systems 2L and 2R. Accordingly, there is no image quality deterioration due to the Fresnel lens surface 4a. The diffusing surface 5a of the diffusing plate 5 is located on the Fresnel lens surface 4a side of the Fresnel lens 4. The diffusing surface 5a is so close to the Fresnel lens surface 4a that blurring can be reduced with limited image quality deterioration.

In the instant embodiment, the transmission type display panel is constructed of a decentered optical system. To be more specific, the Fresnel lens surface 4a takes the form of a decentered Fresnel lens surface and, as shown in FIG. 49(b), the optical axis of the Fresnel lens surface 4a is located below the center. The Fresnel lens surface 4a has positive refracting power.

When the transmission type display panel is constructed of a decentered optical system as in the instant embodiment, the display panel itself remains slimmed down, so that it can be laid out in an un-obstructive fashion. To prevent image quality deterioration, it is preferable to locate the diffusing surface 5a and the Fresnel surface 4a as close to the position of the display plane as possible.

Figure 50A:
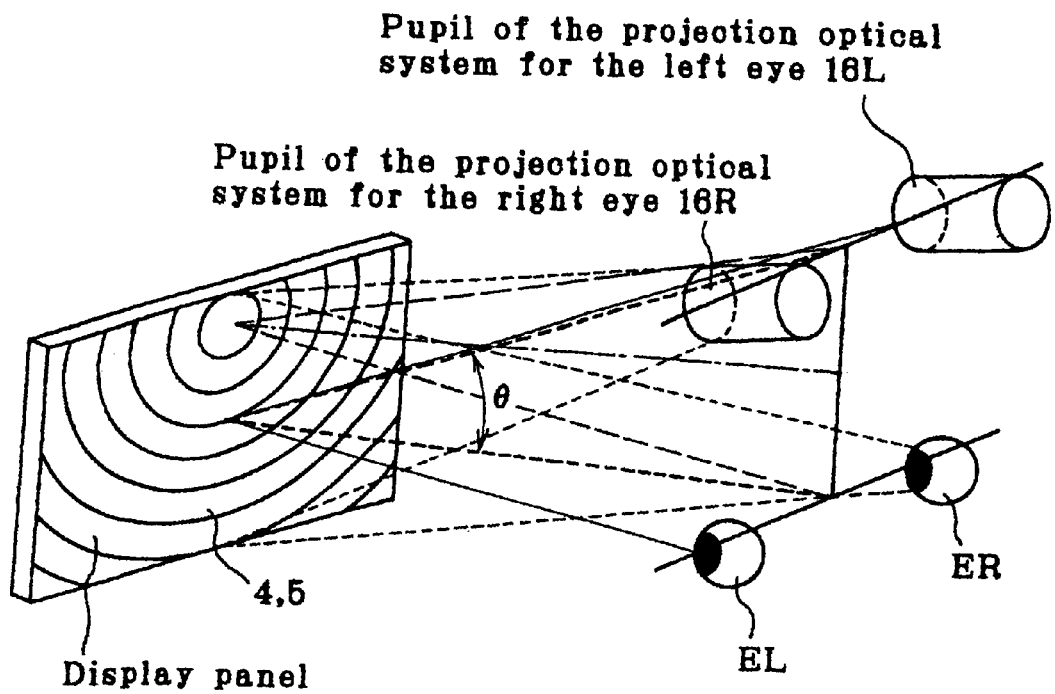
FIGS. 50($a$) and 50($b$) are illustrative of another embodiment of the stereoscopic viewing system according to the invention.
Figure 50B:
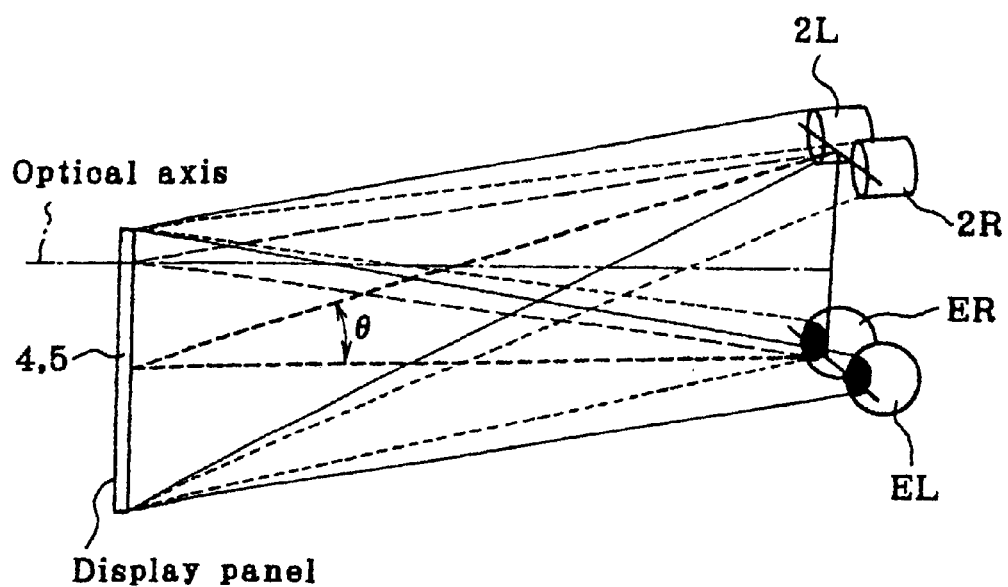

FIGS. 50(a) and 50(b) are a perspective view and a side view of another embodiment of the stereoscopic viewing system according to the invention.

The stereoscopic viewing system of this embodiment is of the reflection type. A display panel comprises an eyepiece optical system 4 and a diffusing plate 5 for magnifying pupils. The eyepiece optical system 4 specifically comprises a Fresnel mirror 4. The eyepiece optical system 4 projects the exit pupils 16L and 16R of projection optical systems 2L and 2R on a viewer side. As the viewer moves his eyes EL and ER in line with the projection positions, he can view images.

For the reflection type stereoscopic viewing system, the respective optical members must be positioned in such a way that there is no interference between the projection optical systems 2L, 2R and the face of the viewer. For the viewer, images are more easily viewable from the front of the display panel. In the instant embodiment, therefore, an angle θ is made between the optical axis of incidence of projection light on the center of the display panel and the exit optical axis of light leaving the center of the display plane and the optical axis of the Fresnel mirror 4 is decentered in an upward or downward direction (upward in FIGS. 50(a) and 50(b)) with respect to the center of the display panel.

Figure 51:
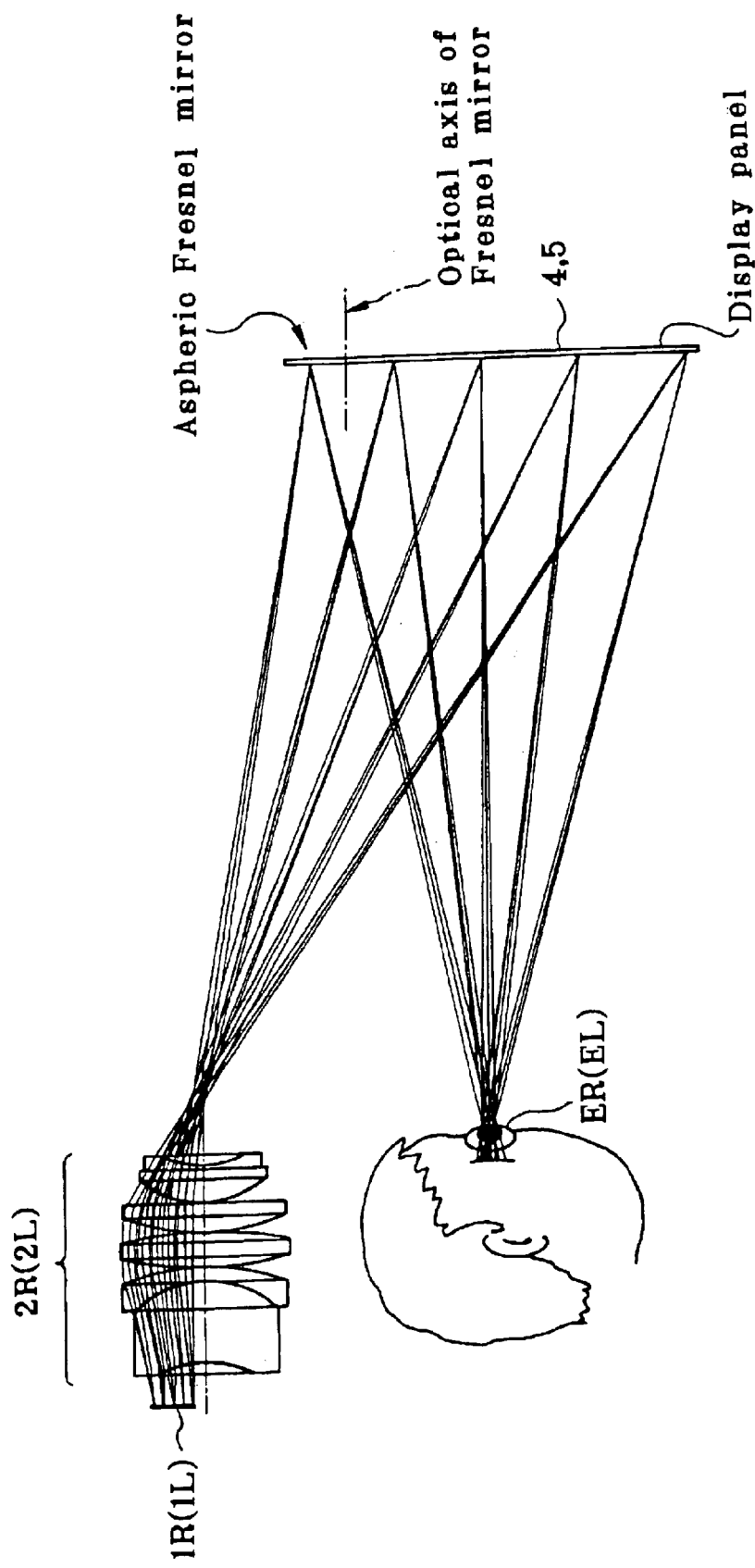
FIG. 51 is a side schematic of one specific example of the embodiment of FIGS. 50($a$) and 50($b$).

FIG. 51 is a side view of a more specific example of the embodiment of FIGS. 50(a) and 50(b). In the example of FIG. 51, a spherical lens system is used for a projection optical system 2R(2L) and a display device 1R(1L) is decentered or displaced from the optical axis of the lens, so that there is no interference between the projection optical system 2R(2L) and the face of a viewer. A display panel is disposed vertically to the eye of the viewer and the projection optical system 2R(2L), and an aspheric Fresnel mirror is used for the surface of the display panel.

While the display panel should preferably be such that the viewer can view its front as mentioned above, it is acceptable to incline the display plane at an angle of ±30°. At an angle of inclination of about ±15°, images of good quality could be viewed.

Figures 52A, 52B, 52C:
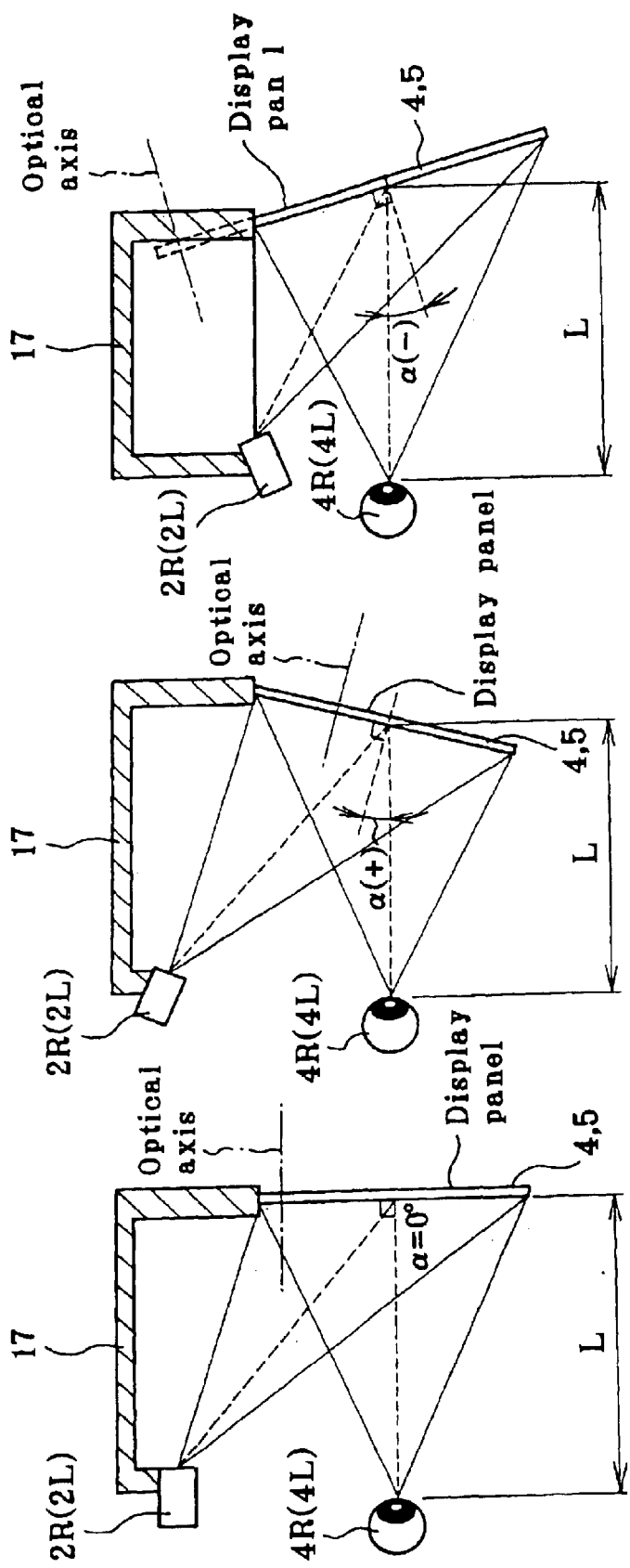
FIGS. 52($a$), 52($b$) and 52($c$) are side schematics of modifications to the example of FIGS. 51($a$) and 51($b$).

FIGS. 52(a), 52(b) and 52(c) are side schematics of modifications to the example of FIG. 51. In FIGS. 52(a)–52(c), the line of sight of a viewer is shown as being fixed in the horizontal direction. In these modifications, the relative position of the display panel to the eyeball ER(EL) of the viewer is determined by two quantitative factors: (1) the angle of inclination of the display panel and (2) the quantity of decentration of the optical axis of a decentered Fresnel lens surface provided on the surface of the display panel. Images can be observed in the optimum state by control of combinations of two such quantities. It is here noted that the projection optical system 2R(2L) is positioned vertically to the surface of the display panel. In FIGS. 52(a)–52(c), reference numeral 17 stands for a support arm for supporting two projection optical systems 2R and 2L, two display devices 1R and 1L and the display panel. The angle of inclination α of the surface of the display panel is given by an angle of a line connecting the center of the display plane to the pupil of the viewer, which subtends a perpendicular from the center of the display panel, and should preferably be no greater than ±30° in view of ease with images are viewed.

In the stereoscopic viewing system of FIG. 52(a), the angle of inclination α of the display panel surface is set at 0°, and in those of FIGS. 52(b) and 52(c), the angle of inclination a of the display panel surface is set at no greater than 30°. The arrangement (a) or (b) is superior to (c) because more natural images can easily be seen and the quantity of decentration of image-formation action is more reduced.

Next, specific embodiments of the display panel used with the stereoscopic viewing system of the invention are now explained.

FIGS. 53(a) and 53(b) are a perspective view and a side schematic of one embodiment of the reflection type display panel that is applicable to the reflection type stereoscopic viewing system of the invention. In this display panel, a Fresnel surface 4a is integrated with a diffusing plate 5a having a random array of concave facets. Specifically, a plastic resin such as polycarbonate or acrylic resin is pressed from both its sides for integral molding, using a Fresnel surface-dedicated mold and a scattering surface-dedicated mold having a random array of concave facets. Then, aluminum is coated on the Fresnel surface 4a to form a reflecting film that is further coated with a black paint to form a protective film.

The Fresnel surface 4a of the display panel acts to form the images of the exit pupils 16L and 16R of two projection optical systems 2L and 2R, so that the viewer can turn his eyeballs (pupils) to the image-formation positions to observe images. The diffusing surface 5a acts to magnify the pupils for magnification, so that even when the viewer moves his eyeballs (pupils) more or less out of the image-formation positions, he can view images in much the same manner as his eyeballs are in line with the image-formation positions.

The display panel shown in FIGS. 53(a) and 53(b) is constructed in the form of a decentered Fresnel back-surface mirror. Consider now the radius of curvature R of the Fresnel surface 4a constructed in the form of a front-surface mirror and a back-surface mirror.

The radius of curvature R of the Fresnel surface in the form of the back-surface mirror is given by $$R=2n\cdot f$$

The radius of curvature R of the Fresnel surface in the form of the front-surface mirror is given by $$R=2f$$

Here n is a refractive index, and f is a focal length.

Thus, the back-surface mirror allows the radius of curvature R of the Fresnel surface to become larger, and so is more favorable because aberrations produced upon the formation of pupil images are more reduced.

Further in the instant display panel, the Fresnel surface 4a is defined by an aspheric Fresnel surface, the radius of curvature of which becomes larger off and off its center. This construction is favorable because aberrations produced by the pupils for observation upon image-formation are more reduced.

Figure 54A:
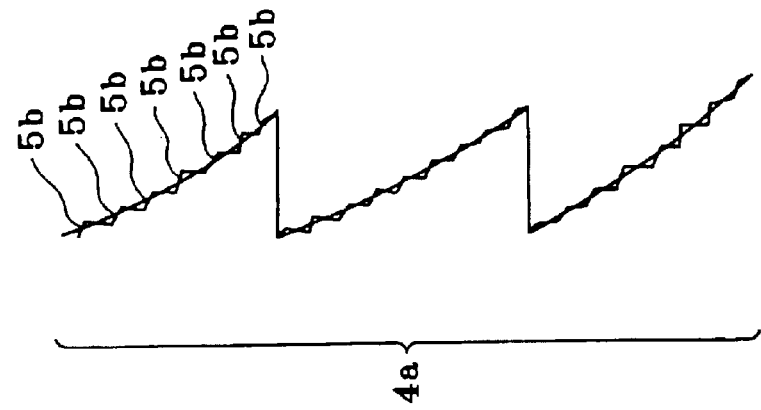
FIGS. 54($a$) and 54($b$) are illustrative of another embodiment of the reflection type display panel that is applicable to the reflection type stereoscopic viewing system of the invention.
Figure 54B:
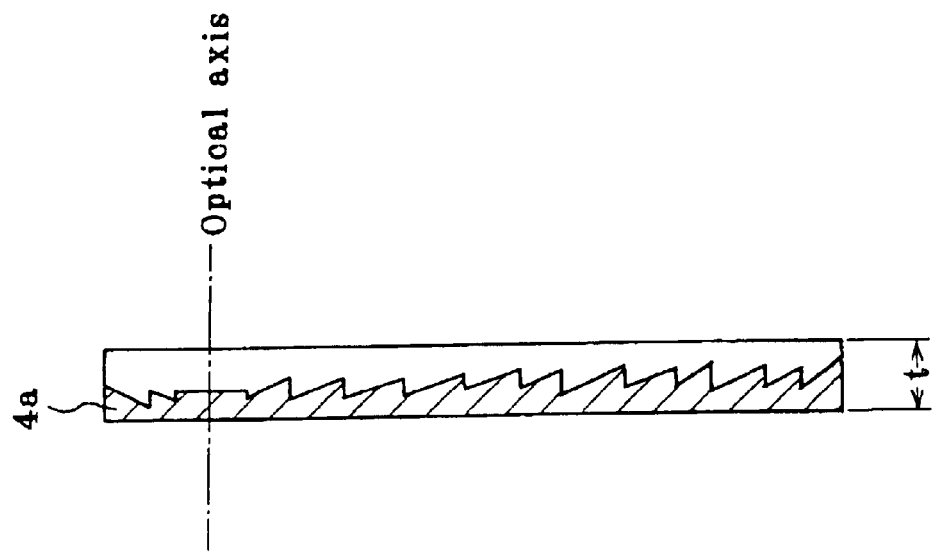

FIGS. 54(a) and 54(b) are a side schematic of another embodiment of the reflection type display panel, and an enlarged view of diffusing means, respectively. Instead of the diffusing surface 5a having randomly arranged concave facets 5b as shown in FIG. 53(b), the instant display panel incorporates as the diffusing means a Fresnel surface 4a provided with minuscule concave facets 5b by integral molding, as shown in FIG. 54(b). It is noted that the Fresnel surface 4a is coated with a reflecting film to form a back-surface Fresnel reflecting mirror. It is also noted that the instant display panel has a planar surface so that an antireflection film can easily be coated thereon.

In the instant reflection type display panel, the Fresnel surface 4a having an image-formation action and the minuscule concave facets 5b having a diffusing action are formed on the same back surface, as mentioned above. In such a reflection type display panel as shown in FIGS. 53(a) and 53(b), the projection light passes usually twice through the diffusing surface whereas, in the instant embodiment, the projection light passes only once through diffusing surface; in other words, the projection light is subjected to only one diffusing action. Accordingly, blurring is so unlikely to occur that image quality deterioration, if any, can be reduced.

Figure 55:
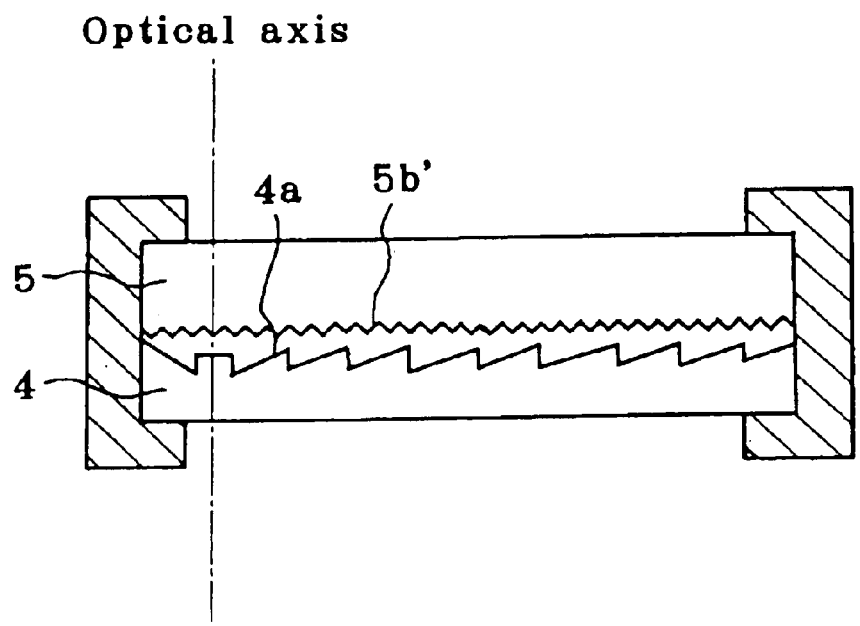
FIG. 55 is a side schematic of yet another embodiment of the reflection type display panel that is applicable to the reflection type stereoscopic viewing system of the invention.

FIG. 55 is a side schematic of yet another embodiment of the reflection type display panel, wherein an eyepiece optical system 4 is built up of a Fresnel front-surface mirror and diffusing means is formed of a diffusing plate 5. In this embodiment, a Fresnel surface 4a is proximate to a diffuse pit-and-projection pattern surface 5b' formed on the surface of the diffusing plate 5 in a face-to-face fashion.

In the instant display panel, the Fresnel surface 4a formed on its surface is brought in as close contact with the diffuse pit-and-projection surface 5b' as possible, so that blurring stemming from two passages of the projection light through the diffusing surface can be minimized. According to the instant embodiment, it is acceptable to laminate a diffusing film onto the front-surface Fresnel mirror rather than to bring the front-surface Fresnel mirror 4 in close contact with the diffusing plate 5.

Figure 56:
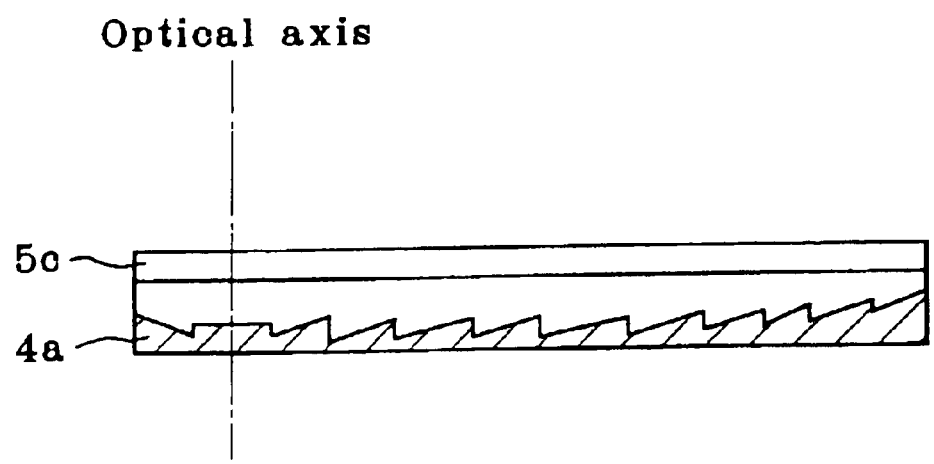
FIG. 56 is a side schematic of a further embodiment of the reflection type display panel that is applicable to the reflection type stereoscopic viewing system of the invention.

FIG. 56 is a side schematic of a further embodiment of the reflection type display panel, wherein instead of forming a minuscule pit-and-projection pattern surface on the surface of the decentered Fresnel back-surface mirror shown in FIGS. 53(a) and 53(b), a diffusing film 5c is laminated onto it. It is noted that the diffusing film 5c used could be either of the internal scattering type or of the type that light is scattered by pits and projections formed on the surface.

Next, various embodiments of the projection viewing system according to the invention are explained. In such embodiments, a reflection type concave mirror, a reflection type Fresnel reflecting mirror and so on are used for an eyepiece optical system, and a diffusing plate comprising a pit-and-projection pattern surface or a roughened surface or a transmission hologram is used as a diffusing plate located on the front surface of the eyepiece optical system. A display panel is designed such that images are projected and displayed as shown in FIG. 1 or FIG. 2.

These embodiments are now explained on the assumption that a combined reflection type eyepiece optical system and diffusing plate is referred to as a display panel 100; and projectors 101, 101L and 102R are each built up of a display device 1 and a projection optical system 2 for magnifying and projecting an image displayed on the display device 1, as shown in FIG. 1 or each projector is made up of scanning means 8 for deflecting a light beam incident from a light source 7 and a projection optical system 9 for projecting and condensing the deflected light beam, as shown in FIG. 2.

Figure 57:
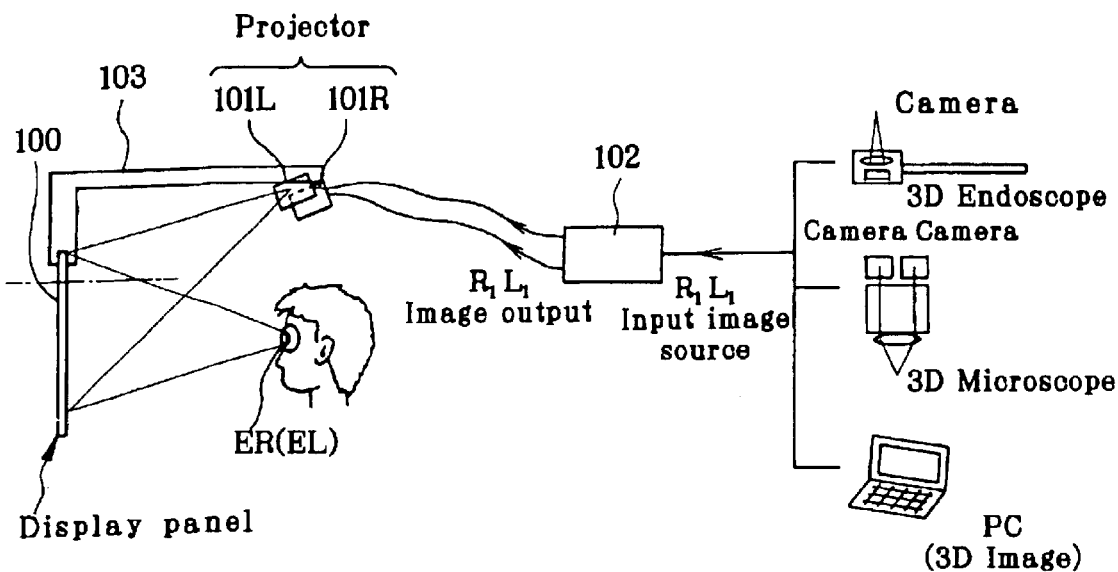
FIG. 57 is illustrative of one specific product incorporating the stereoscopic viewing system of the invention.

FIG. 57 is illustrative in schematic of one embodiment of the stereoscopic viewing system to which the invention is applicable. The system has such construction as described in each of the above embodiments and examples. In the instant embodiment, left and right projectors 101L and 102R are connected to a projector controller 102 that singles out a desired image to send the selected image to the left and right projectors 101L and 101R for displaying purposes. The image is taken by a camera incorporated in a stereoscopic (3D) image input device. The stereoscopic (3D) image input device could be a stereoscopic (3D) endoscope, a stereoscopic (3D) microscope or the like, which has left and right cameras.

Other selectable input images, for instance, include a personal computer-aided stereoscopic (3D) image having parallax. The projector controller 102 enables even such an image to be managed as an input image to a display panel 100. That is, the projector controller 102 is constructed such that such an image can be displayed on the projectors 101L and 101R.

Next, products incorporating the stereoscopic viewing system according to the invention are explained.

Figure 58:
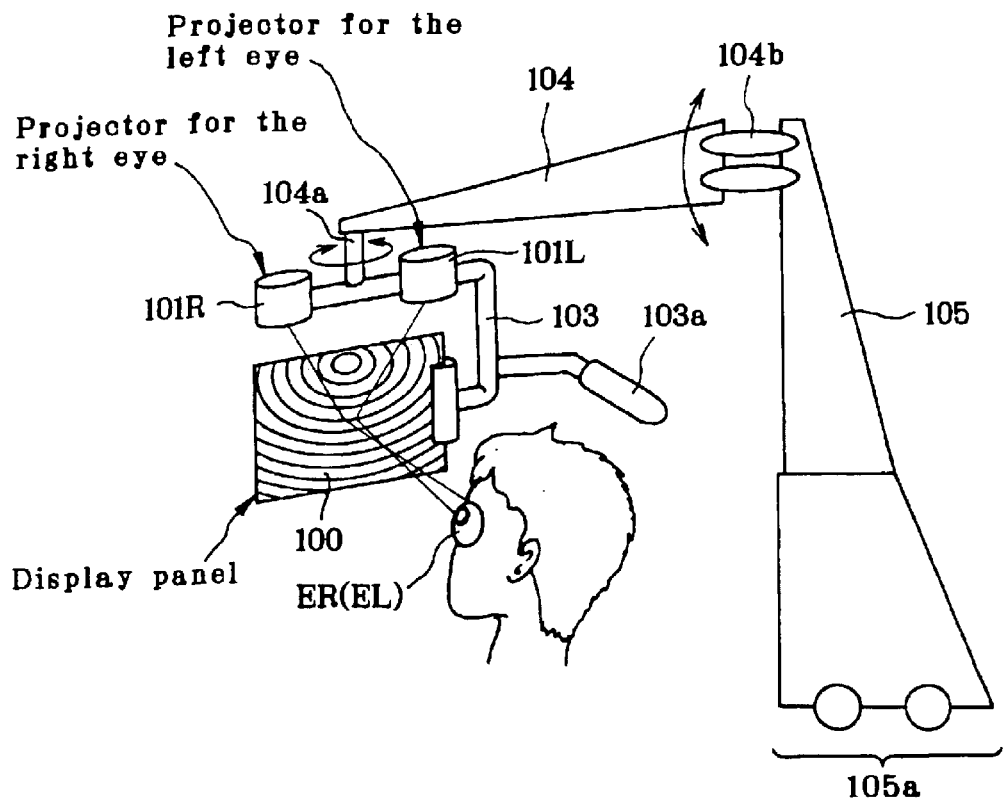
FIG. 58 is illustrative of another specific product incorporating the stereoscopic viewing system of the invention.

FIG. 58 is illustrative of one specific product incorporating the stereoscopic viewing system according to the invention, which is built up of a reflection type stereoscopic projection viewing system, a support arm 104 for supporting a holder 103 and a holder body 105 having a caster, which supports the support arm 104. The reflection type stereoscopic projection viewing system comprises a display panel 100 and left and right projectors 101L and 101R, all integrally mounted on the holder 103.

In the reflection type stereoscopic viewing system, images having parallaxes are projected from the left and right projectors 101L and 101R. Then, the projected images are reflected at the display panel 100 to form the images on the left and right eyes EL and ER of a viewer while magnifying the pupils for observation (the pupils of the optical systems).

The holder 103 is rotatable via a joint 104a of the support arm 104 in a direction indicated by an arrow. The support arm 104 is coupled to the support body 105 via a joint 104b in such a way as to be rotatable in the direction indicated by an arrow. Thus, the viewer can change his attitude by turning the holder 103 and support arm 104 in the desired direction. The holder 103 is also provided with a manipulator 103a that helps turn them in the desired direction.

The support body 105 is equipped with a caster 105a for moving the support body 105, so that the viewer can change his viewing position.

Figure 59:
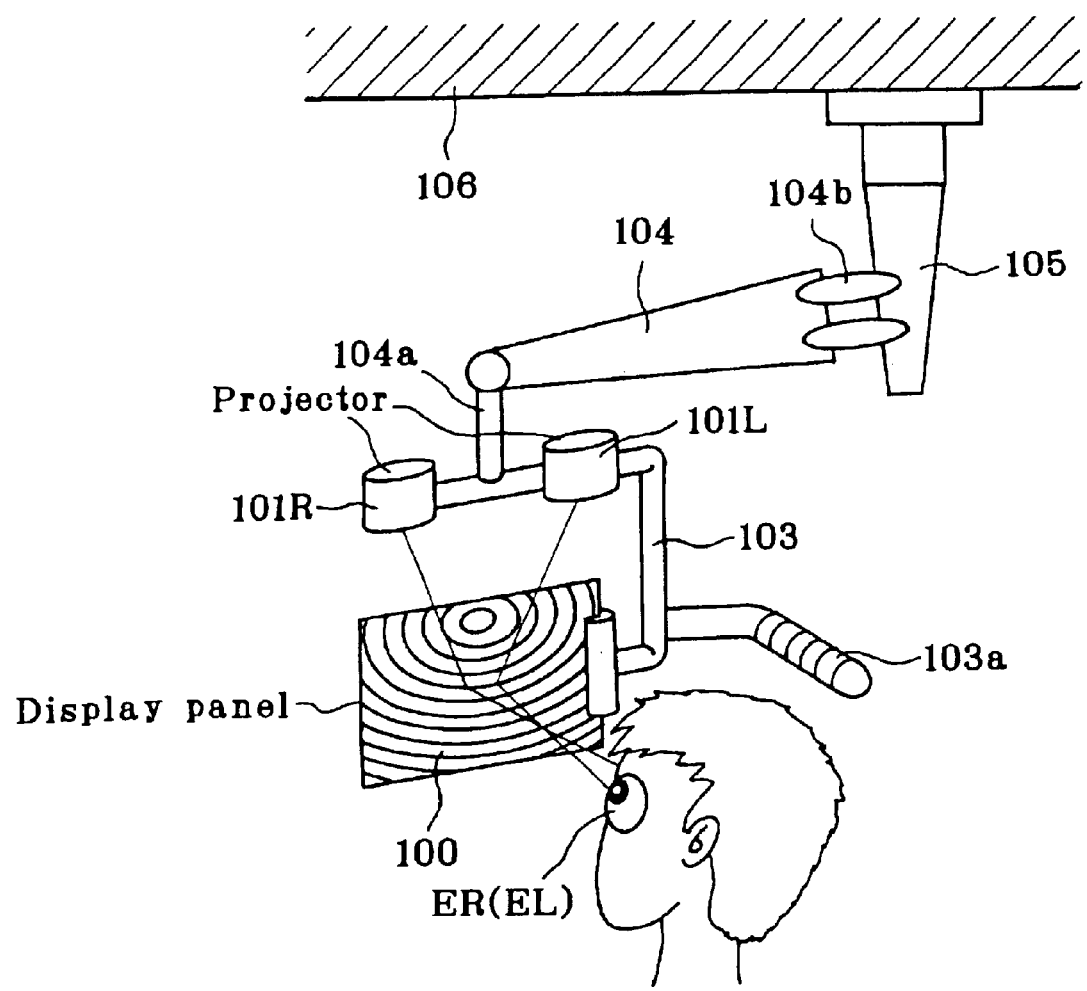
FIG. 59 is illustrative of yet another specific product incorporating the stereoscopic viewing system of the invention.

FIG. 59 is illustrative of another specific product incorporating the stereoscopic viewing system of the invention. In this product, too, a reflection type stereoscopic projection viewing system is held by a support arm 104, as shown in FIG. 58. However, a support body 105 for supporting the support art 104 is mounted to a ceiling 106. The instant product can save space for placing the stereoscopic projection viewing system.

Figure 60:
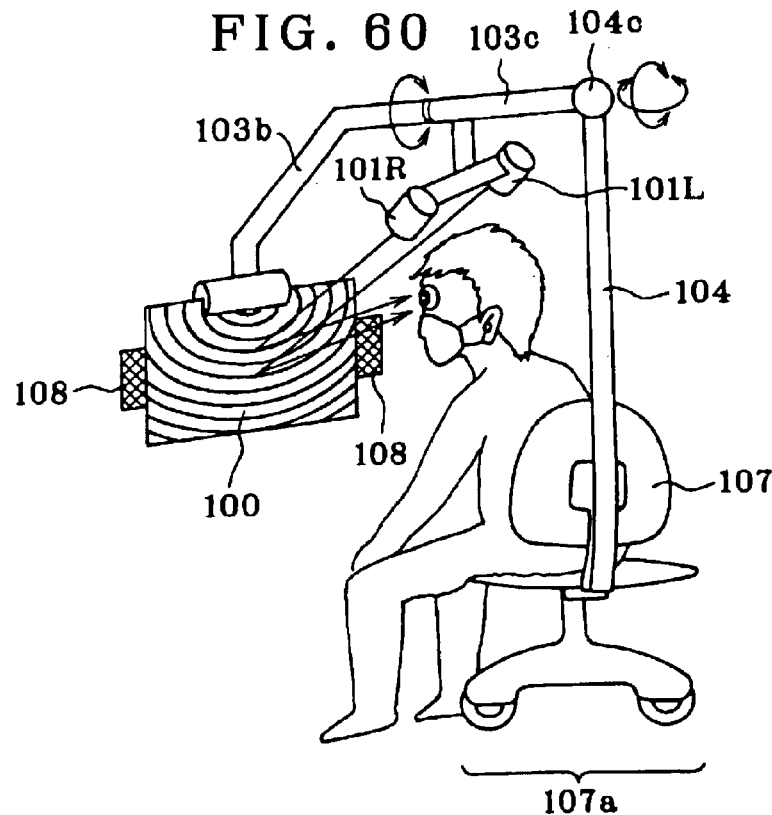
FIG. 60 is illustrative of a further specific product incorporating the stereoscopic viewing system of the invention.

FIG. 60 is illustrative of yet another product incorporating the stereoscopic viewing system of the invention, wherein a support arm 104 is attached to a surgical chair 107.

A display panel 100 is attached to one holder 103b, and projectors 101L and 101R are attached to another holder 103c that is rotatable through 360°, so that the display panel 100 and the projectors 101L and 101R can be turned to a desired direction. The display panel 100 is provided with grips 108 on both sides, so that the direction of the display panel 100 can easily be adjusted without direct contact with the display panel 100. The surgical chair 107 is further provided with a caster 107a for carrying the surgical chair 107 to change the viewing position.

Figure 61:
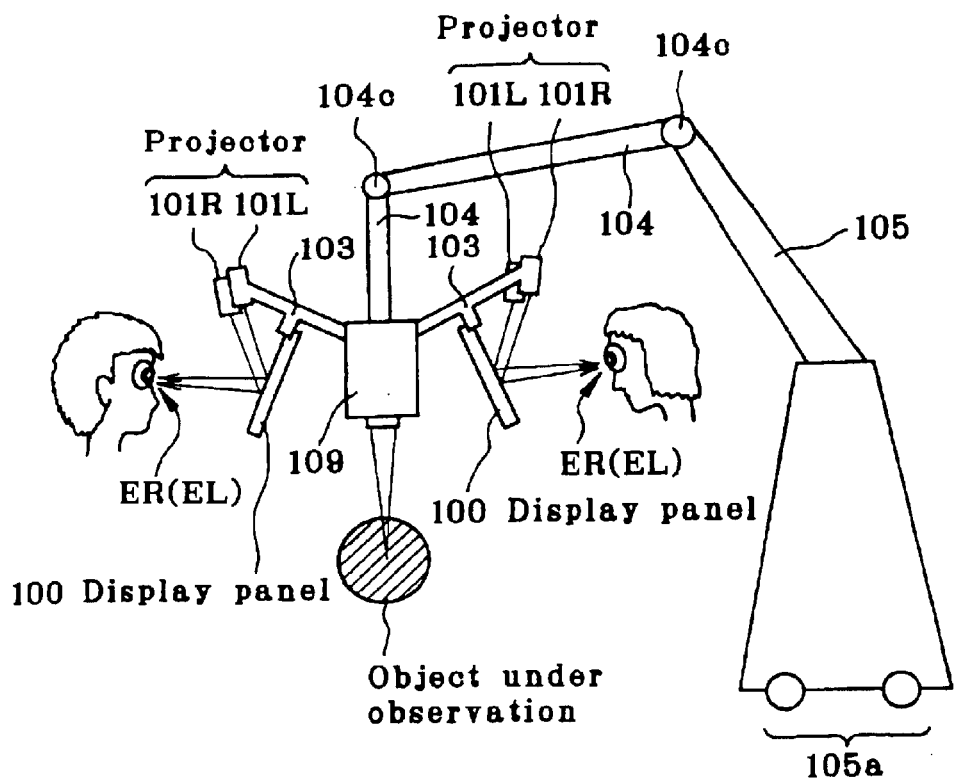
FIG. 61 is illustrative of a further specific product incorporating the stereoscopic viewing system of the invention.

FIG. 61 is illustrative of a further specific product incorporating the stereoscopic viewing system of the invention, wherein a support arm 104 is connected with two holders 103 and an image input 109 of a surgical microscope. Each holder 103 holds projectors 101L and 101R and a display panel 100. It is noted that the support arm 104 is connected via a joint 104c to a support body 105 having a caster 105a, so that it is rotatable by means of the joint 104c.

The image input of the surgical microscope has two built-in cameras. Then, input images are sent to the pairs of projectors 101L and 101R of the stereoscopic projection viewing system, so that a plurality of viewers can simultaneously view stereoscopic images at a surgical microscope.

It is noted that the stereoscopic viewing system products shown in FIGS. 58–61 could have applications for display devices of surgical microscopes, display devices of endoscopes, display devices of medical stereoscopic information images, display devices of entertainments such as computer game machines, display devices of business-dedicated stereoscopic (3D) images such as various stereoscopic (3D) CAD images, etc.

Figure 62:
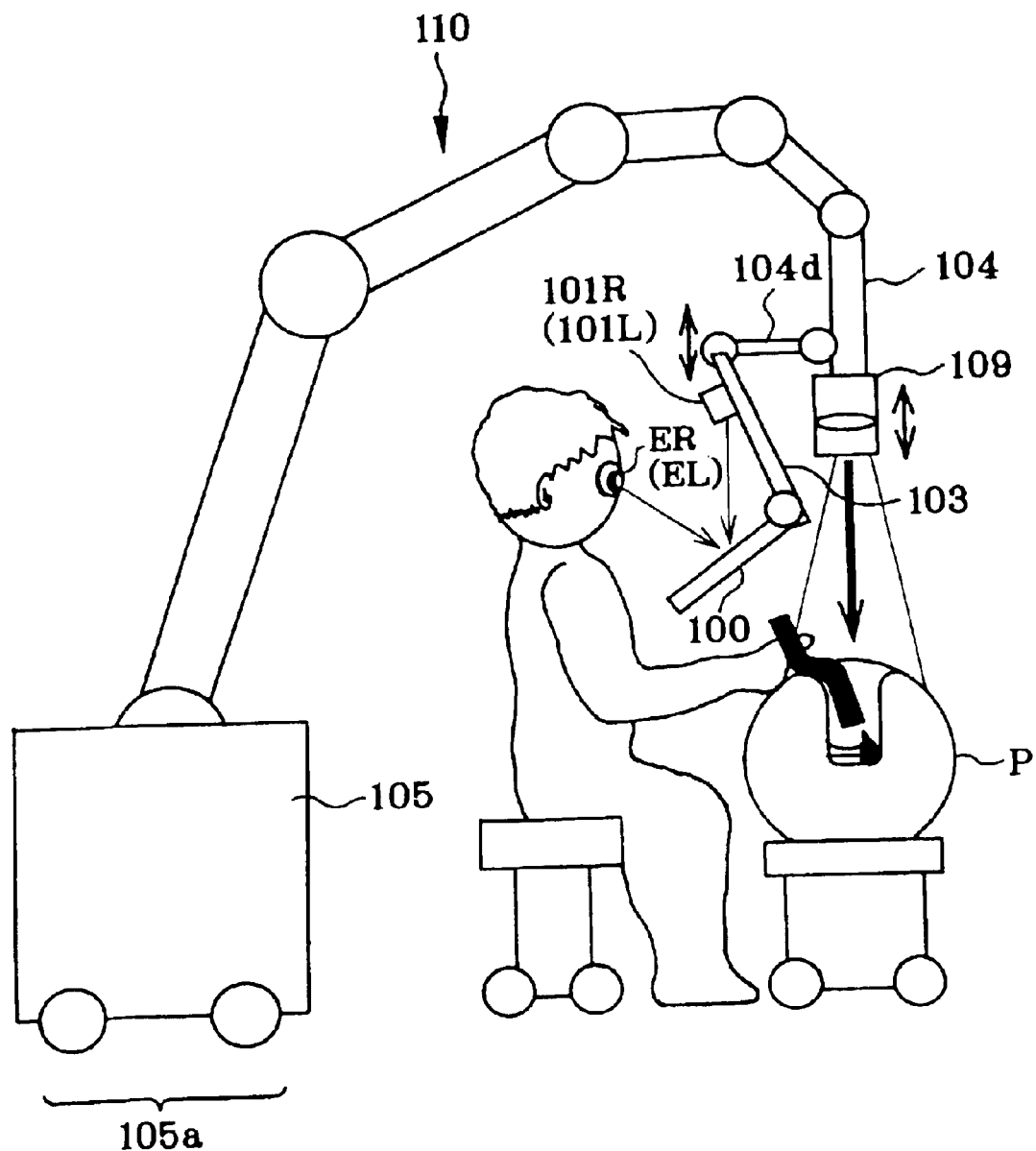
FIG. 62 is illustrative of one specific surgical stereoscopic viewing system incorporating the projection viewing system of the invention.

FIG. 62 is illustrative of one specific surgical stereoscopic viewing system incorporating the projection viewing system of the invention, wherein a universal arm 110 is attached to a support body 105 having a caster 105a, and a support arm 104 is attached to the universal arm 110. Three-dimensionally movable, the support arm 104 is rotatable through 360°. A holder 103 is mounted on the support arm 104 via a joint 104d. This holder 103, too, is movable and rotatable. The holder 103 is provided with projectors 101L and 101R and a display panel 100.

On the other hand, the support arm 104 is provided at its end with an image input 109 of a surgical microscope. The image input 109 has two built-in cameras for taking pictures of an affected site of a patient P. The taken pictures are sent as input images to the stereoscopic projection viewing system, more specifically to the projectors 101L and 101R.

With the stereoscopic viewing system product of FIG. 62, it is thus possible to perform operation while viewing stereoscopic images of the affected area of the patient P.

Figure 63:
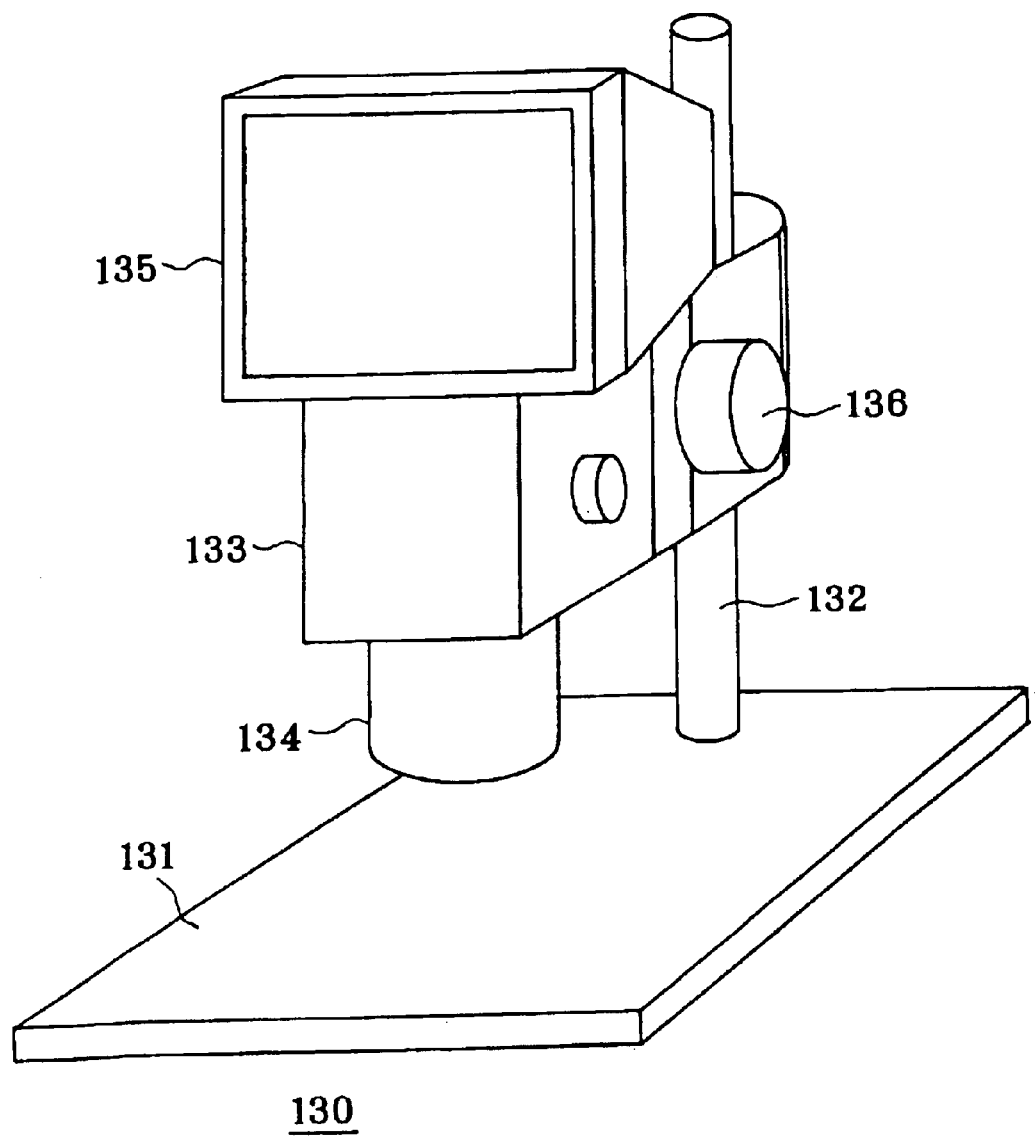
FIG. 63 is a perspective illustration of the appearance of the projection viewing system of the invention that is constructed in the form of a binocular stereomicroscope.
Figure 64:
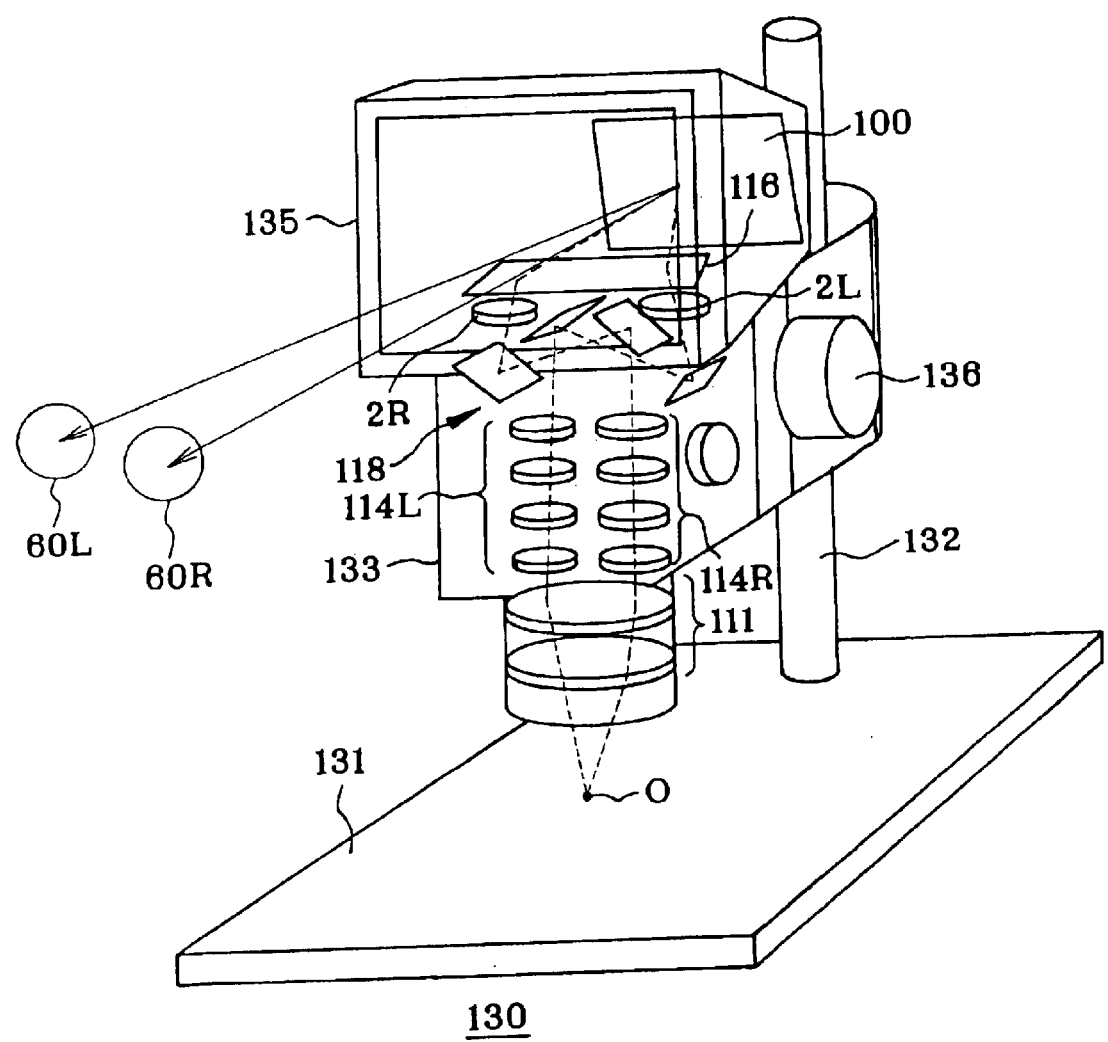
FIG. 64 is a perspective illustration of the optical system added to FIG. 63.

The projection viewing system of the invention may be set up in the form of a binocular stereomicroscope, as shown typically in FIGS. 63 and 64. FIG. 63 shows the appearance of the stereomicroscope, and FIG. 64 is a perspective view of an optical system. In this embodiment, the binocular stereomicroscope 130 is constructed as follows. A stage 131 is vertically provided with a stand 132, to which a lens barrel box 133 is attached. The lens barrel box 133 is provided with a focusing screw 136 that is manipulated to control the height from the stage 132. On the other hand, the lens barrel box 133 is provided at its lower end with an objective optical system barrel 134, and at its upper end with a hood 135.

As can be seen from FIG. 64, the optical system is received in the objective optical system barrel 134, lens barrel box 133 and hood 135. The optical system comprises an objective optical system 111, left and right image-formation optical systems 114L and 114R, an optical element 118, left and right projection optical systems 2L and 2R and a mirror 116 for bending an optical path. Here the optical element 118 comprises a total of four plane mirrors having an optical path interchanging action and an optical path-to-path space enlarging action.

In this optical system, left-eye and right-eye magnified images of an object O are projected through the left and right projection optical systems 2L and 2R onto a display panel 100. On the display panel 100 left and right exit pupils 60L and 60R are formed as left-eye and right-eye eye points. This enables the object O to be viewed as a stereoscopic image through both eyes of the viewer on a magnified scale.

In the invention, the reflection type display panel 100 comprises a combination of the reflection type eyepiece optical system with the diffusing plate. This display panel 100 could be used as a projection viewing system for displaying not only stereoscopic images but single images as well.

Figure 65:
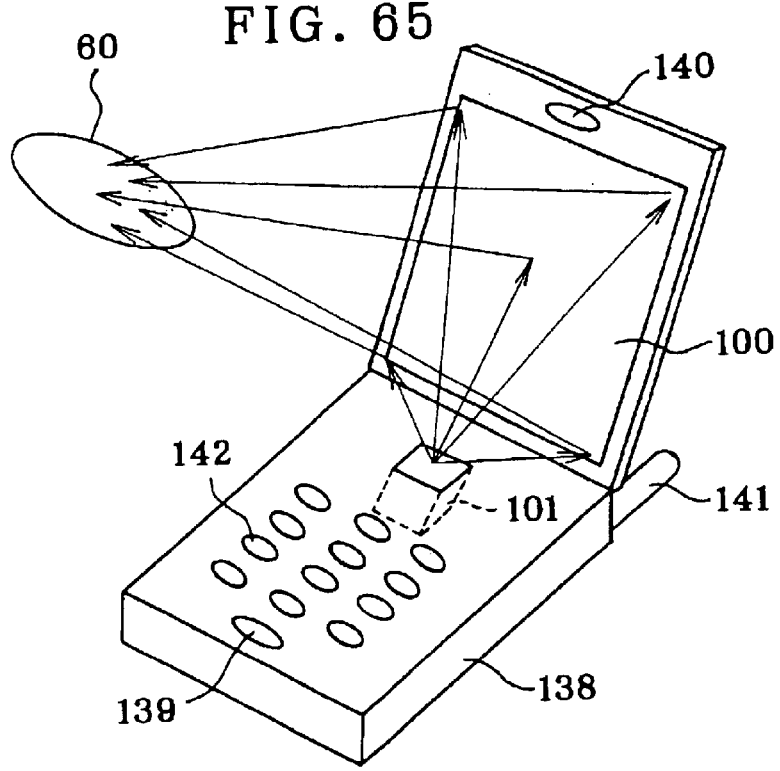
FIG. 65 is a perspective view of one specific cellular phone to which the projection viewing system of the invention is applied.
Figure 66:
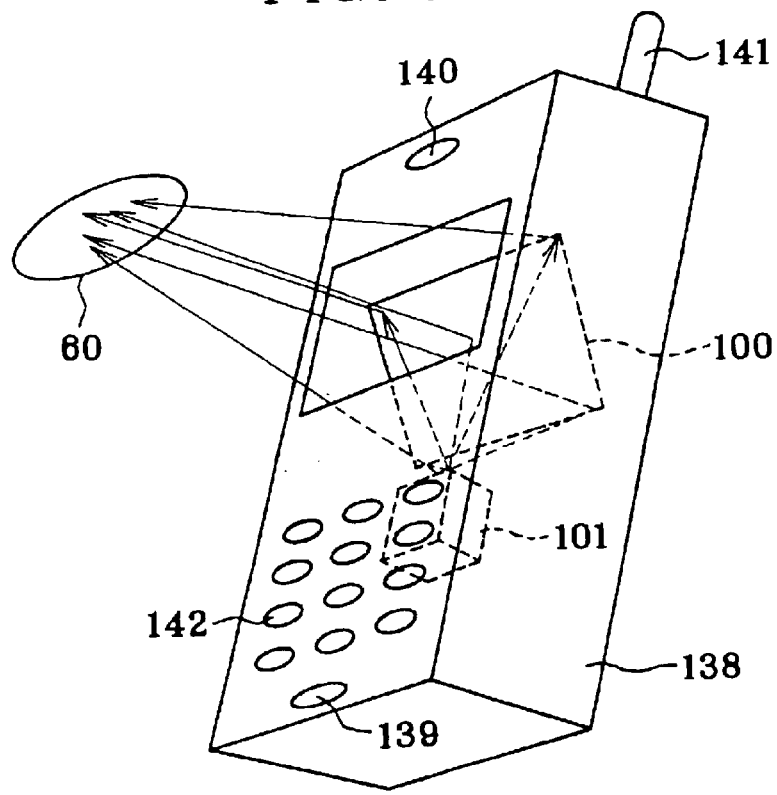
FIG. 66 is a perspective view of another specific cellular phone to which the projection viewing system of the invention is applied.

A typical embodiment of such a projection viewing system, for instance, a cellular phone is shown in FIGS. 65 and 66.

A cellular phone 138 comprises a microphone 139, a speaker 140, an antenna 141 and an operating button 142 and the projection viewing system of the invention. The voice of a user is entered as information in the microphone 139. The speaker 140 produces the voice of the person on the other end. The antenna 141 transmits and receives communication waves. The operating button 142 is used for entrance of information by the user.

The projection viewing system of the invention is used for the projection and display of images taken of the user himself, the person on the other end, etc. and information such as telephone numbers. Here a projector 101 and a reflection type display panel 100 are provided so that an image on the display plane can reasonably be viewed at the position of an exit pupil 60 thereof.

The cellular phone of FIG. 65 has a mechanism for opening or closing the display panel 100 with respect to the cellular phone 138, so that the cellular phone 138 can be folded down during carrying and so received in a pocket or the like. In the cellular phone of FIG. 55, a display panel 100 is fixed in the body of a cellular phone 138, so that the cellular phone can be received in the pocket or the like while it is unfolded.

Figure 67:
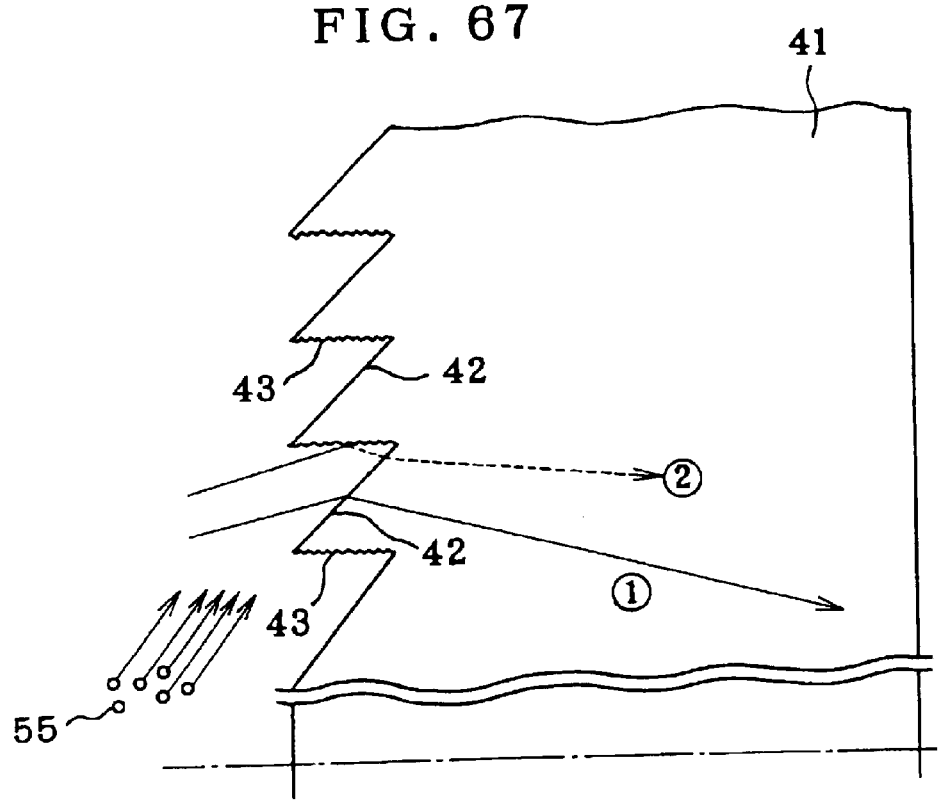
FIG. 67 is illustrative of one arrangement for preventing ghost light at a Fresnel lens used as the eyepiece optical system in the invention.

A Fresnel lens or reflecting mirror could be used as the eyepiece optical system 4 of the projection viewing system according to the invention. In this case, care must be taken of ghost light. In the case of the Fresnel lens, ghost light occurs by the reflection of ambient light, etc. at inactive facets between a zonal array of refracting facets. In the case of the Fresnel reflecting mirror, too, ghost light occurs by the reflection of ambient light, etc. at inactive facets between a zonal array of refracting facets. Incident on exit pupils $60_L$, $60_R$, $60_1$ and $60_2$, the ghost light poses an obstacle to viewing. As shown in FIG. 67, an inactive facet 43 is positioned between a zonal array of refracting facets that form a Fresnel surface. For instance, glass beads 55 are blown onto the inactive facet 43 to turn it to a ground surface. In this case, the glass beads are blown obliquely with respect to the center of a Fresnel lens 41, so that light—which is to turn to ghost light (2) by reflection at that facet—can be diffused. It is preferable to prevent ghost light in this way. More preferably, this ground facet should be coated with a black paint or the like to let it absorb light. In FIG. 67, it is noted that (1) stands for normal refracted light.

Figure 68:
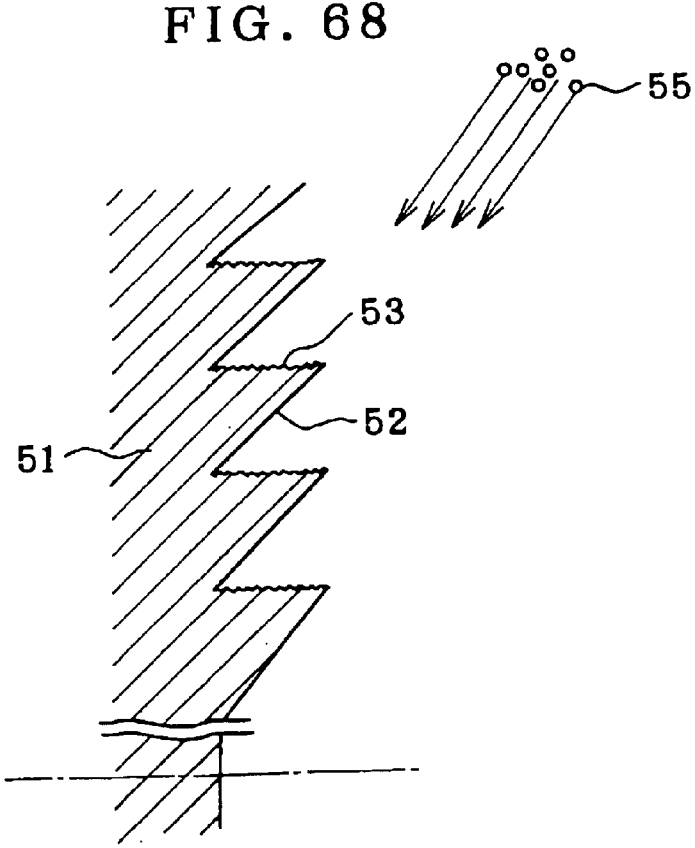
FIG. 68 is illustrative of how to make a mold for the formation of such a Fresnel lens as shown in FIG. 67.

In FIG. 67, glass beads 55 or the like are blown directly to the Fresnel lens 41 to turn the inactive facets to ground facets. However, ghost light could also be prevented by other approaches. One such approach is shown in FIG. 68 as an example. As shown, a mold 51 is used to fabricate a Fresnel lens 41. Glass beads 55 or the like are obliquely blown to facets 53 corresponding to the inactive facets 43 as shown in FIG. 67 to turn them to ground facets, so that the ground facets can be transferred to the Fresnel lens 41. In FIG. 68, facets indicated by reference numeral 52 correspond to a zonal array of refracting facets 42 of the Fresnel lens 41. When the Fresnel reflecting mirror is used for the eyepiece optical system 4, too, it is preferable to rely upon the above approaches.

The diffusing plate used in the invention was prepared as follows, using the fabrication method set forth in Japanese Patent Application No. 2001-370950. First, spherical beads having limited particles were blown to a mold-formation metal plate by means of sandblasting. Then, a random array of concave facets formed on the metal plate was copied to a transparent resin plate by means of transfer. In this way, a single-transmission type diffusing plate was prepared with a random pit-and-projection pattern formed on one surface of the transparent resin plate.

Figure 69:
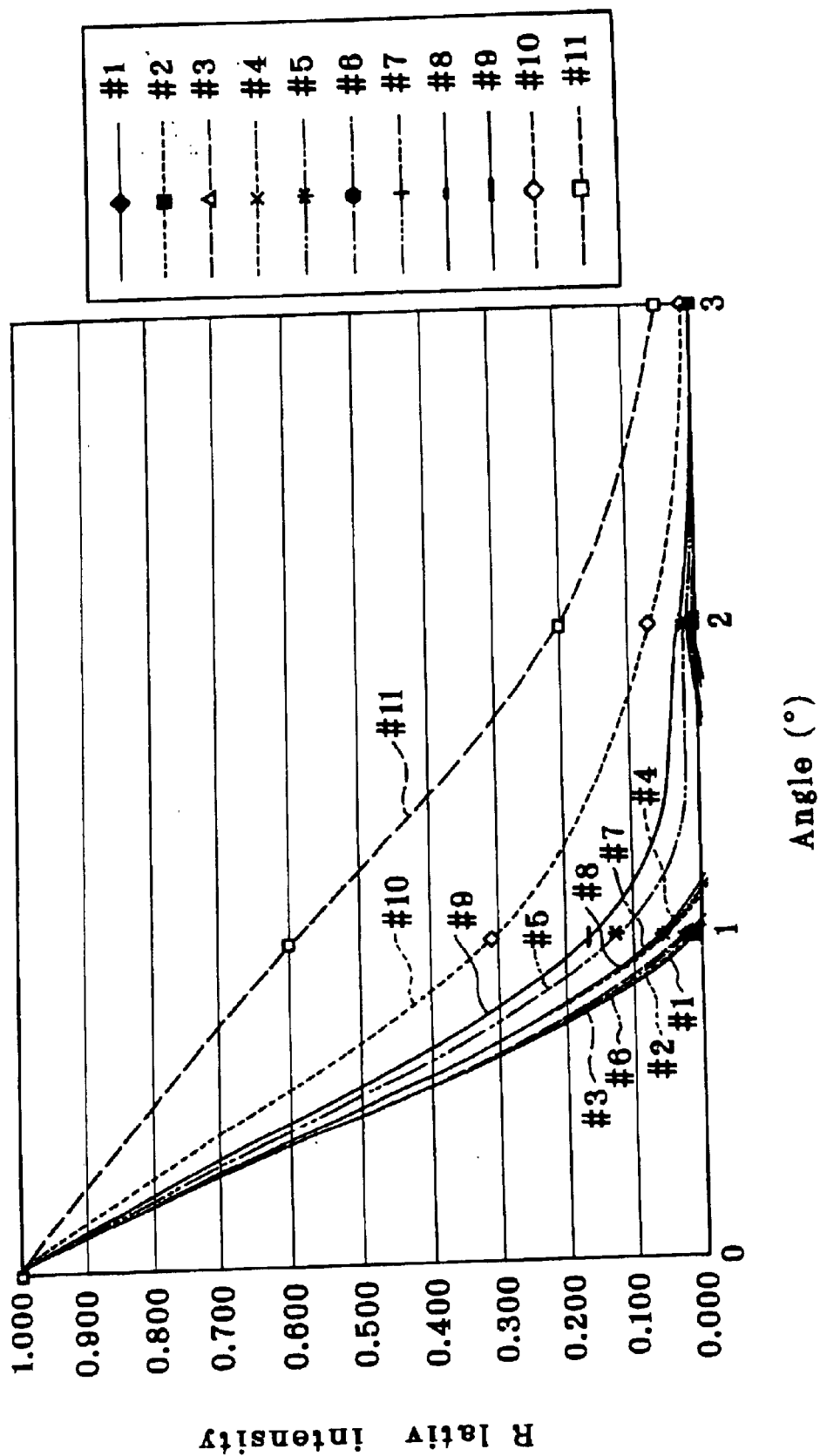
FIG. 69 is a graphical diagram for illustrating the angle distribution for diffused light in a single-transmission type diffusing plate usable in several embodiments of the invention.

Numbered #1 to #11, 11 samples were prepared. Angle distributions of diffused light for diffusing plates #1 to #11 are shown in FIG. 69. The values of Sm/Ra of diffusing plates #1 to #11 and their angles of diffusion at full width half maximum and full width are tabulated below. From this table, it is found that diffusing plate #11 is preferable for the diffusing plate in the above examples and embodiments.

| Sample | Sm/Ra | Angle of diffusion full width half maximum | Angle of diffusion full width |
|--------|-------|---------------------------------|---------------------|
| #1  | 316.67 | 0.096 | 0.858 |
| #2  | 206.25 | 0.104 | 0.980 |
| #3  | 205.88 | 0.114 | 1.164 |
| #4  | 163.64 | 0.144 | 1.510 |
| #5  | 177.78 | 0.230 | 2.236 |
| #6  | 223.53 | 0.108 | 1.062 |
| #7  | 172.00 | 0.148 | 1.572 |
| #8  | 174.07 | 0.156 | 1.632 |
| #9  | 165.52 | 0.286 | 2.572 |
| #10 | 160.61 | 1.368 | 3.470 |
| #11 | 138.46 | 2.470 | 5.040 |

As can be understood from the foregoing, the present invention can provide a projection viewing system that enables images projected or formed at a given position to be simultaneously viewed from different directions. It is also possible to provide a projection viewing system that has high illumination efficiency albeit being simplified in construction. It is further possible to display bright images of identical or different binocular parallaxes on a reduced display plane in a viewable manner.

What we claim is:

1. A projection viewing system, comprising:

an image display device;

a projection optical system configured to magnify and to project an image displayed on the image display device onto a projection position;

a diffusing plate located near the projection position; and an eyepiece optical system configured to project an exit pupil of the projection optical system toward a viewer side, wherein the diffusing plate has an angle of diffusion of up to 20° at full width half maximum.

2. The projection viewing system according to claim 1, wherein said eyepiece optical system comprises a reflecting surface.

3. A projection viewing system, comprising:

an image display device;

a projection optical system configured to magnify and to project an image displayed on the image display device;

a diffusing plate located near an image projected through the projection optical system; and an eyepiece optical system configured to project an exit pupil of the projection optical system toward a viewer side, wherein the diffusing plate has an angle of diffusion of up to 20° at full width half maximum, and said diffusing plate has an angle of diffusion of up to 40° at full width where an intensity of light becomes $\frac{1}{10}$ of a maximum intensity.

4. A projection viewing system, comprising:

an image display device;

a projection optical system configured to magnify and to project an image displayed on the image display device;

a diffusing plate located near an image projected through the projection optical system; and an eyepiece optical system configured to project an exit pupil of the projection optical system toward a viewer side, wherein the diffusing plate has an angle of diffusion of up to 20° at full width half maximum, and said diffusing plate has a surface roughness that satisfies condition (1):

$$5 < (Sm/Ra) < 1{,}000 \qquad (1)$$

where Sm is a surface pit-to-projection mean space in $\mu$m as measured according to JIS B0601, and Ra is a surface center-line mean roughness in $\mu$m.

5. The projection viewing system according to claim 4, which satisfies the following conditions:

with respect to a single transmission type diffusing plate, $$5 < (Sm/Ra) \times (Ep/400) < 70 \quad (2)$$

with respect to a double-transmission type diffusing plate, $$10 < (Sm/Ra) \times (Ep/400) < 80 \quad (3)$$

with respect to a front-surface reflection type diffusing plate, $$50 < (Sm/Ra) \times (Ep/400) < 200 \quad (4)$$

with respect to a back-surface reflection type diffusing plate, $$80 < (Sm/Ra) \times (Ep/400) < 250 \quad (5)$$

where Sm is the surface pit-to-projection mean space in $\mu$m as measured according to JIS B0601, Ra is the surface center-line mean roughness in $\mu$m, and Ep is a distance in mm from the diffusing surface to a position of a viewer's eye.

6. The projection viewing system according to claim 4, which satisfies condition (6):

$$Sm < 200 \, \mu m \quad (6).$$

7. A projection viewing system, comprising:
an image display device;
a projection optical system configured to magnify and to project an image displayed on the image display device;
a diffusing plate located near an image projected through the projection optical system; and
an eyepiece optical system configured to project an exit pupil of the projection optical system toward a viewer side,
wherein the diffusing plate has an angle of diffusion of up to 20° at full width half maximum, and said eyepiece optical system comprises a Fresnel lens.

8. The projection viewing system according to claim 7, wherein said diffusing surface is provided on at least one surface of said eyepiece optical system.

9. A projection viewing system, comprising:
an image display device;
a projection optical system configured to magnify and to project an image displayed on the image display device;
a diffusing plate located near an image projected through the projection optical system; and
an eyepiece optical system configured to project an exit pupil of the projection optical system toward a viewer side,
wherein the diffusing plate has an angle of diffusion of up to 20° at full width half maximum, and said eyepiece optical system comprises a Fresnel reflecting mirror.

10. A projection viewing system comprising:
an image display device;
a projection optical system configured to magnify and to project an image displayed on the image display device;
a diffusing plate located near an image projected through the projection optical system; and
an eyepiece optical system configured to project an exit pupil of the projection optical system toward a viewer side,
wherein the diffusing plate has an angle of diffusion of up to 20° at full width half maximum, and said eyepiece optical system comprises a Fresnel back-surface reflecting mirror.

11. A projection viewing system, comprising:
an image display device;
a projection optical system configured to magnify and to project an image displayed on the image display device;
a diffusing plate located near an image projected through the projection optical system; and
an eyepiece optical system configured to project an exit pupil of the projection optical system toward a viewer side,
wherein the diffusing plate has an angle of diffusion of up to 20° at full width half maximum, and said diffusing plate comprises a transmission hologram, and said eyepiece optical system comprises a concave mirror common to said projection optical system.

12. The projection viewing system according to claim 11, further comprising:
another display device different from said first mentioned display device, and another projection optical system different from said first mentioned projection optical system,
wherein said another projection optical system is configured to magnify and project an image displayed on said another display device.

13. The projection viewing system according to claim 12, wherein said diffusing plate has an angle of diffusion of up to 8° at full width half maximum.

14. The projection viewing system according to claim 12, wherein said diffusing plate has an angle of diffusion of up to 12° at full width where an intensity of light becomes $\frac{1}{10}$ of a maximum intensity.

15. The projection viewing system according to claim 11, wherein said concave mirror comprises a Fresnel concave reflecting mirror.

16. The projection viewing system according to claim 11, wherein a light ray from said projection optical system to an exit pupil of said projection optical system is transmitted twice through said diffusing plate, and said projection optical system and said diffusing plate are located such that an angle of said light ray transmitted through said diffusing plate at a first time is different from an angle of said light ray transmitted through said diffusing plate a second time.

17. The projection viewing system according to claim 11, wherein said diffusing plate has an angle of diffusion of up to 40° at full width where an intensity of light becomes $\frac{1}{10}$ of a maximum intensity.

18. The projection viewing system according to claim 11, wherein said projection viewing system is constructed such that an axial chief ray from said projection optical system is obliquely incident on said concave mirror.

19. The projection viewing system according to claim 11, wherein said projection viewing system is constructed such that zero-order light leaving said diffusing plate is kept from being incident on an exit pupil of said projection viewing system.

20. The projection viewing system according to claim 11, wherein zero-order light leaving said diffusing plate is directed to an exit pupil position of said projection viewing system, and said projection viewing system is constructed such that said zero-order light is incident on a position spaced away from a center of said exit pupil by at least $\frac{1}{2}$ of a diameter of the exit pupil.

21. The projection viewing system according to claim 11, wherein said diffusing plate has a flexing action due to diffraction.

22. The projection viewing system according to claim 21, wherein the projection viewing system satisfies condition (7):

$$\gamma > 1° \qquad (7)$$

where $\gamma$ is an angle of flexion of a d-line light ray by said diffusing plate.

23. The projection viewing system according to claim 21, wherein the projection viewing system satisfies condition (8):

$$\gamma > 45° \qquad (8)$$

where $\gamma$ is an angle of flexion of a d-line light ray by said diffusing plate.

24. The projection viewing system according to claim 11, wherein a difference in an angle of diffraction by said diffusing plate between a light ray having a wavelength of 700 nm and a light ray having a wavelength of 400 nm is up to 18°.

25. The projection viewing system according to claim 11, wherein at an exit pupil position of said projection viewing system, a difference in a position of incidence between a light ray having a wavelength of 700 nm and a light ray having a wavelength of 400 nm is up to ½ of a diameter of said exit pupil.

26. The projection viewing system according to claim 11, wherein the projection viewing system satisfies condition (10):

$$0° < \beta < 45° \qquad (10)$$

where $\beta$ is an angle of incidence of a d-line optical axis on said concave mirror.

27. The projection viewing system according to claim 26, wherein said projection optical system has a function of correcting a tilted image leading to an image distortion.

28. The projection viewing system according to claim 11, wherein the projection viewing system satisfies condition (11):

$$0.01 < \gamma/\beta < 1{,}000 \qquad (11)$$

where $\gamma$ is an angle of flexion of a d-line optical axis by said diffusing plate, and $\beta$ is an angle of incidence of a d-line optical axis on said concave mirror.

* * * * *